US008293758B2

(12) United States Patent
Zemolka et al.

(10) Patent No.: US 8,293,758 B2
(45) Date of Patent: Oct. 23, 2012

(54) SUBSTITUTED SPIROCYCLIC CYCLOHEXANE DERIVATIVES

(75) Inventors: Saskia Zemolka, Aachen (DE); Bert Nolte, Aachen (DE); Sven Frormann, Aachen (DE); Claudia Hinze, Bonn (DE); Klaus Linz, Wachtberg (DE); Wolfgang Schröder, Aachen (DE); Werner Englberger, Stolberg (DE); Hans Schick, Berlin (DE); Helmut Sonnenschein, Berlin (DE)

(73) Assignee: Grunenthal GmbH, Aachen (DE)

( * ) Notice: Subject to any disclaimer, the term of this patent is extended or adjusted under 35 U.S.C. 154(b) by 408 days.

(21) Appl. No.: 12/410,544

(22) Filed: Mar. 25, 2009

(65) Prior Publication Data

US 2009/0247561 A1 Oct. 1, 2009

(30) Foreign Application Priority Data

Mar. 27, 2008 (EP) .................................... 08005808

(51) Int. Cl.
*A61K 31/438* (2006.01)
*A61K 31/407* (2006.01)
*A61P 25/00* (2006.01)
*C07D 491/052* (2006.01)
*C07D 471/04* (2006.01)

(52) U.S. Cl. ........... 514/278; 514/409; 548/407; 546/15

(58) Field of Classification Search .................. None
See application file for complete search history.

(56) References Cited

U.S. PATENT DOCUMENTS

| | | | |
|---|---|---|---|
| 3,328,412 A | 6/1967 | Atkinson et al. | |
| 4,065,573 A | 12/1977 | Lednicer | |
| 4,115,589 A | 9/1978 | Lednicer | |
| 4,291,039 A | 9/1981 | Van Dyke, Jr. et al. | |
| 4,366,172 A | 12/1982 | Lednicer | |
| 4,575,508 A | 3/1986 | Steiner et al. | |
| 5,328,905 A | 7/1994 | Hamminga et al. | |
| 5,631,265 A | 5/1997 | Audia et al. | |
| 5,760,051 A | 6/1998 | Audia et al. | |
| 5,869,691 A | 2/1999 | Audia et al. | |
| 7,332,519 B2 | 2/2008 | Hinze et al. | |
| 7,485,634 B2 | 2/2009 | Martin et al. | |
| 7,507,758 B2 | 3/2009 | Sundermann et al. | |
| 7,547,707 B2 * | 6/2009 | Hinze et al. ................... | 514/278 |
| 7,595,311 B2 | 9/2009 | Busch et al. | |
| 7,799,931 B2 | 9/2010 | Hinze et al. | |
| 7,960,404 B2 | 6/2011 | Schunk et al. | |
| 7,977,370 B2 | 7/2011 | Zemolka et al. | |
| 8,053,576 B2 | 11/2011 | Hinze et al. | |
| 8,133,992 B2 | 3/2012 | Martin et al. | |
| 8,143,257 B2 | 3/2012 | Choi et al. | |
| 2003/0236250 A1 | 12/2003 | Pineiro et al. | |
| 2004/0023947 A1 | 2/2004 | Martin et al. | |
| 2005/0192333 A1 | 9/2005 | Hinze et al. | |
| 2005/0267107 A1 | 12/2005 | Sundermann et al. | |
| 2006/0004034 A1 | 1/2006 | Hinze et al. | |
| 2006/0235012 A1 | 10/2006 | Davidson et al. | |
| 2007/0149557 A1 | 6/2007 | Collins et al. | |
| 2008/0125475 A1 | 5/2008 | Linz et al. | |
| 2008/0221141 A1 | 9/2008 | Friderichs et al. | |
| 2008/0261956 A1 | 10/2008 | Choi et al. | |
| 2008/0280942 A1 | 11/2008 | Diaz-Fernandez et al. | |
| 2009/0042866 A1 | 2/2009 | Lennox et al. | |
| 2009/0156626 A1 | 6/2009 | Hinze et al. | |
| 2009/0163716 A1 | 6/2009 | Hinze et al. | |
| 2009/0247505 A1 | 10/2009 | Zemolka et al. | |
| 2009/0247530 A1 | 10/2009 | Nolte et al. | |
| 2009/0247561 A1 | 10/2009 | Zemolka et al. | |
| 2009/0247573 A1 | 10/2009 | Zemolka et al. | |
| 2009/0247591 A1 | 10/2009 | Zemolka et al. | |
| 2009/0326218 A1 | 12/2009 | Martin et al. | |
| 2010/0009986 A1 | 1/2010 | Zemolka et al. | |
| 2010/0048553 A1 | 2/2010 | Schunk et al. | |
| 2010/0048554 A1 | 2/2010 | Schunk et al. | |
| 2010/0173824 A1 | 7/2010 | Busch et al. | |
| 2011/0015220 A1 | 1/2011 | Linz et al. | |
| 2011/0059999 A1 | 3/2011 | Frormann et al. | |

FOREIGN PATENT DOCUMENTS

| | | |
|---|---|---|
| AR | 071066 | 5/2010 |
| AR | 071067 | 5/2010 |
| AR | 071068 | 5/2010 |
| AR | 073841 | 12/2010 |
| AU | 2009228637 | 10/2009 |
| AU | 2009228642 | 10/2009 |
| AU | 2009228643 | 10/2009 |
| AU | 2009228645 | 10/2009 |
| AU | 2009228647 | 10/2009 |
| AU | 2009228648 | 10/2009 |
| CA | 2446461 A1 | 11/2002 |
| CA | 2550868 | 7/2005 |
| CA | 2658376 A1 | 1/2008 |
| CA | 2658379 | 1/2008 |
| CA | 2718209 | 10/2009 |
| CA | 2719735 | 10/2009 |
| CA | 2719736 | 10/2009 |

(Continued)

OTHER PUBLICATIONS

Patani et al., Chem. Rev., 1996, vol. 96, p. 3147-3176.*
Maddox et al., J. Med. Chem., 1965, 8, 230-235.
Elliott et al. Bioorg. Med. Chem. Lett.; EN; 16; 2006; 2929-2932.
Jirkovsky et al.; J. Heterocycl. Chem., 12, 1975, 937-940.
Beck et al., J. Chem. Soc. Perkin 1, 1992, 813-822.
Shinada et al., Tetrahedron Lett., 39, 1996, 7099-7102.
Garden et al., Tetrahedron, 58, 2002, 8399-8412.
Lednicer et al., J. Med. Chem., 23, 1980, 424-430.
Bandini et al. J. Org. Chem. 67, 15; 2002, 5386-5389.
Davis et al., J. Med. Chem. 35, 1, 1992, 177-184.
Yamagishi et al., J. Med. Chem. 35, 11, 1992, 2085-2094.
Gleave et al.; Bioorg. Med. Chem. Lett. 8, 10, 1998, 1231-1236.
Sandmeyer, Helv. Chim. Acta; 2; 1919; 239.
Katz et al.; J. Med. Chem. 31, 6, 1988; 1244-1250.
Bac et al. Tetrahedron Lett. 1988, 29, 2819.
Ma et al. J. Org. Chem. 2001, 66, 4525.

(Continued)

*Primary Examiner* — Yong Chu
(74) *Attorney, Agent, or Firm* — Norris McLaughlin & Marcus, P.A.

(57) ABSTRACT

The invention relates to compounds that have an affinity to the μ-opioid receptor and the ORL1-receptor, methods for their production, medications containing these compounds and the use of these compounds for the treatment of pain and other conditions.

9 Claims, No Drawings

FOREIGN PATENT DOCUMENTS

| | | |
|---|---|---|
| CA | 2719739 | 10/2009 |
| CA | 2719742 | 10/2009 |
| CA | 2719743 | 10/2009 |
| CA | 2446461 C | 4/2011 |
| DE | 28 39 891 | 4/1979 |
| EP | 2260022 | 10/2009 |
| EP | 2257526 | 12/2010 |
| EP | 2260021 | 12/2010 |
| EP | 2260042 | 12/2010 |
| EP | 2271613 | 1/2011 |
| EP | 2280941 | 2/2011 |
| GB | 1 055 203 | 1/1967 |
| KR | 20100132048 | 12/2010 |
| KR | 20100136521 | 12/2010 |
| MX | 2010009955 | 9/2010 |
| MX | 2010010337 | 10/2010 |
| MX | 2010010339 | 10/2010 |
| MX | 2010010407 | 10/2010 |
| MX | 2010010446 | 11/2010 |
| MX | 2010010448 | 11/2010 |
| PE | 16502009 | 11/2009 |
| PE | 16572009 | 11/2009 |
| PE | 18222009 | 12/2009 |
| PE | 18232009 | 12/2009 |
| PE | 16892009 | 11/2011 |
| WO | 01 87838 | 11/2001 |
| WO | 02 90330 | 5/2002 |
| WO | 02 090317 | 11/2002 |
| WO | 03 008370 | 1/2003 |
| WO | 03 008731 | 1/2003 |
| WO | 03 080557 | 1/2003 |
| WO | 2004 043899 | 5/2004 |
| WO | 2004 043900 | 5/2004 |
| WO | 2004 043902 | 5/2004 |
| WO | 2004 043909 | 5/2004 |
| WO | 2004 043949 | 5/2004 |
| WO | 2004 043967 | 5/2004 |
| WO | 2005 063769 | 7/2004 |
| WO | 2005 066183 | 7/2005 |
| WO | 2005 110970 | 11/2005 |
| WO | 2005 110971 | 11/2005 |
| WO | 2005 110973 | 11/2005 |
| WO | 2005 110974 | 11/2005 |
| WO | 2005 110975 | 11/2005 |
| WO | 2005 110976 | 11/2005 |
| WO | 2005 110977 | 11/2005 |
| WO | 2006 018184 | 2/2006 |
| WO | 2006058088 | 6/2006 |
| WO | 2006065479 | 6/2006 |
| WO | 2006065480 | 6/2006 |
| WO | 2006 108565 | 10/2006 |
| WO | 2007 079927 | 7/2007 |
| WO | 2007 079928 | 7/2007 |
| WO | 2007 079930 | 7/2007 |
| WO | 2007 079931 | 7/2007 |
| WO | 2007 124903 | 11/2007 |
| WO | 2008 009415 | 1/2008 |
| WO | 2008 009416 | 1/2008 |
| WO | 2008 040481 A1 | 4/2008 |
| WO | 2008040481 A1 | 4/2008 |
| WO | 2008 101660 A1 | 8/2008 |
| WO | 2008101659 A1 | 8/2008 |
| WO | 2008101660 A1 | 8/2008 |
| WO | 2009 118173 | 3/2009 |
| WO | 2009118163 | 10/2009 |
| WO | 2009118168 | 10/2009 |
| WO | 2009118169 | 10/2009 |
| WO | 2009118171 | 10/2009 |
| WO | 2009118174 | 10/2009 |

OTHER PUBLICATIONS

Kato et al. J. Fluorine Chem. 99, 1, 1999, 5-8.
Katritzky et al, Synthesis 1989; 66-69.
Shiner et al; J. Am. Chem. Soc. 1981, 103; 436-442.
Xia, et al; Organic Letters 2005, vol. 7, No. 7; 1315-1318.
Messina et al; Tetrahedron: Asymmetry 11 (2000), 1681-1685.
Greene et al; Protective Groups in Organic Synthesis; Wiley Interscience publication; 3rd Edition 1999.
Williams et al; J. Org. Chem. 1980, 45, p. 5082-5088.
Piper, et al; Journal of Medicinal Chemistry US American Chemical Society, Washington, No. 9, Jan. 1, 1966; p. 911-920.
Gilbert, et al; Journal of the American Chemical Society, 1950, No. 72, pp. 2411-2417.
Chu, et al; Tetrahedron, Elsevier Science Publishers, Amsterdam, NL, No. 62, 2006, pp. 5536-5548.
Corey et al; Tetrahedron Letters, No. 36, pp. 3769-3772 (1972).
D'Amour et al; The Biologic Research Laboratory, pp. 74-79, Jan. 27, 1941.
Harned et al; Tetrahedron, No. 66, pp. 12093-12099 (2005).
Katritzky et al; Synthesis, pp. 1295-1298, Dec. 1992.
Kudzma et al, J. Med. Chem. No. 32, pp. 2534-2542 (1989).
Layer, B.F. Goodrich Co. Research Center, pp. 489-510, Dec. 7, 1962.
Prashad et al; Tetrahedron Letters No. 46, pp. 5455-5458 (2005).
Regitz et al; Chem. Ber. No. 101, pp. 3734-3743 (1968).
Bavetsias et al.; J. Med. Chem., No. 43, pp. 1910-1926 (2000).
Catterall et al.; The Journal of Biological Chemistry, vol. 256, No. 17, pp. 8922-8927, Sep. 10, 1981.
Dirat et al.; Tetrahedron Letters No. 47, pp. 12095-1298 (2006).
Hamzé et al; J. Org. Chem. No. 678, pp. 7316-7321 (2003).
Hashmi et al; Organic Letters, vol. 6, No. 23, pp. 4391-4394 (2004).
Kim et al; Elsevier Science Publishers B.V. No. 50, pp. 355-363 (1992).
Lee et al; Bull. Koren Chem. Soc. vol. 25, No. 2, pp. 207-212 (2004).
Thompson et al; Journal of Medical Chemistry, vol. 41, No. 21, pp. 3923-3927 (1998).
Morwick et al; Organic Letters, vol. 4, No. 16, pp. 2665-2668, (2002).
Gaspar et al. Mild Cobalt-Catalyzed Hydrocyanation of Olefins with Tosyl Cyanide. Angew. Chemie. Int. Ed. 2007, vol. 46, pp. 4519-4522.
Lednicer et al., "4-Amino-4-arylcyclohexanones and Their Derivatives, a Novel Class of Analgesics. 1. Modification of the Aryl Ring", The Upjohn Company, Research Laboratories, Aug. 7, 1979.
Finlayson, et al., European Journal of Pharmacology, 412 (2001), pp. 203-212.
Jenck, et al, "Orphanin FQ acts as an anxiolytic to attenuate behavioral responses to stress"; Proc. Natl. Acad. Sci. USA, vol. 94, Dec. 1997, pp. 14854-14858.
King et al, "Spinal analgesic activity of orphanin FQ/nociceptin and its fragments", Neuroscience Letters 223 (1997), pp. 113-116.
Meunier, et al, "Isolation and structure of the endogenous agonist of opioid receptor-like ORL1 receptor", Nature, vol. 377, Oct. 12, 1995, pp. 532-535.
Mogil, et al, "Orphanin FQ is a Functional Anti-Opioid Peptide"; Neuroscience, vol. 75, No. 2, 1996, pp. 333-337.
Reinscheid, et al, "Orphanin FQ: A Neuropepetide that Activates an Opioidlike G Protein-Coupled Receptor", Science, vol. 270, Nov. 3, 1995, pp. 792-794.
Rose et al, Can J. Chem., 74, 1996, 1836.
Abdulla et al, "Axotomy Reduces the Effect of Analgesic Opioids Yet Increases the Effect of Nociceptin on Dorsal Root Ganglion Neurons"; The Journal of Neurosciene, Dec. 1, 1998, 18 (23), pp. 9685-9694.
Manabe et al, "Facilitation of long-term potentiation and memory in mice lacking nociceptin receptors"; Nature, vol. 394, Aug. 6, 1998, pp. 577-581.
Nishi et al, "Unrestrained nociceptive response and disregulation of hearing ability in mice lacking the nociceptin/ orphaninFQ receptor"; The EMBO Journal, vol. 16, No. 8, 1997, pp. 1858-1864.
Calo, et al, "Pharmacology of nociceptin and its receptor: a novel therapeutic target"; British Journal of Pharmacology (2000) 129, pp. 1261-1283.
Dorwald, F. A., Side reactions in Oranic Synthesis, 2005, Wiley: VCH, Weinheim p. IX of Preface.
Ardati, Mol. Pharmacol., 51, 1997, pp. 816-824.

* cited by examiner

SUBSTITUTED SPIROCYCLIC CYCLOHEXANE DERIVATIVES

The invention relates to substituted spirocyclic cyclohexane derivatives that have an affinity to the μ-opioid receptor and the ORL 1-receptor, methods for their production, medications containing these compounds and the use of these compounds for the production of medications.

Spirocyclic cyclohexane derivatives that have an affinity to the μ-opioid receptor and the ORL 1-receptor are known in the prior art. In this context, reference can be made, for example, to the following documents in their full scope WO2004/043967, WO2005/063769, WO2005/066183, WO2006/018184, WO2006/108565, WO2007/124903 and WO2008/009416.

However, the known compounds are not satisfactory in every respect and there is a need for further compounds with comparable or better properties.

Thus, in appropriate binding assays the known compounds occasionally exhibit a certain affinity to the hERG ion channel, the L-type calcium ion channel (phenylalkylamine, benzothiazepine, dihydropyridine binding sites) or to the sodium channel in the BTX assay (batrachotoxin), which can be respectively interpreted as an indication of cardiovascular side-effects. Moreover, many of the known compounds exhibit only a slight solubility in aqueous media, which can adversely affect the bioavailability, inter alia. In addition, the chemical stability of the known compounds is often merely inadequate. Thus, the compounds occasionally do not exhibit an adequate pH, UV or oxidation stability, which can adversely affect the storage stability and also the oral bioavailability, inter alia. Moreover, the known compounds have an unfavourable PK/PD (pharmacokinetic/pharmacodynamic) profile in some instances, which can be displayed, for example, in too long a duration of effect.

The metabolic stability of the known compounds also appears to be in need of improvement. An improved metabolic stability can point to an increased bioavailability. A weak or absent interaction with transporter molecules that participate in the absorption and excretion of medicinal substances should be considered an indication of an improved bioavailability and possibly low interactions of medications. Moreover, the interactions with the enzymes involved in the breakdown and excretion of medicinal substances should also be as low as possible, since such test results also indicate that low interactions of medications or none at all are possibly to be expected.

The object forming the basis of the invention is to provide compounds that are suitable for pharmaceutical purposes and have advantages over the compounds of the prior art.

This object is achieved by the compounds described hereinbelow.

It has been surprisingly found that substituted spirocyclic cyclohexane derivatives can be produced that have an affinity to the μ-opioid receptor and the ORL 1-receptor.

The invention relates to compounds of the general formula (1)

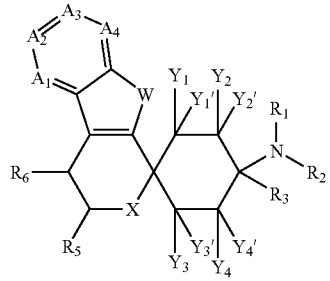

wherein
$A_1$ stands for —N= or —$CR_7$=,
$A_2$ stands for —N= or —$CR_8$=,
$A_3$ stands for —N= or —$CR_9$=,
$A_4$ stands for —N= or —$CR_{10}$=;
on condition that at most two of the residues $A_1$, $A_2$, $A_3$ and $A_4$, preferably 0, 1 or 2 or the residues $A_1$, $A_2$, $A_3$ and $A_4$, stand for —N=;
W stands for —$NR_4$—, —O— or —S—, preferably for —$NR_4$— or —O—;
X stands for —$NR_{17}$—, —O—, —S(=O)$_{0-2}$— or —$CR_{18}R_{19}$—, preferably for —$NR_{17}$— or —O—;
$Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NO$_2$, —CHO, —R$_0$, —C(=O)R$_0$, —C(=O)—H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NHC(=O)—N(R$_0$)$_2$; preferably respectively selected independently of the group comprising —H, —F, —Cl, —CN, —$C_{1-8}$-aliphatic, —$C_{1-8}$-aliphatic-NHC$_{1-8}$-aliphatic, —$C_{1-8}$-aliphatic-N(C$_{1-8}$-aliphatic)$_2$, —S—$C_{1-8}$-aliphatic, —S-aryl, -aryl, —$C_{1-8}$-aliphatic-aryl; or $Y_1$ and $Y_1'$, or $Y_2$ and $Y_2'$, or $Y_3$ and $Y_3'$, or $Y_4$ and $Y_4'$ jointly stand for =O;
on condition that at least one of the residues $Y_1$, $Y_1'$, $Y_2$, $Y_2'$, $Y_3$, $Y_3'$, $Y_4$ and $Y_4'$, preferably one or two of the residues $Y_1$, $Y_1'$, $Y_2$, $Y_2'$, $Y_3$, $Y_3'$, $Y_4$ and $Y_4'$, does not stand for —H;
$R_0$ respectively independently stands for —$C_{1-8}$-aliphatic, —$C_{3-12}$-cycloaliphatic, -aryl, heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;
$R_1$ and $R_2$, independently of one another, stand for —H or —$R_0$; or $R_1$ and $R_2$ together stand for —CH$_2$CH$_2$OCH$_2$CH$_2$—, —CH$_2$CH$_2$NR$_{11}$CH$_2$CH$_2$— or —(CH$_2$)$_{3-6}$—;
$R_3$ stands for —$R_0$;
$R_4$ stands for —H, —R$_0$, —COR$_{12}$ or —S(=O)$_2$R$_{12}$;
$R_5$, $R_6$, $R_7$, $R_8$, $R_9$, $R_{10}$, $R_{18}$ and $R_{19}$, respectively independently of one another, stand for —H, —F, —Cl, —Br, —I, —NO$_2$, —CF$_3$, —OR$_{13}$, —SR$_{13}$, —SO$_2$R$_{13}$, —S(=O)$_2$OR$_{13}$, —CN, —COOR$_{13}$, —CONR$_{13}$, —NR$_{14}$R$_{15}$, =O or —R$_0$; or $R_5$ and $R_6$ jointly stand for —(CH$_2$)$_{2-6}$—, wherein individual hydrogen atoms can also be replaced by —F, —Cl, —Br, —I, —NO$_2$, —CF$_3$, —OR$_{13}$, —CN or —$C_{1-6}$-aliphatic;

$R_{11}$ respectively independently stands for —H, —$R_0$ or —C(=O)$R_0$;

$R_{12}$ respectively independently stands for —H, —$R_0$, —$OR_{13}$, or —$NR_{14}R_{15}$;

$R_{13}$ respectively independently stands for —H or $R_0$;

$R_{14}$ and $R_{15}$ respectively independently of one another stand for —H or $R_0$; or $R_{14}$ and $R_{15}$ together stand for —$CH_2CH_2OCH_2CH_2$—, —$CH_2CH_2NR_{16}CH_2CH_2$— or —$(CH_2)_{3-6}$—;

$R_{16}$ stands for —H or —$C_{1-6}$-aliphatic;

$R_{17}$ stands for —H, —$R_0$, —$COR_{12}$ or —S(=O)$_2R_{12}$;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue, the number of ring-carbon atoms of which preferably lies in the specified range (i.e. "$C_{3-8}$-cycloaliphatic" preferably has 3, 4, 5, 6, 7 or 8 ring-carbon atoms);

wherein with respect to "aliphatic" and "cycloaliphatic", "mono- or polysubstituted" is understood to mean the mono- or polysubstitution of one or more hydrogen atoms, e.g. the mono-, di-, tri- or complete substitution, by substituents selected independently of one another from the group comprising —F, —Cl, —Br, —I, —CN, —$NO_2$, —CHO, =O, —$R_0$, —C(=O)$R_0$, —C(=O)H, —C(=O)OH, —C(=O)$OR_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)—$OR_0$, —OC(=O)$NHR_0$, —OC(=O)N($R_0$)$_2$, —SH, —$SR_0$, —$SO_3$H, —S(=O)$_{1-2}$—$R_0$, —S(=O)$_{1-2}NH_2$, —$NH_2$, —$NHR_0$, —N($R_0$)$_2$, —$N^+$($R_0$)$_3$, —$N^+$($R_0$)$_2O^-$, —NHC(=O)$R_0$, —NHC(=O)$OR_0$, —NHC(=O)$NH_2$, —NHC(=O)$NHR_0$, —NH—C(=O)—N($R_0$)$_2$, —Si($R_0$)$_3$, —PO($OR_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" is understood to mean the mono- or polysubstitution of one or more hydrogen atoms of the ring system by substituents selected from the group comprising —F, —Cl, —Br, —I, —CN, —$NO_2$, —CHO, =O, —$R_0$, —C(=O)$R_0$, —C(=O)H, —C(=O)OH, —C(=O)$OR_0$, —C(=O)$NH_2$, —C(=O)$NHR_0$, —C(=O)—N($R_0$)$_2$, —OH, —O($CH_2$)$_{1-2}$O—, —$OR_0$, —OC(=O)H, —OC(=O)$R_0$, —OC(=O)$OR_0$, —OC(=O)$NHR_0$, —OC(=O)N($R_0$)$_2$, —SH, —$SR_0$, —$SO_3$H, —S(=O)$_{1-2}$—$R_0$, —S(=O)$_{1-2}NH_2$, —$NH_2$, —$NHR_0$, —N($R_0$)$_2$, —$N^+$($R_0$)$_3$, —$N^+$($R_0$)$_2O^-$, —NHC(=O)$R_0$, —NHC(=O)$OR_0$, —NHC(=O)$NH_2$, —NHC(=O)$NHR_0$, —NHC(=O)N($R_0$)$_2$, —Si($R_0$)$_3$, —PO($OR_0$)$_2$; wherein any N-ring atoms present can be respectively oxidised (N-oxide);

in the form of a single stereoisomer or mixture thereof, the free compounds and/or their physiologically compatible salts and/or solvates.

In the combination of different residues, e.g. $R_7$, $R_8$, $R_9$ and $R_{10}$, and also the combination of residues at substituents thereof such as e.g. —$OR_{13}$, —$SR_{13}$, —$SO_2R_{13}$ or —$COOR_{13}$, a substituent, e.g. $R_{13}$, can assume different meanings within a substance for two or more residues, e.g. $R_7$, $R_8$, $R_9$ and $R_{10}$.

The compounds according to the invention exhibit favourable binding to the ORL1-receptor and the μ-opioid receptor.

In a preferred embodiment, the compounds according to the invention have an affinity ratio of ORL 1/μ of at least 0.1. The ORL1/μ ratio is defined as $1/[K_{i(ORL1)}/K_{i(\mu)}]$. It is particularly preferred if the ORL1/μ ratio amounts to at least 0.2 or at least 0.5, more preferred at least 1.0 or at least 2.0, further preferred at least 3.0 or at least 4.0, most preferred at least 5.0 or at least 7.5 and in particular at least 10 or at least 15. In a preferred embodiment the ORL1/μ ratio lies in the range of 0.1 to 30, more preferred 0.1 to 25.

In another preferred embodiment, the compounds according to the invention have an ORL1/μ affinity ratio of more than 30, more preferred at least 50, further preferred at least 100, most preferred at least 200 and in particular at least 300.

The compounds according to the invention preferably have a $K_i$ value on the μ-opioid receptor of at maximum 500 nM, more preferred at maximum 100 nM, further preferred at maximum 50 nM, most preferred at maximum 10 nM and in particular at maximum 1.0 nM.

Methods for determining the $K_i$ value on the μ-opioid receptor are known to the person skilled in the art. The determination is preferably conducted as described in association with the examples.

It has surprisingly been shown that compounds with an affinity to the ORL 1- and μ-opioid receptor, in which the ratio of ORL 1 to μ defined by $1/[K_{i(ORL1)}/K_{i(\mu)}]$ lies in the range of 0.1 to 30, preferably 0.1 to 25, have a pharmacological profile that has significant advantages compared to the other opioid receptor ligand:

1. The compounds according to the invention exhibit an efficacy in acute pain models that is at times comparable with the usual stage-3 opioids. However, they are distinguished at the same time by a significantly better compatibility compared to classic μ-opioids.
2. In contrast to common stage-3 opioids, the compounds according to the invention exhibit a significantly higher efficacy in mono- and polyneuropathic pain models, which is attributable to a synergy of ORL 1- and μ-opioid components.
3. In contrast to common stage-3 opioids, the compounds according to the invention exhibit in neuropathic animals a substantial, preferably a complete, separation of antiallodynic or antihyperalgesic effect and antinociceptive effect.
4. In contrast to common stage-3 opioids, in animal models the compounds according to the invention exhibit a significant increase in efficacy for chronic inflammatory pain (carageenan- or CFA-induced hyperalgesia, visceral inflammatory pain, amongst others) compared to acute pain.
5. In contrast to common stage-3 opioids, side-effects typical of μ-opioids (respiratory depression, opioid-induced hyperalgesia, physical dependence/withdrawal, psychic dependence/addiction, among others) are significantly reduced or preferably not observed with the compounds according to the invention in the therapeutically effective dose range.

In view of the reduced μ-opioid side-effects, on the one hand, and the increased efficacy in chronic, preferably neuropathic pain, on the other hand, the mixed ORL 1/μ agonists are thus distinguished by significantly increased safety margins compared to pure μ-opioids. This results in a significantly increased "therapeutic window" in the treatment of pain conditions, preferably chronic pain, more preferred neuropathic pain.

Preferred embodiments of the compounds according to the invention of the general formula (1) have the general formula (1.1), (1.2), (1.3), (1.4), (1.5), (1.6) or (1.7):

(1.1)
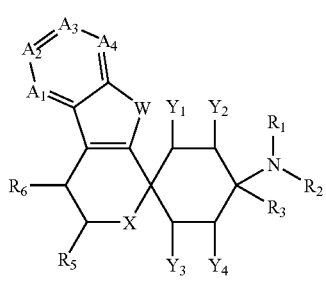

(1.2)
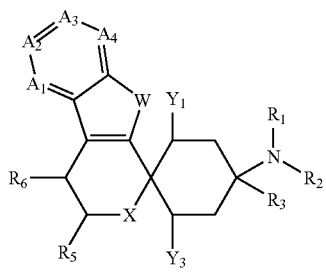

(1.3)
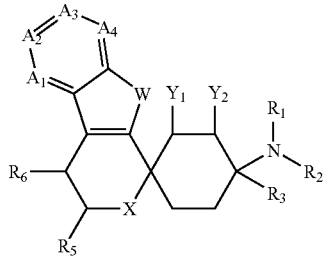

(1.4)
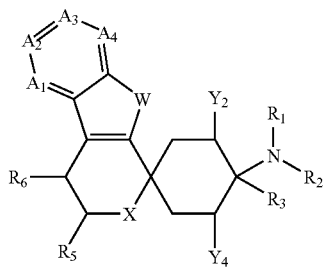

(1.5)
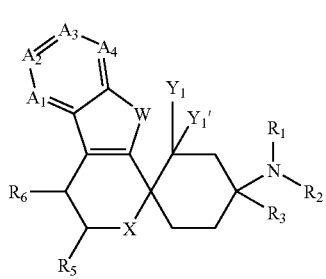

(1.6)
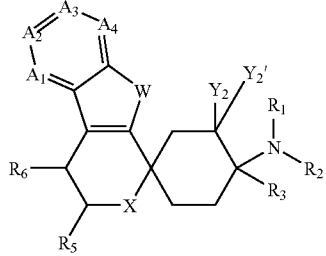

(1.7)
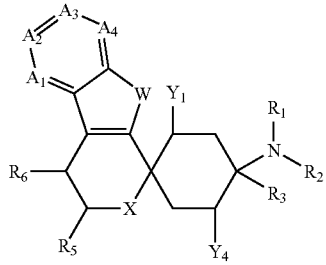

in which some of the residues $Y_1, Y_1', Y_2, Y_2', Y_3, Y_3', Y_4$ and $Y_4'$ respectively represent —H and only those residues that possibly differ from —H (but can also be —H) are shown.

In a preferred embodiment of the compounds (1.1), (1.2), (1.3), (1.4), (1.5), (1.6) or (1.7) according to the invention $A_1$, $A_2$, $A_3$ and $A_4$ differ from —N=. In another preferred embodiment of the compounds (1.1), (1.2), (1.3), (1.4), (1.5), (1.6) or (1.7) according to the invention three of the residues $A_1$, $A_2$, $A_3$ and $A_4$ differ from —N= and the remaining residue is —N=. Preferably, $A_1$, $A_2$ and $A_3$ differ from —N=; or $A_1$, $A_2$ and $A_4$ differ from —N=; or $A_1$, $A_3$ and $A_4$ differ from —N=; or $A_2$, $A_3$ and $A_4$ differ from —N=. In another preferred embodiment of the compounds (1.1), (1.2), (1.3), (1.4), (1.5), (1.6) or (1.7) according to the invention two of the residues $A_1$, $A_2$, $A_3$ and $A_4$ differ from —N= and the other two residues are —N=. Preferably, $A_1$ and $A_2$ are —N= and $A_3$ and $A_4$ differ from —N=; or $A_2$ and $A_3$ are —N= and $A_1$ and $A_4$ differ from —N=; or $A_3$ and $A_4$ are —N= and $A_1$ and $A_2$ differ from —N=; or $A_1$ and $A_3$ are —N= and $A_2$ and $A_4$ differ from —N=; or $A_1$ and $A_4$ are —N= and $A_2$ and $A_3$ differ from —N=; or $A_2$ and $A_4$ are —N= and $A_1$ and $A_3$ differ from —N=;

A preferred embodiment of the invention relates to compounds with the general formula (1.1.1), (1.1.2), (1.1.3) or (1.1.4)

(1.1.1)
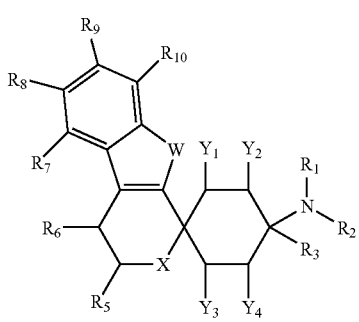

-continued
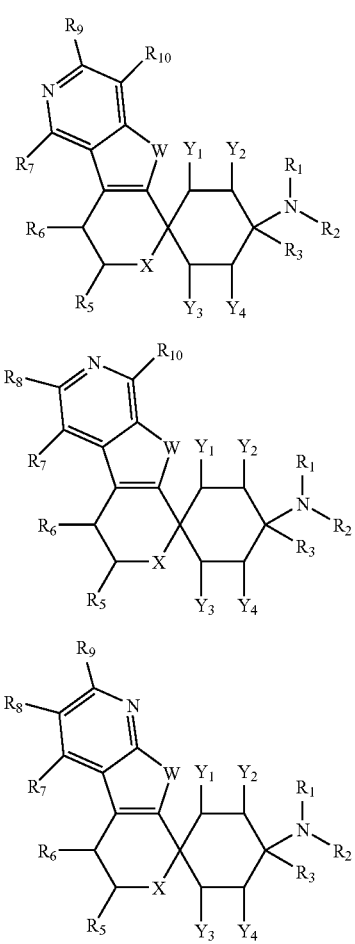
Another preferred embodiment of the invention relates to compounds of the general formula (1.2.1), (1.2.2), (1.2.3) or (1.2.4)
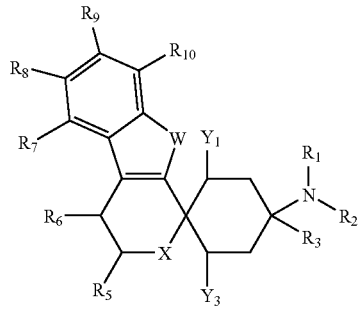
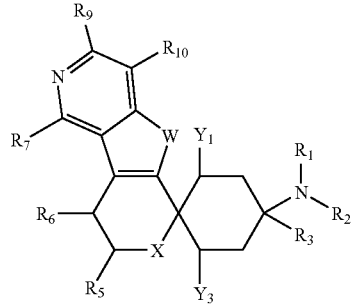
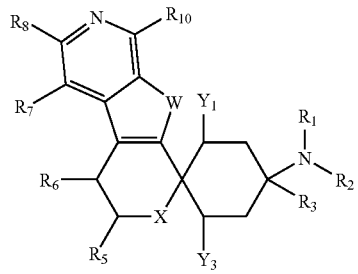
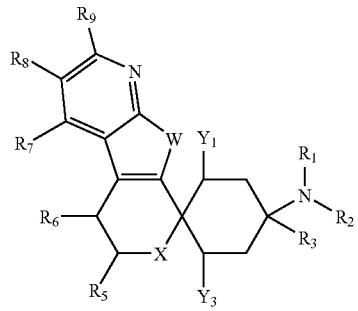
Another preferred embodiment of the invention relates to compounds of the general formula (1.3.1), (1.3.2), (1.3.3) or (1.3.4)
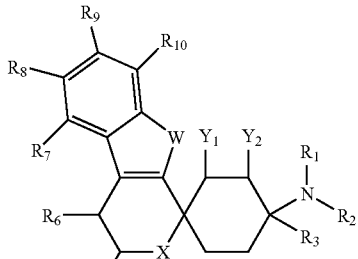
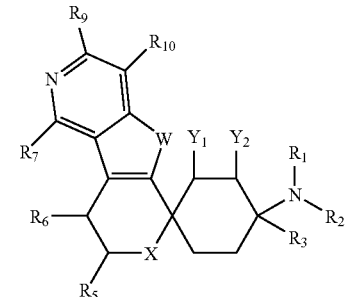
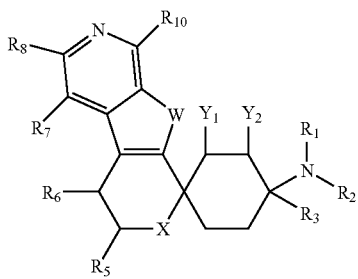

-continued
(1.3.4)
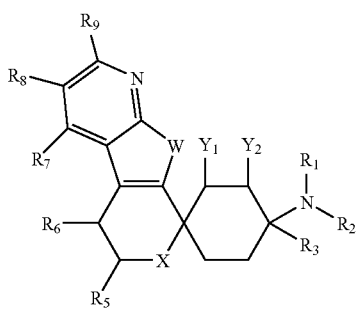
A further preferred embodiment of the invention relates to compounds of the general formula (1.4.1), (1.4.2), (1.4.3) or (1.4.4)
(1.4.1)
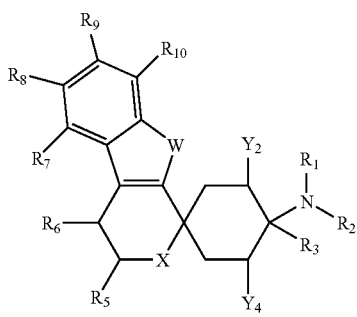
(1.4.2)
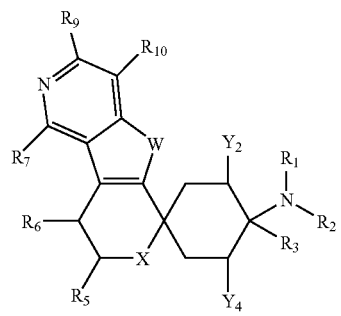
(1.4.3)
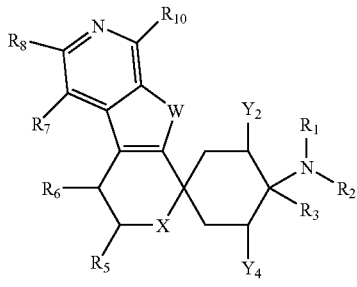
(1.4.4)
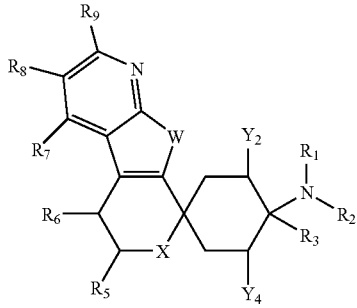
A further preferred embodiment of the invention relates to compounds of the general formula (1.5.1), (1.5.2), (1.5.3) or (1.5.4)
(1.5.1)
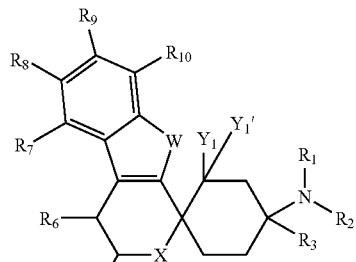
(1.5.2)
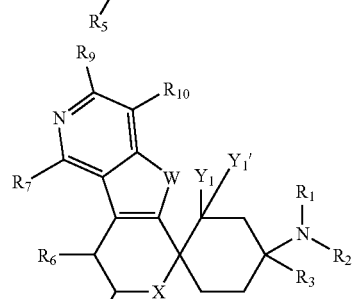
(1.5.3)
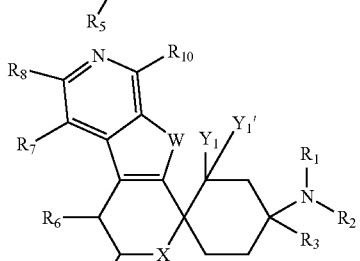
(1.5.4)
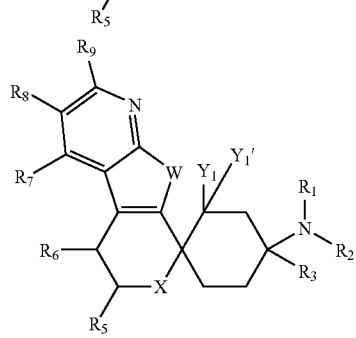
A further preferred embodiment of the invention relates to compounds of the general formula (1.6.1), (1.6.2), (1.6.3) or (1.6.4)
(1.6.1)
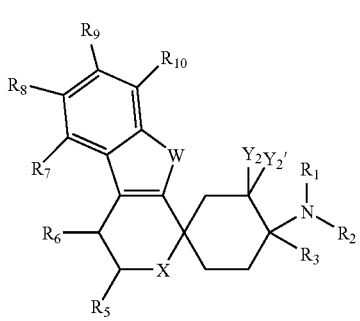

-continued

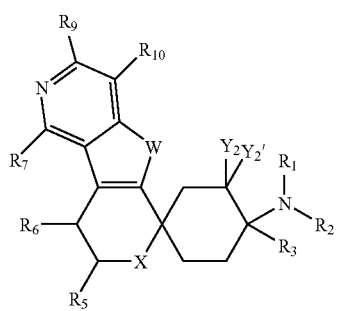
(1.6.2)

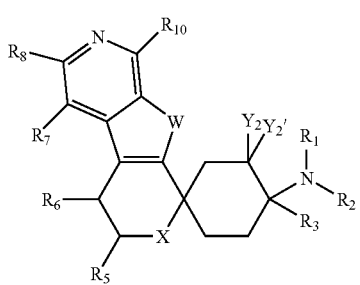
(1.6.3)

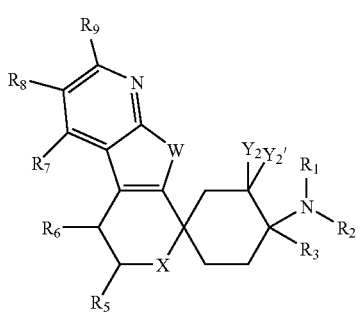
(1.6.4)

A further preferred embodiment of the invention relates to compounds of the general formula (1.7.1), (1.7.2), (1.7.3) or (1.7.4)

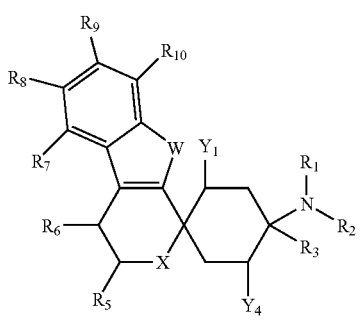
(1.7.1)

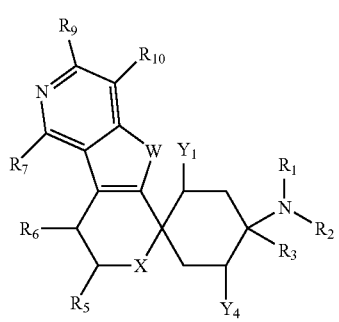
(1.7.2)

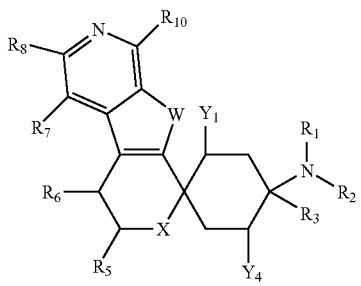
(1.7.3)

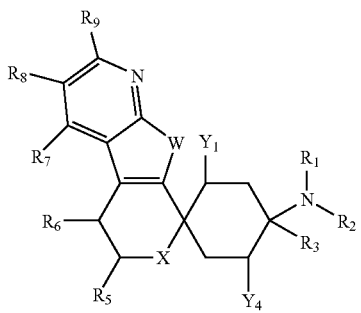
(1.7.4)

Further preferred embodiments of the compounds according to the invention of the general formula (1) have the general formula (2):

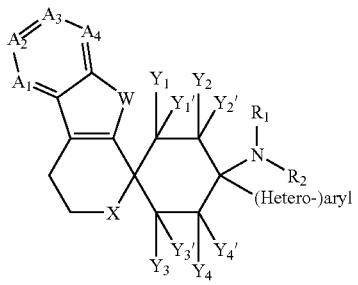
(2)

wherein (hetero)aryl stands for -aryl or -heteroaryl, respectively unsubstituted or mono- or polysubstituted.

Preferred embodiments of the compounds with the general formula (2) have the general formula (2.1), (2.2), (2.3) or (2.4):

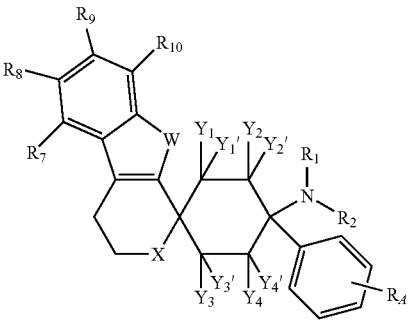
(2.1)

(2.2)
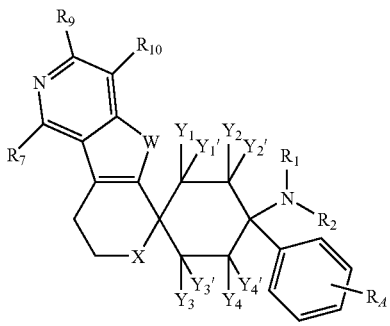

(2.3)
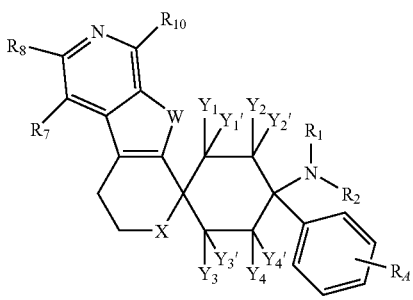

(2.4)
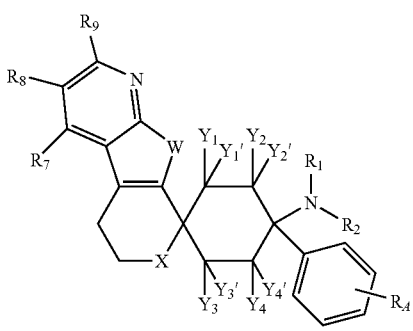

wherein $R_A$ stands for —H, —F, —Cl, —CN or —CH$_3$, preferably —H.

In the compounds of the general formulae (2), (2.1), (2.2), (2.3) and (2.4) W is preferably —NH—.

Particularly preferred embodiments of the compounds of the general formula (2.1) have the general formula (2.1.1) and particularly preferred embodiments of the compounds of the general formula (2.4) have the general formula (2.4.1):

(2.1.1)
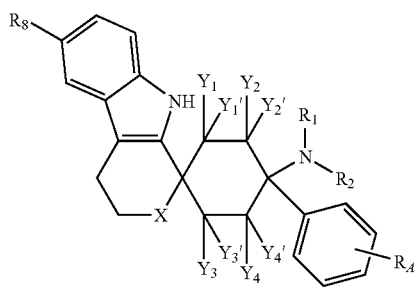

(2.4.1)
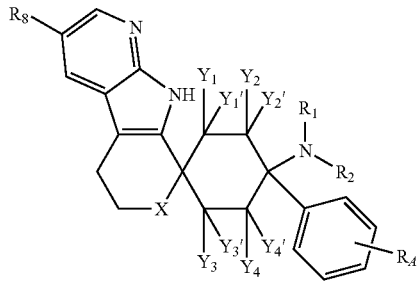

Compounds of the general formula (2.1.1) or (2.1.4?) that are particularly preferred are those,
wherein
X stands for —O— or —NR$_{17}$—, preferably —O— or —NH—;
R$_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;
R$_1$ stands for —CH$_3$;
R$_2$ stands for —H or —CH$_3$;
R$_8$ stands for —H or —F;
R$_{12}$ respectively independently stands for —H, —R$_0$, —OR$_{13}$, or —NR$_{14}$R$_{15}$;
R$_{13}$ respectively independently stands for —H or R$_0$;
R$_{14}$ and R$_{15}$ independently of one another stand for —H or R$_0$; or R$_{14}$ and R$_{15}$ together stand for —CH$_2$CH$_2$OCH$_2$CH$_2$—, —CH$_2$CH$_2$NR$_{16}$CH$_2$CH$_2$— or —(CH$_2$)$_{3-6}$—;
R$_{16}$ stands for —H or —C$_{1-6}$-aliphatic;
R$_{17}$ stands for —H, —R$_0$, —COR$_{12}$ or —S(=O)$_2$R$_{12}$; and
Y$_1$, Y$_1$', Y$_2$, Y$_2$', Y$_3$, Y$_3$', Y$_4$ and Y$_4$' are respectively selected independently of one another from the group comprising —H, —F, —Cl, —CN, —C$_{1-8}$-aliphatic, —C$_{1-8}$-aliphatic-NHC$_{1-8}$-aliphatic, —C$_{1-8}$-aliphatic-N(C$_{1-8}$-aliphatic)$_2$, —S—C$_{1-8}$-aliphatic, —S-aryl, -aryl and —C$_{1-8}$-aliphatic-aryl; on condition that at least one of the residues Y$_1$, Y$_1$', Y$_2$, Y$_2$', Y$_3$, Y$_3$', Y$_4$ and Y$_4$' differs from —H; and
R$_A$ stands for —H, —F, —Cl, —CN or —CH$_3$.

In a preferred embodiment of the compounds according to the invention W is —NR$_4$— and X is —NR$_{17}$—, —O—, —S—, —S(=O)$_{1-2}$— (i.e. —S(=O)— or —S(=O)$_2$—), or —CR$_{18}$R$_{19}$—.

In another preferred embodiment of the compounds according to the invention W is —O— and X is —NR$_{17}$—, —O—, —S—, —S(=O)$_{1-2}$—, or —CR$_{18}$R$_{19}$—.

In another preferred embodiment of the compounds according to the invention W is —S— and X is —NR$_{17}$—, —O—, —S—, —S(=O)$_{1-2}$—, or —CR$_{18}$R$_{19}$—.

It is preferred if Y$_1$, Y$_1$', Y$_2$, Y$_2$', Y$_3$, Y$_3$', Y$_4$ and Y$_4$' are respectively selected independently of one another from the group comprising —H, —F, —Cl, —Br, —I, —CN, —NH$_2$, —NH—C$_{1-6}$-aliphatic, —NH—C$_{3-8}$-cycloaliphatic, —NH—C$_{1-6}$-aliphatic-OH, —N(C$_{1-6}$-aliphatic)$_2$, —N(C$_{3-8}$-cycloaliphatic)$_2$, —N(C$_{1-6}$-aliphatic-OH)$_2$, —NO$_2$, —NH—C$_{1-6}$-aliphatic-C$_{3-8}$-cycloaliphatic, —NH—C$_{1-6}$-aliphatic-aryl, —NH—C$_{1-6}$-aliphatic-heteroaryl, —NH-aryl, —NH-heteroaryl, —SH, —S—C$_{1-6}$-aliphatic, —S—C$_{3-8}$-cycloaliphatic, —S—C$_{1-6}$-aliphatic-C$_{3-8}$-cycloaliphatic, —S—C$_{1-6}$-aliphatic-aryl, —S—C$_{1-6}$-aliphatic-heteroaryl, —S-aryl, —S-heteroaryl, —OH, —O—C$_{1-6}$-aliphatic, —O—C$_{3-8}$-cycloaliphatic, —O—C$_{1-6}$-aliphatic-OH, —O—C$_{1-6}$-aliphatic-C$_{3-8}$-cycloaliphatic, —O—C$_{1-6}$-aliphatic-aryl, —O—C$_{1-6}$-aliphatic-heretoaryl, —O-aryl, —O-heteroaryl, —O—C(=O)C$_{1-6}$-aliphatic, —O—C(=O)C$_{3-8}$-cycloaliphatic, —O—C(=O)C$_{1-6}$-aliphatic-OH, —O—C(=O)C$_{1-6}$-aliphatic-C$_{3-8}$-cycloaliphatic, —O—C(=O)C$_{1-6}$-aliphatic-aryl, —O—C(=O)C$_{1-6}$-aliphatic-heretoaryl, —O—C(=O)aryl, —O—C(=O)heteroaryl, —C$_{1-6}$-aliphatic, —C$_{1-8}$-aliphatic-NHC$_{1-8}$-aliphatic, —C$_{1-8}$-aliphatic-N(C$_{1-8}$-aliphatic)$_2$, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, -aryl, -heteroaryl, —C(=O)C$_{1-6}$-aliphatic, —C(=O)C$_{3-8}$-cycloaliphatic, —C(=O)C$_{1-6}$-aliphatic-C$_{3-8}$-cycloaliphatic, —C(=O)C$_{1-6}$-aliphatic-aryl, —C(=O)C$_{1-6}$-aliphatic-heteroaryl, —C(=O)aryl, —C(=O)heteroaryl, —CO$_2$H, —CO$_2$—C$_{1-6}$-aliphatic, —CO$_2$—C$_{3-8}$-cycloaliphatic, —CO$_2$—C$_{1-6}$-aliphatic-C$_{3-8}$-cycloaliphatic, —CO$_2$—C$_{1-6}$-aliphatic-aryl, —CO$_2$—C$_{1-6}$-aliphatic-heteroaryl, —CO$_2$-aryl, —CO$_2$-heteroaryl; or Y$_1$ and Y$_1$', or Y$_2$ and Y$_2$', or Y$_3$ and Y$_3$', or Y$_4$ and Y$_4$' together stand for =O; on condition that at least one of the residues Y$_1$, Y$_1$', Y$_2$, Y$_2$', Y$_3$, Y$_3$', Y$_4$ and Y$_4$' does not stand for —H.

It is more preferred if Y$_1$, Y$_1$', Y$_2$, Y$_2$', Y$_3$, Y$_3$', Y$_4$ and Y$_4$' are respectively selected independently of one another from the group comprising —H, —F, —Cl, —Br, —I, —CN, —C$_{1-6}$-aliphatic, —C$_{1-6}$-aliphatic-NHC$_{1-6}$-aliphatic, —C$_{1-6}$-aliphatic-N(C$_{1-8}$-aliphatic)$_2$, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, —S—C$_{1-8}$-aliphatic, —S-aryl, -aryl or -heteroaryl.

It is particularly preferred if Y$_1$, Y$_1$', Y$_2$, Y$_2$', Y$_3$, Y$_3$', Y$_4$ and Y$_4$' are respectively selected independently of one another from the group comprising —H, —F, —Cl, —C$_{1-6}$-alkyl, —C$_{2-4}$-alkenyl, —C$_{1-6}$-alkyl-NH—C$_{1-6}$-alkyl, —C$_{1-6}$-alkyl-N(C$_{1-6}$-alkyl)$_2$, -aryl, —C$_{1-6}$-alkyl-aryl, —S—C$_{1-6}$-alkyl and —S-aryl.

In a particularly preferred embodiment one of the residues Y$_1$, Y$_1$', Y$_2$, Y$_2$', Y$_3$, Y$_3$', Y$_4$ and Y$_4$', preferably Y$_1$, Y$_1$', Y$_3$ or Y$_3$', or two of the residues Y$_1$, Y$_1$', Y$_2$, Y$_2$', Y$_3$, Y$_3$', Y$_4$ and Y$_4$' respectively stands/stand for —C$_{1-6}$-aliphatic, preferably —CH$_3$, —CH$_2$CH$_3$, —CH$_2$CH$_2$CH$_3$ or —CH$_2$CH=CH$_2$, and the remaining residues stand for —H.

Preferred representatives are compounds E-1 to E-9, in which X is respectively —O— or —NH—:

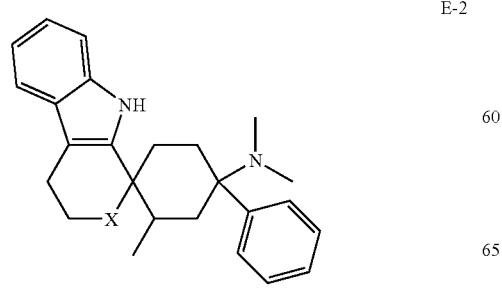

E-1

E-2

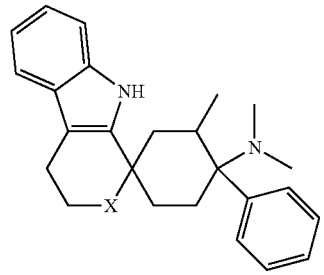

E-3

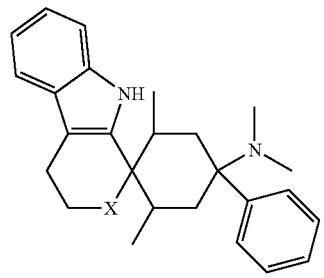

E-4

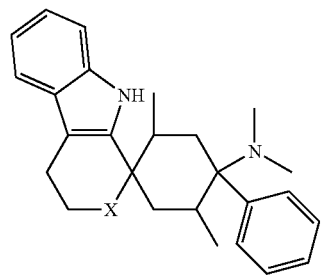

E-5

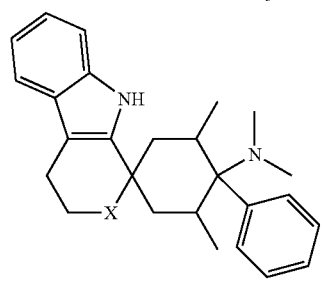

E-6

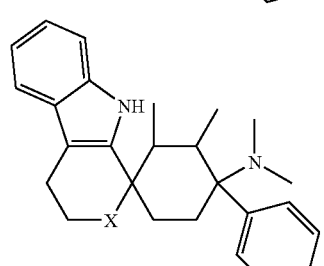

E-7

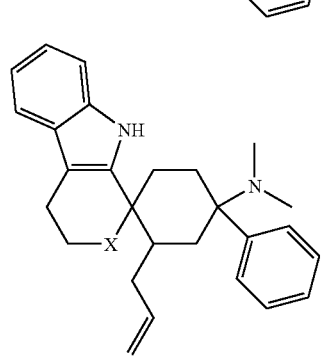

E-8

E-9

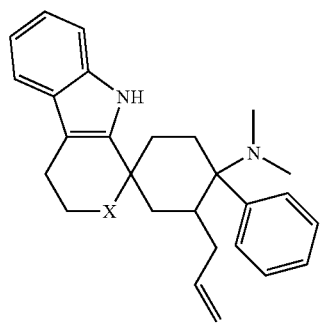

In another particularly preferred embodiment one of the residues $Y_1, Y_1', Y_2, Y_2', Y_3, Y_3', Y_4$ and $Y_4'$, preferably $Y_1, Y_1'$, $Y_3$ or $Y_3'$, stands for -aryl (preferably -phenyl or 4-fluoro-phenyl) or —$C_{1-6}$-aliphatic-aryl (preferably -benzyl or 4-fluoro-benzyl) and the remaining residues stand for —H.

Preferred representatives are the compounds E-10 to E-13, in which X respectively is —O— or —NH—:

E-10

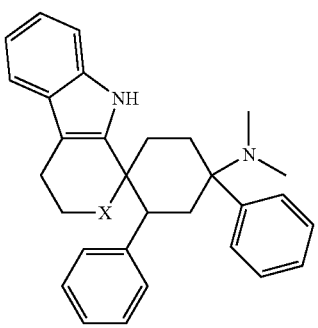

E-11

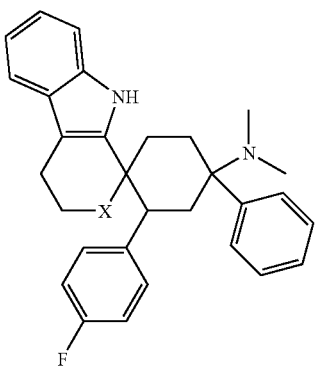

E-12

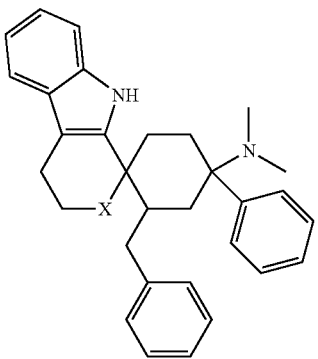

E-13

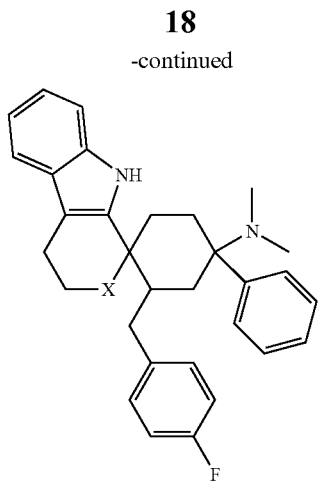

In another particularly preferred embodiment one of the residues $Y_1, Y_1', Y_2, Y_2', Y_3, Y_3', Y_4$ and $Y_4'$, preferably $Y_1, Y_1'$, $Y_3$ or $Y_3'$, or two of the residues $Y_1, Y_1', Y_2, Y_2', Y_3, Y_3', Y_4$ and $Y_4'$ respectively stands/stand for —F and the remaining residues stand for —H.

Preferred representatives are the compounds E-14 to E-17, in which X respectively is —O— or —NH—:

E-14

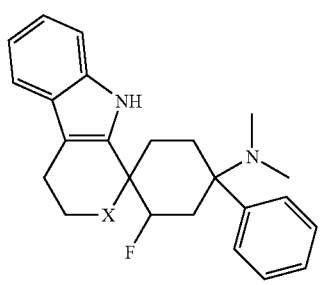

E-15

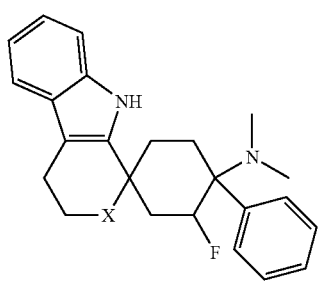

E-16

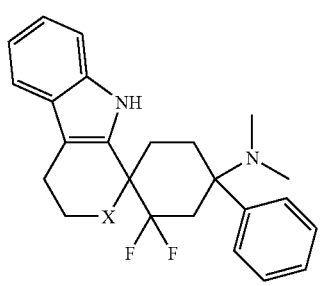

-continued

E-17
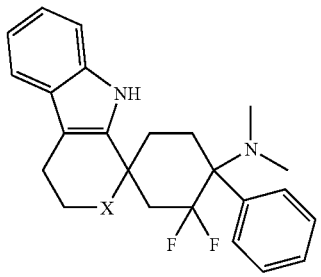

In another particularly preferred embodiment one of the residues $Y_1, Y_1', Y_2, Y_2', Y_3, Y_3', Y_4$ and $Y_4'$, preferably $Y_1, Y_1', Y_3$ or $Y_3'$, stands for —S—$C_{1-6}$-aliphatic (preferably —S—$C_{1-6}$-alkyl), —S-aryl (preferably —S-phenyl) or —$C_{1-6}$-aliphatic-N($C_{1-6}$-aliphatic)$_2$ (preferably —$C_{1-6}$-alkyl-N($C_{1-6}$-alkyl)$_2$) and the remaining residues stand for —H.

Preferred representatives are the compounds E-18 to E-20, in which X respectively is —O— or —NH—:

E-18
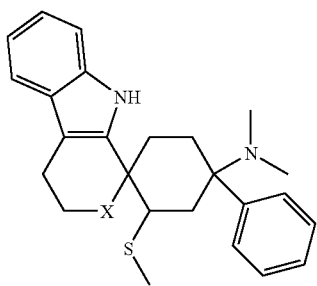

E-19
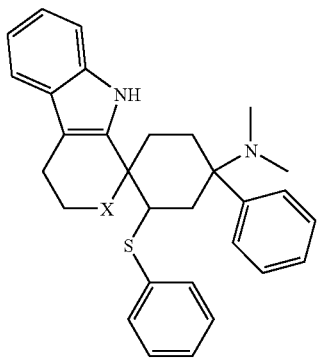

E-20
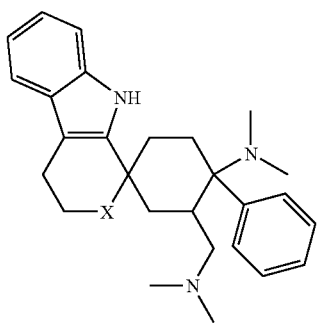

$R_0$, respectively independently, preferably stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl or —$C_{1-8}$-aliphatic-heteroaryl. In this case, —$C_{1-8}$-aliphatic-$C_{3-12}$-cycloaliphatic, —$C_{1-8}$-aliphatic-aryl or —$C_{1-8}$-aliphatic-heteroaryl mean that the residues —$C_{3-12}$-cycloaliphatic, -aryl or -heteroaryl are respectively bonded via a bivalent bridge —$C_{1-8}$-aliphatic-. Preferred examples for —$C_{1-8}$-aliphatic-aryl are —$CH_2$—$C_6H_5$, —$CH_2CH_2$—$C_6H_5$, and —CH=CH—$C_6H_5$.

$R_1$ and $R_2$, independently of one another, preferably stand for —H; —$C_{1-6}$-aliphatic; —$C_{3-8}$-cyclo-aliphatic, —$C_{1-6}$-aliphatic-aryl, —$C_{1-6}$-aliphatic-$C_{3-8}$-cycloaliphatic or —$C_{1-6}$-aliphatic-heteroaryl; or residues $R_1$ and $R_2$ together form a ring and represent —$CH_2CH_2OCH_2CH_2$—, —$CH_2CH_2NR_{11}CH_2CH_2$— or —$(CH_2)_{3-6}$—.

It is more preferred if $R_1$ and $R_2$, independently of one another, stand for —H; —$C_{1-5}$-aliphatic; or residues $R_1$ and $R_2$ together form a ring and represent —$CH_2CH_2OCH_2CH_2$—, —$CH_2CH_2$—$NR_{11}$—$CH_2CH_2$— or —$(CH_2)_{3-6}$—, wherein $R_{11}$ preferably represents —H or —$C_{1-5}$-aliphatic.

Particularly preferred are compounds, in which $R_1$ and $R_2$, independently of one another, stand for —$CH_3$ or —H, wherein $R_1$ and $R_2$ do not represent —H simultaneously; or $R_1$ and $R_2$ form a ring and represent —$(CH_2)_{3-4}$—.

The compounds most especially preferred are those, in which $R_1$ and $R_2$ stand for —$CH_3$.

$R_3$ preferably stands for —$C_{1-8}$-aliphatic, —$C_{3-8}$-cycloaliphatic, -aryl, -heteroaryl; or for -aryl, -heteroaryl or —$C_{3-8}$-cycloaliphatic respectively bonded via a —$C_{1-3}$-aliphatic group.

It is particularly preferred if $R_3$ stands for -ethyl, -propyl, -butyl, -pentyl, -hexyl, -heptyl, -cyclopentyl, -cyclohexyl, -phenyl, -benzyl, -naphthyl, -anthracenyl, -thiophenyl, -benzothio-phenyl, -furyl, -benzofuranyl, -benzodioxolanyl, -indolyl, -indanyl, -benzodioxanyl, -pyrrolyl, -pyridyl, -pyrimidyl or -pyrazinyl, respectively unsubstituted or mono- or polysubstituted; —$C_{5-6}$-cycloaliphatic, -phenyl, -naphthyl, -anthracenyl, -thiophenyl, -benzothiophenyl, -pyridyl, -furyl, -benzofuranyl, -benzodioxolanyl, -indolyl, -indanyl, -benzodioxanyl, -pyrrolyl, -pyrimidyl, -triazolyl or -pyrazinyl, respectively unsubstituted or mono- or polysubstituted, bonded via a saturated, unbranched —$C_{1-3}$-aliphatic group.

It is more preferred if $R_3$ stands for -propyl, -butyl, -pentyl, -hexyl, -phenyl, -furyl, -thiophenyl, -naphthyl, -benzyl, -benzofuranyl, -indolyl, -indanyl, -benzodioxanyl, -benzodioxolanyl, -pyridyl, -pyrimidyl, -pyrazinyl, -triazolyl or -benzothiophenyl, respectively unsubstituted or mono- or polysubstituted; -phenyl, -furyl or -thiophenyl, respectively unsubstituted or mono- or polysubstituted, bonded via a saturated, unbranched —$C_{1-3}$-aliphatic group.

It is further preferred if $R_3$ stands for -propyl, -butyl, -pentyl, -hexyl, -phenyl, -phenethyl, -thiophenyl, -pyridyl, -triazolyl, -benzothiophenyl or -benzyl, respectively substituted or unsubstituted, particularly preferred for -propyl, -3-methoxypropyl, -butyl, -pentyl, -hexyl, -phenyl, -3-methylphenyl, -3-fluorophenyl, -benzo[1,3]-dioxolyl, -thienyl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

It is especially preferred if $R_3$ stands for -butyl, -ethyl, -3-methoxypropyl, -benzothiophenyl, -phenyl, -3-methylphenyl, -3-fluorophenyl, -benzo[1,3]-dioxolyl, -benzyl, -1-methyl-1,2,4-triazolyl, -thienyl or -phenethyl.

It is most preferred if $R_3$ stands for -phenyl, -benzyl or -phenethyl, respectively mono- or polysubstituted on the ring; —$C_{1-5}$-aliphatic, —$C_{4-6}$-cycloaliphatic, -pyridyl, -thienyl, -thiazolyl, -imidazolyl, -1,2,4 triazolyl or -benzimidazolyl, unsubstituted or mono- or polysubstituted.

It is particularly preferred if $R_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstituent with —OH, —OCH$_3$ or —OC$_2$H$_5$, wherein -thienyl, -pyridyl, -thiazolyl, -imidazolyl, -1,2,4-triazolyl and -benzimidazolyl are preferably unsubstituted.

It is particularly preferred if $R_3$ stands for -phenyl, unsubstituted or mono-substituted with —F, —Cl, —CN, —CH$_3$; -thienyl; -ethyl, -n-propyl or -n-butyl, unsubstituted or mono- or polysubstituted with —OCH$_3$, —OH or —OC$_2$H$_5$, in particular with —OCH$_3$.

$R_4$ preferably stands for —H; —C$_{1-6}$-aliphatic, -aryl, -heteroaryl, —C$_{1-6}$-aliphatic-aryl, —C$_{1-6}$-aliphatic-heteroaryl or —C$_{1-6}$-aliphatic-cycloaliphatic, —COR$_{12}$ or —SO$_2$R$_{12}$.

It is particularly preferred if $R_4$ stands for —H.

$R_5$ preferably stands for =O; —H; —COOR$_{13}$, —CONR$_{13}$, —OR$_{13}$, —C$_{1-6}$-aliphatic, C$_{3-8}$-cycloaliphatic, aryl-, or heteroaryl, or aryl, C$_{3-8}$-cycloaliphatic or heteroaryl respectively bonded via C$_{1-3}$-aliphatic.

$R_6$ preferably stands for —H, —F, —Cl, —NO$_2$, —CF$_3$, —OR$_{13}$, —SR$_{13}$, —SO$_2$R$_{13}$, —SO$_2$OR$_{13}$, —CN, —COOR$_{13}$, —NR$_{14}$R$_{15}$, —C$_{1-5}$-aliphatic, —C$_{3-8}$-cycloaliphatic, -aryl- or heteroaryl; or -aryl, —C$_{3-8}$-cycloaliphatic or -heteroaryl respectively bonded via C$_{1-3}$-aliphatic; or $R_5$ and $R_6$ preferably jointly represent —(CH$_2$)$_n$— with n=2, 3, 4, 5 or 6, wherein individual hydrogen atoms can also be replaced by —F, —Cl, —Br, —I, —NO$_2$, —CF$_3$, —OR$_{13}$, —CN or —C$_{1-5}$-aliphatic.

Moreover, $R_5$ preferably stands for —H, —C$_{1-5}$-aliphatic or —COOR$_{13}$. It is particularly preferred if $R_5$ stands for —CH$_3$, —CH$_2$OH, —COOH or —COOCH$_3$. It is most particularly preferred if $R_5$ stands for —H.

Compounds, in which $R_6$ stands for —H, —C$_{1-5}$-aliphatic, -aryl or -aryl bonded via a —C$_{1-3}$-aliphatic group (bridge), are also preferred. It is particularly preferred if $R_6$ stands for —H, —CH$_3$, -phenyl or -benzyl. It is most particularly preferred if $R_6$ stands for —H.

$R_7$, $R_8$, $R_9$ and $R_{10}$, respectively independently of one another, preferably stand for —H, —F, —Cl, —Br, —I, —NO$_2$, —CF$_3$, —OR$_{13}$, —SR$_{13}$, —SO$_2$R$_{13}$, —SO$_2$OR$_{13}$, —CN, —COOR$_{13}$, —NR$_{14}$R$_{15}$; —C$_{1-5}$-aliphatic, —C$_{3-8}$-cycloaliphatic; -aryl or -heteroaryl; or -aryl, —C$_{3-8}$-cycloaliphatic or -heteroaryl respectively bonded via —C$_{1-3}$-aliphatic.

It is more preferred if $R_7$, $R_8$, $R_9$ and $R_{10}$, respectively independently of one another, stand for —H, -methyl, -ethyl, -propyl, -butyl, -pyridyl, —O-benzyl, —F, —Cl, —Br, —I, —CF$_3$, —OH, —OCH$_3$, —NH$_2$, —COOH, —CO—OCH$_3$, —NHCH$_3$, —N(CH$_3$)$_2$ or —NO$_2$.

It is particularly preferred if $R_7$, $R_8$, $R_9$ and $R_{10}$, respectively independently of one another, stand for —H, —F, —OH, —CH$_3$, —Cl, —OCH$_3$, —Br or —NO$_2$.

In a preferred embodiment $R_7$, $R_8$, $R_9$ and $R_{10}$ stand for —H.

In another preferred embodiment three of the residues $R_7$, $R_8$, $R_9$ and $R_{10}$ stand for —H and the remaining residue, preferably $R_8$ or $R_9$, differs from —H, preferably —F, —Cl, —OH or —OCH$_3$.

In another preferred embodiment two of the residues $R_7$, $R_8$, $R_9$ and $R_{10}$ stand for —H and the two remaining residues differ from —H.

$R_{11}$ preferably stands for —H, —C$_{1-5}$-aliphatic, —C$_{3-8}$-cycloaliphatic, -aryl, -heteroaryl, —C$_{1-6}$-aliphatic-aryl, —C$_{1-6}$-aliphatic-C$_{3-8}$-cycloaliphatic, —C$_{1-6}$-aliphatic-heteroaryl, —C(=O)aryl, —C(=O)heteroaryl, or —C(=O)C$_{1-6}$-aliphatic.

$R_{12}$ preferably stands for —H, —C$_{1-5}$-aliphatic, —C$_{3-8}$-cycloaliphatic, -aryl- or -heteroaryl, or -aryl, —C$_{3-8}$-cycloaliphatic or -heteroaryl respectively bonded via —C$_{1-3}$-aliphatic, or for —OR$_{13}$ or —NR$_{14}$R$_{15}$. It is particularly preferred if $R_{12}$ is -aryl, preferably phenyl, bonded via —C$_2$-aliphatic, preferably via —CH$_2$CH$_2$— or —CH=CH—.

$R_{13}$ preferably stands for —H, —C$_{1-5}$-aliphatic, —C$_{3-8}$-cycloaliphatic, -aryl or -heteroaryl; or -aryl, —C$_{3-8}$-cycloaliphatic or -heteroaryl respectively bonded via —C$_{1-3}$-aliphatic.

$R_{14}$ and $R_{15}$, independently of one another, preferably stand for —H, —C$_{1-5}$-aliphatic, —C$_{3-8}$-cycloaliphatic, -aryl or -heteroaryl; or -aryl, —C$_{3-8}$-cycloaliphatic or -heteroaryl respectively bonded via —C$_{1-3}$-aliphatic; or $R_{14}$ and $R_{15}$ together form —CH$_2$CH$_2$OCH$_2$CH$_2$—, —CH$_2$CH$_2$N—R$_{16}$CH$_2$CH$_2$— or —(CH$_2$)$_{3-6}$—.

$R_{16}$ preferably stands for —H or —C$_{1-5}$-aliphatic.

$R_{17}$ preferably stands for —H, —R$_0$, (preferably —C$_{1-8}$-aliphatic), —COR$_{12}$ or —SO$_2$R$_{12}$. In a preferred embodiment $R_{17}$ stands for —H or —COR$_0$, more preferred for —H or —CO—C$_{1-8}$-aliphatic-aryl, particularly preferred for —H or —CO—CH=CH-aryl.

$R_{18}$ and $R_{19}$, respectively independently of one another, preferably stand for —H, —C$_{1-5}$-aliphatic, —C$_{3-8}$-cycloaliphatic, -aryl or -heteroaryl; or -aryl, —C$_{3-8}$-cycloaliphatic or -heteroaryl respectively bonded via —C$_{1-3}$-aliphatic. It is particularly preferred if $R_{18}$ and $R_{19}$ are —H.

For the purposes of the description hydrocarbon residues are divided into aliphatic hydrocarbon residues and aromatic hydrocarbon residues.

Aliphatic hydrocarbon residues are themselves divided into non-cyclic aliphatic hydrocarbon residues (="aliphatic") and cyclic aliphatic hydrocarbon residues, i.e. alicyclic hydrocarbon residues (="cycloaliphatic"). Cycloaliphatic compounds can be monocyclic or multicyclic. Alicyclic hydrocarbon residues ("cycloaliphatic") comprise both pure aliphatic carbocycles and aliphatic heterocycles, i.e.—unless expressly specified—"cycloaliphatic" comprises pure aliphatic carbocycles (e.g. cyclohexyl), pure aliphatic heterocycles (e.g. piperidyl or piperazyl) and also non-aromatic, multicyclic, possibly mixed, systems (e.g. decalinyl, decahydroquinolinyl).

Aromatic hydrocarbons are themselves divided into carbocyclic aromatic hydrocarbons (="aryl") and heterocyclic aromatic hydrocarbons (="heteroaryl").

The classification of multicyclic, at least partially aromatic systems preferably depends on whether at least one aromatic ring of the multicyclic system has at least one heteroatom (usually N, O or S) in the ring. If at least one such heteroatom is present in this ring, this is preferably a "heteroaryl" (even if a further carbocyclic aromatic or non-aromatic ring with or without heteroatom is possibly present as additionally present cycle of the multicyclic system); if such a heteroatom is not present in any of the possibly several aromatic rings of the multicyclic system, then this is preferably "aryl" (even if a ring heteroatom is present in a possibly additionally present non-aromatic cycle of the multicyclic system).

Therefore, the following priority in the classification applies within the cyclic substituents: heteroaryl>aryl>cycloaliphatic.

For the purposes of the description monovalent and multivalent, i.e. bivalent, hydrocarbon residues are not distinguished between conceptually, i.e. depending on the context, "$C_{1-3}$-aliphatic" covers e.g. —$C_{1-3}$-alkyl, —$C_{1-3}$-alkenyl and —$C_{1-3}$-alkinyl, as well as e.g. —$C_{1-3}$-alkylene-, —$C_{1-3}$-alkenylene- and $C_{1-3}$-alkynylene.

Aliphatic is preferably respectively a branched or unbranched, saturated or a mono- or polyunsaturated, unsubstituted or mono- or polysubstituted, aliphatic hydrocarbon residue. Where aliphatic is mono- or polysubstituted, the substituents are selected independently of one another from the group comprising —F, —Cl, —Br, —I, —CN, —$NO_2$, —CHO, =O, —$R_0$, —C(=O)$R_0$, —C(=O)OH, —C(=O)OR$_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)OR$_0$, —OC(=O)$NHR_0$, —OC(=O)N($R_0$)$_2$, —SH, —$SR_0$, —$SO_3H$, —S(=O)$_{1-2}$—$R_0$, —S(=O)$_{1-2}NH_2$, —$NH_2$, —$NHR_0$, —N($R_0$)$_2$, —$N^+(R_0)_3$, —$N^+(R)_2O^-$, —NHC(=O)$R_0$, —NHC(=O)$OR_0$, —NHC(=O)$NH_2$, —NHC(=O)$NHR_0$, —NHC(=O)N($R_0$)$_2$, —Si($R_0$)$_3$, —PO($OR_0$)$_2$. Thus, "aliphatic" covers acyclic saturated or unsaturated hydrocarbon residues that can be branched or straight-chain, i.e. alkanyls, alkenyls and alkinyls. In this case, alkenyls have at least one C=C double bond and alkinyls have at least one C≡C triple bond. Preferred unsubstituted monovalent aliphatics comprise —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, —$CH_2CH_2CH_2$—$CH_2CH_3$ and —$CH_2CH_2CH_2CH_2CH_2CH_3$; but also —CH=$CH_2$, —C≡CH, —$CH_2CH$=$CH_2$, —CH=$CHCH_3$, —$CH_2C$≡CH, —C≡$CCH_3$ and —CH=CHCH=$CH_2$. Preferred unsubstituted bivalent aliphatics comprise —$CH_2$—, —$CH_2CH_2$—, —$CH_2CH(CH_3)$—, —CH($CH_3$)$CH_2$—, —$CH_2CH_2CH_2$—, —CH($CH_3$)$CH_2CH_2$—, —$CH_2CH(CH_3)$—$CH_2$—, —$CH_2CH_2CH(CH_3)$—, —CH($CH_2CH_3$)$CH_2$— and —$CH_2CH_2$—$CH_2CH_2$—; but also —CH=CH—, —C≡C—, —$CH_2CH$=CH—, —CH=$CHCH_2$—, —$CH_2C$≡C— and —C≡$CCH_2$—. Preferred substituted monovalent aliphatics comprise —$CH_2F$, —$CHF_2$, —$CF_3$, —$CH_2CF_3$, —$CF_2CF_3$, —$CH_2OH$, —$CH_2CH_2OH$, —$CH_2CHOHCH_3$, —$CH_2OCH_3$, —$CH_2CH_2OCH_3$ and —$CH_2N(CH_3)_2$. Preferred substituted bivalent aliphatics comprise —$CF_2$—, —$CF_2CF_2$—, —$CH_2CHOH$—, —$CHOHCH_2$— and —$CH_2CHOH$CH$_2$—.-Methyl-, -ethyl-, -n-propyl- and -n-butyl- are particularly preferred.

Cycloaliphatic is preferably respectively a saturated or a mono- or polyunsaturated, unsubstituted or mono- or polysubstituted, aliphatic (i.e. not aromatic), mono- or multicyclic hydrocarbon residue. The number of ring-carbon atoms preferably lies in the specified range (i.e. a "$C_{3-8}$-cycloaliphatic" preferably has 3, 4, 5, 6, 7 or 8 ring-carbon atoms). For the purposes of the description "$C_{3-8}$-cycloaliphatic" is preferably a cyclic hydrocarbon with 3, 4, 5, 6, 7 or 8 ring-carbon atoms, saturated or unsaturated, but not aromatic, wherein possibly one or two carbon atoms are replaced independently of one another by a heteroatom S, N or O. Where cycloalkyl is mono- or polysubstituted, the substituents are selected independently of one another from the group comprising —F, —Cl, —Br, —I, —CN, —$NO_2$, —CHO, =O, —$R_0$, —C(=O)$R_0$, —C(=O)OH, —C(=O)OR$_0$, —C(=O)$NH_2$, —C(=O)$NHR_0$, —C(=O)N($R_0$)$_2$, —OH, —$OR_0$, —OC(=O)H, —OC(=O)$R_0$, —OC(=O)$OR_0$, —OC(=O)$NHR_0$, —OC(=O)—N($R_0$)$_2$, —SH, —$SR_0$, —$SO_3H$, —S(=O)$_{1-2}$—$R_0$, —S(=O)$_{1-2}NH_2$, —$NH_2$, —$NHR_0$, —N($R_0$)$_2$, —$N^+(R_0)_3$, —$N^+(R_0)_2O^-$, —NHC(=O)$R_0$, —NHC(=O)$OR_0$, —NHC(=O)$NH_2$, —NHC(=O)$NHR_0$, —NHC(=O)N($R_0$)$_2$, —Si($R_0$)$_3$, —PO($OR_0$)$_2$. Advantageously, $C_{3-8}$-cycloaliphatic is selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

In association with "aliphatic" or "cycloaliphatic", "mono- or polysubstituted" is preferably understood to mean the mono- or polysubstitution, e.g. the mono-, di-, tri- or 4-substitution, of one or more hydrogen atoms by —F, —Cl, —Br, —I, —OH, —$OC_{1-6}$-alkyl, —OC(=O)$C_{1-6}$-alkyl, —SH, —$NH_2$, —$NHC_{1-6}$-alkyl, —N($C_{1-6}$-alkyl)$_2$, —C(=O)OC$_{1-6}$-alkyl or —C(=O)OH. Particularly preferred substituents are —F, —Cl, —OH, —SH, —$NH_2$ and —C(=O)OH.

Polysubstituted residues are understood to be those residues that are polysubstituted, e.g. twice or three times either at different or at the same atoms, e.g. three times at the same C-atom, as in the case of —$CF_3$ or —$CH_2CF_3$, or at different sites, as in the case of —CH(OH)—CH=CH—$CHCl_2$. The polysubstitution can occur with the same or with different substituents. A substituent may also be substituted itself. Thus, -Oaliphatic also covers —$OCH_2CH_2O$—$CH_2CH_2OH$, amongst others. It is preferred if aliphatic or cycloaliphatic is substituted with —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —N($CH_3$)$_2$. It is most particularly preferred if aliphatic or cycloaliphatic is substituted with —OH, —$OCH_3$ or —$OC_2H_5$.

Aryl preferably respectively independently stands for a carbocyclic ring system with at least one aromatic ring, but without heteroatoms in this ring, wherein the aryl residues can possibly be condensed with further saturated, (partially) unsaturated or aromatic ring systems and each aryl residue can be present in unsubstituted or mono- or polysubstituted form, wherein the aryl substituents are the same or different and can be in any desired and possible position of the aryl. Preferred aryls are phenyl, naphthyl, anthracenyl, phenanthrenyl, fluoranthenyl, fluorenyl, indanyl and tetralinyl. Phenyl and naphthyl are particularly preferred. Where aryl is mono- or polysubstituted, the aryl substituents can be the same or different and be in any desired and possible position of the aryl, and are selected independently of one another from the group comprising —F, —Cl, —Br, —I, —CN, —$NO_2$, —CHO, =O, —$R_0$, —C(=O)$R_0$, —C(=O)OH, —C(=O)OR$_0$, —C(=O)$NH_2$, —C(=O)$NHR_0$, —C(=O)N($R_0$)$_2$, —OH, —O($CH_2$)$_{1-2}$O—, —$OR_0$, —OC(=O)H, —OC(=O)$R_0$, —OC(=O)$OR_0$, —OC(=O)$NHR_0$, —OC(=O)N($R_0$)$_2$, —SH, —$SR_0$, —$SO_3H$, —S(=O)$_{1-2}$—$R_0$, —S(=O)$_{1-2}NH_2$, —$NH_2$, —$NHR_0$, —N($R_0$)$_2$, —$N^+(R_0)_3$, —$N^+(R_0)_2O^-$, —NHC(=O)$R_0$, —NHC(=O)$OR_0$, —NHC(=O)$NH_2$, —NHC(=O)$NHR_0$, —NHC(=O)N($R_0$)$_2$, —Si($R_0$)$_3$, —PO($OR_0$)$_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Heteroaryl preferably stands for a 5-, 6- or 7-membered cyclic aromatic residue that contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle, the substituents can be the same or different and can be in any desired and possible position of the heteroaryl; and wherein the heterocycle can also be part of a bi- or polycyclic system. "Heteroaryl" is preferably selected from the group comprising pyrrolyl, indolyl, furyl (furanyl), benzofuranyl, thienyl (thiophenyl), benzothienyl, benzothiadiazolyl, benzoxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding can occur via any desirable and possible ring member of the heteroaryl residue. Where heteroaryl is mono- or polysubstituted, the heteroaryl substituents can be the same or different and can be in any desirable and possible position of the heteroaryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NH—C(=O)R$_0$, —NHC(=O)OR$_0$, —NHC(=O)NH$_2$, —NHC(=O)NHR$_0$, —NHC(=O)N(R$_0$)$_2$, —Si (R$_0$)$_3$, —PO(OR$_0$)$_2$; wherein any N-ring atoms possibly present can be respectively oxidised (N-oxide).

With respect to "aryl" or "heteroaryl", "mono- or polysubstituted" are understood to mean the mono- or polysubstitution, e.g. di-, tri-, 4- or 5-substitution, of one or more hydrogen atoms of the ring system.

Particularly preferred are the (hetero)aryl substituents selected independently of one another from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Particularly preferred substituents are —F, —Cl, —OH, —SH, —NH$_2$ and —C(=O)OH.

The compounds according to the invention can be present in the form of a single stereoisomer or mixture thereof, the free compounds and/or their physiologically compatible salts and/or solvates.

The compounds according to the invention can be chiral or achiral, depending on the substitution pattern.

With respect to the spiro ring system, the compounds according to the invention concern isomers, in which the substitution pattern on the spiro-cyclohexane ring system can also be referred to as cis/trans, Z/E or syn/anti. "Cis-transisomers" are a subgroup of the stereoisomers (configuration isomers).

In a preferred embodiment, the diastereomer excess of the cis-isomer amounts to at least 50% de, more preferred at least 75% de, more preferred at least 90% de, most preferred at least 95% de, and in particular at least 99% de. In another preferred embodiment, the diastereomer excess of the trans-isomer amounts to at least 50% de, more preferred at least 75% de, more preferred at least 90% de, most preferred at least 95% de, and in particular at least 99% de.

Suitable methods for separating the isomers (diastereomers) are known to the person skilled in the art. Column chromatography, preparative HPLC and crystallisation processes can be given as examples.

If the compounds according to the invention are chiral, then they are preferably present as racemate or in concentrated form of an enantiomer. In a preferred embodiment the enantiomer excess(ee) of the S-enantiomer amounts at least 50% ee, more preferred at least 75% ee, more preferred at least 90% ee, most preferred at least 95% ee, and in particular at least 99% ee. In another preferred embodiment, the enantiomer excess (ee) of the R-enantiomer amounts to at least 50% ee, more preferred at least 75% ee, more preferred at least 90% ee, most preferred at least 95% ee, and in particular at least 99% ee.

Suitable methods for separating the enantiomers are known to the person skilled in the art. Preparative HPLC on chiral stationary phases and conversion into diastereomeric intermediates can be given as examples. The conversion into diastereomeric intermediates can occur, for example, as salt formation by means of chiral, enantiomer-pure acids. After separation of the diastereomers thus formed, the salt can then be converted into the free base or another salt again.

Unless expressly specified, each reference to the compounds according to the invention covers all isomers (e.g. stereoisomers, diastereomers, enantiomers) in any desired mixture ratio.

Unless expressly specified, each reference to the compounds according to the invention covers the free compounds (i.e. the forms that are not present in the form of salt) and all physiologically compatible salts.

For the purposes of the description, physiologically compatible salts of the compounds according to the invention are present as salts with anions or acids of the respective compound with inorganic or organic acids, which are physiologically compatible—in particular on application in humans and/or mammals.

Examples of physiologically compatible salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxo-proline, hexane-1-sulphonic acid, nicotinic acid, 2-, 3- or 4-aminobenzoic acid, 2,4,6-trimethyl benzoic acid, α-liponic acid, acetylglycine, acetylsalicylic acid, hippuric acid and/or aspartic acid. The hydrochloride, citrate and hemicitrate are particularly preferred.

Physiologically compatible salts with cations or bases are salts of the respective compound—as anion with at least one, preferably inorganic, cation, which are physiologically compatible—in particular on application in humans and/or mammals. Particularly preferred are the salts of the alkali and earth alkali metals, also ammonium salts, but in particular (mono-) or (di-) sodium, (mono-) or (di-) potassium, magnesium or calcium salts.

The compounds according to the invention are defined by substituents, e.g. by R$_1$, R$_2$ and R$_3$ (substituents of the first generation), which are themselves possibly substituted (substituents of the second generation). Depending on the definition, these substituents of the substituents can themselves be substituted again (substituents of the third generation). If, for example, Y$_1$=—R$_0$, wherein —R$_0$=—C$_{1-8}$-aliphatic (substituent of the first generation), then —C$_{1-8}$-aliphatic can itself be substituted, e.g. with —OR$_0$, wherein R$_0$=-aryl (substituent of the second generation). This gives the functional group —C$_{1-8}$-aliphatic-Oaryl. -Aryl can then in turn be substituted again, e.g. with —Cl (substituent of the third generation). This then gives overall the functional group —C$_{1-8}$-aliphatic-Oaryl-Cl.

In a preferred embodiment, the substituents of the third generation cannot be substituted again, i.e. there are then no substituents of the fourth generation.

In another preferred embodiment, the substituents of the second generation cannot be substituted again, i.e. there are then already no substituents of the third generation. In other words, in this embodiment the functional groups for R$_0$ to R$_{19}$ can possibly be respectively substituted, but the respective substituents cannot then themselves be substituted again.

In another preferred embodiment, the substituents of the first generation can not be substituted again, i.e. there are then neither substituents of the second generation nor substituents of the third generation. In other words, in this embodiment the functional groups for R$_0$ to R$_{19}$ are not respectively substituted.

Compounds are preferred, wherein "aliphatic substituted" or "cycloaliphatic substituted" means aliphatic or cycloaliphatic substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; and "aryl substituted" or "heteroaryl substituted" means aryl or heteroaryl substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, in the form of the racemate; the enantiomers, diastereomers, mixtures of the enantiomers or diastereomers or a single enantiomer or diastereomer; the bases and/or salts of physiologically compatible salts or cations.

For a preferred embodiment of the compounds according to the invention, it applies that R$_1$ and R$_2$ jointly form a ring and stand for —CH$_2$CH$_2$CH$_2$— or —CH$_2$CH$_2$CH$_2$CH$_2$—. Particularly preferred are compounds, in which R$_1$ and R$_2$ form a ring and jointly represent —CH$_2$CH$_2$CH$_2$—.

Moreover, compounds are also preferred, in which R$_3$ stands for phenyl, benzyl or phenethyl, respectively unsubstituted or mono- or polysubstituted on the ring; —C$_{1-5}$-alkyl, unsubstituted or mono- or polysubstituted; —C$_{4-6}$-cycloalkyl, unsubstituted or mono- or polysubstituted; -pyridyl, -thienyl, -thiazolyl, -imidazolyl, -1,2,4 triazolyl or -benzimidazolyl, unsubstituted or mono- or polysubstituted.

Particularly preferred are compounds, in which R$_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstituted with —OH, —OCH$_3$ or —OC$_2$H$_5$, wherein -thienyl, -pyridyl, -thiazolyl, -imidazolyl, -1,2,4 triazolyl and -benzimidazolyl are preferably unsubstituted; in particular -phenyl, unsubstituted or mono-substituted with —F, —Cl, —CN, —CH$_3$; -thienyl; -ethyl, -n-propyl or -n-butyl, unsubstituted or mono- or polysubstituted with —OCH$_3$, —OH or —OC$_2$H$_5$, in particular with —OCH$_3$.

For a preferred embodiment of the compounds according to the invention, it applies that R$_5$ stands for —H, —CH$_3$, —COOH, —COOCH$_3$, —CH$_2$O-phenyl, wherein the phenyl residue can be substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, or for —CH$_2$OH. Particularly preferred are compounds, in which R$_5$ stands for H.

Also particularly preferred are compounds, in which R$_6$ can represent —H; -methyl, -ethyl, —CF$_3$, -benzyl or -phenyl, wherein the benzyl or phenyl residue can be substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. Particularly preferred are spirocyclic cyclohexane derivatives, in which R$_6$ represents H.

Additionally preferred are compounds, in which R$_7$, R$_8$, R$_9$ and R$_{10}$ independently of one another represent —H; —C$_{1-5}$-Alkyl, branched or unbranched, unsubstituted or mono- or polysubstituted; —F, —Cl, —Br, —I, —CF$_3$, —OH, —OCH$_3$, —NH$_2$, —COOH, —COOCH$_3$, —NHCH$_3$, -thienyl, -pyrimidinyl, -pyridyl, —N(CH$_3$)$_2$ or —NO$_2$; preferably one of the residues R$_7$, R$_8$, R$_9$ and R$_{10}$ stands for —H; —C$_{1-5}$-alkyl, branched or unbranched, unsubstituted or mono- or polysubstituted; for —F, —Cl, —Br, —I, —OH, —OCH$_3$, —COOH, —COOCH$_3$, —NH$_2$, —NHCH$_3$ or —N(CH$_3$)$_2$ or —NO$_2$, whereas the remaining residues are —H; or two of the residues R$_7$, R$_8$, R$_9$ and R$_{10}$ independently of one another stand for —H; —C$_{1-5}$-alkyl, branched or unbranched, unsubstituted or mono- or polysubstituted; for —F, —Cl, —Br, —I, —OH, —OCH$_3$, —COOH, —COOCH$_3$, —NH$_2$, —NHCH$_3$ or —N(CH$_3$)$_2$ or —NO$_2$, whereas the remaining residues are —H. Particularly preferred are spirocyclic cyclohexane derivatives, in which R$_7$, R$_8$, R$_9$ and R$_{10}$ independently of one another stand for —H, —F, —OH, —Cl or —OCH$_3$.

Compounds, in which X stands for —O—, are particularly preferred. In addition, compounds, in which X stands for —NR$_{17}$—, are particularly preferred.

Preferred embodiments of the compounds according to the invention of the general formulae (1.2.1), (1.2.4), (1.3.1), (1.3.4), (1.4.1), (1.4.4), (1.5.1), (1.5.4), (1.6.1), (1.6.4), (1.7.1) and (1.7.4) have the general formulae (1.2.1.1), (1.2.1.2), (1.2.4.1), (1.2.4.2), (1.3.1.1), (1.3.1.2), (1.3.4.1), (1.3.4.2), (1.4.1.1), (1.4.1.2), (1.4.4.1), (1.4.4.2), (1.5.1.1), (1.5.1.2), (1.5.4.1), (1.5.4.2), (1.6.1.1), (1.6.1.2), (1.6.4.1), (1.6.4.2), (1.7.1.1), (1.7.1.2), (1.7.4.1) and (1.7.4.2):

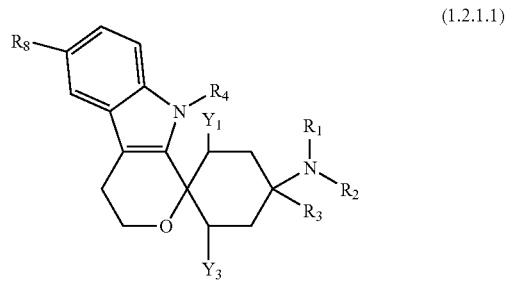

(1.2.1.1)

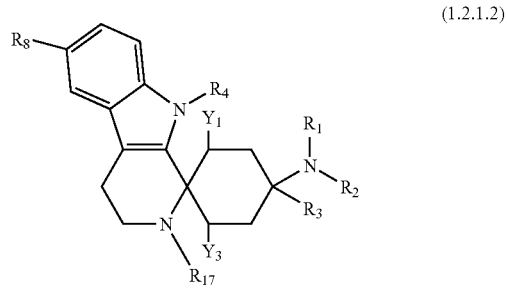

(1.2.1.2)

(1.2.4.1)
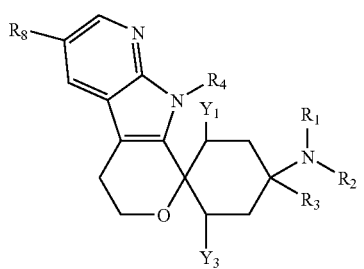
(1.2.4.2)
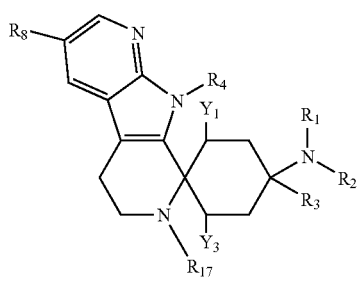
(1.3.1.1)
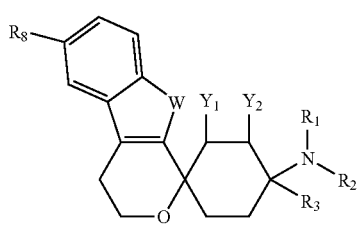
(1.3.1.2)
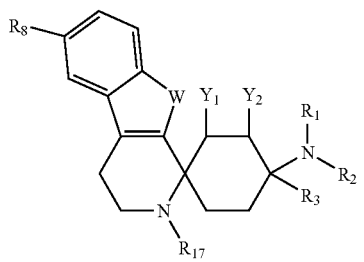
(1.3.4.1)
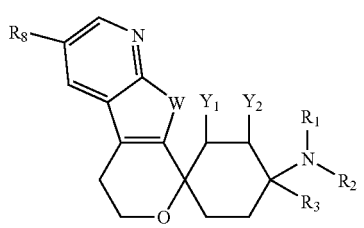
(1.3.4.2)
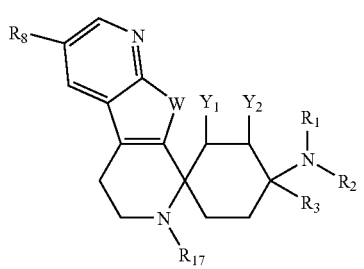
(1.4.1.1)
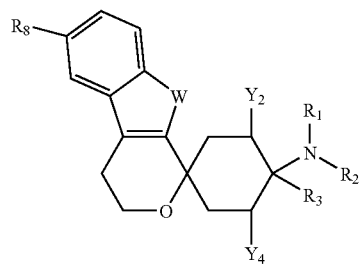
(1.4.1.2)
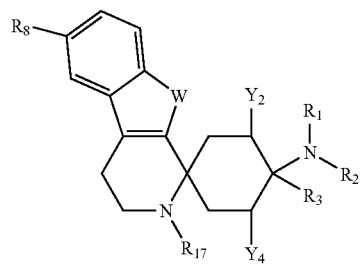
(1.4.4.1)
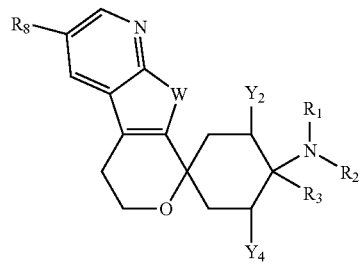
(1.4.4.2)
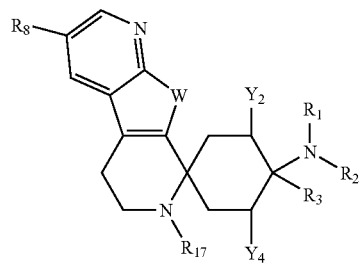
(1.5.1.1)
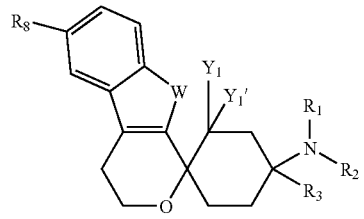
(1.5.1.2)
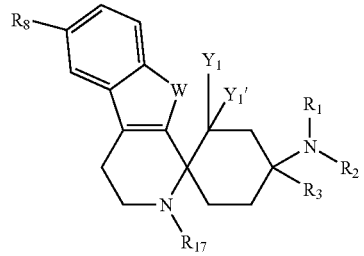

(1.5.4.1)
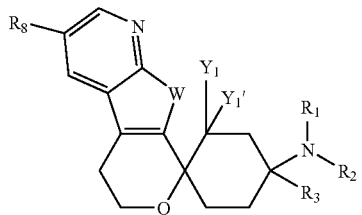

(1.5.4.2)
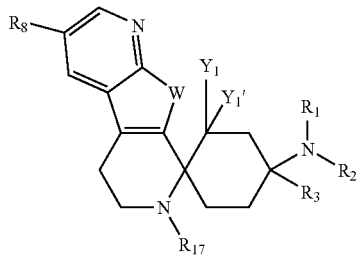

(1.6.1.1)
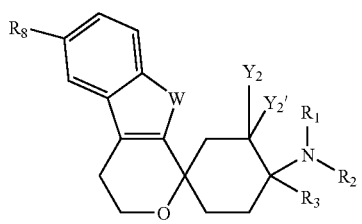

(1.6.1.2)
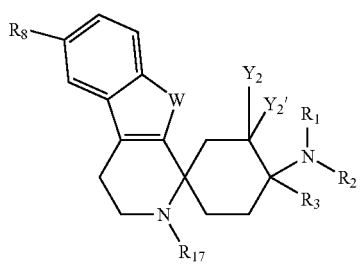

(1.6.4.1)
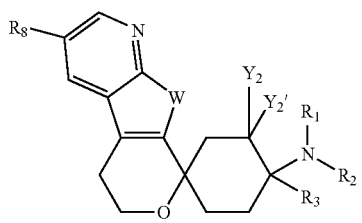

(1.6.4.2)
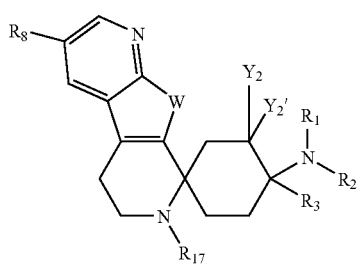

(1.7.1.1)
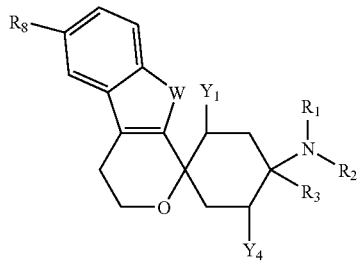

(1.7.1.2)
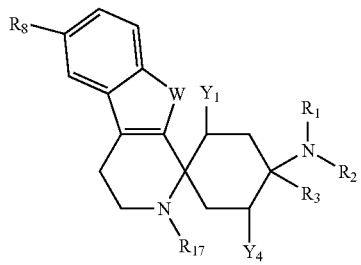

(1.7.4.1)
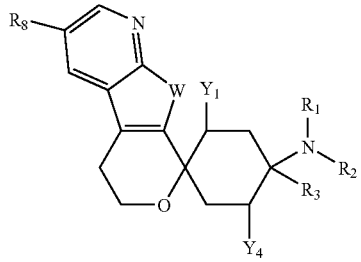

(1.7.4.2)
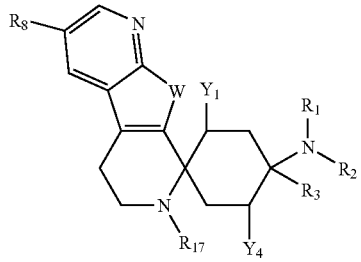

wherein preferably
$R_1$ stands for —$CH_3$;
$R_2$ stands for —H or —$CH_3$;
$R_3$ stands for -phenyl, unsubstituted or mono- or polysubstituted with —F, —Cl, —CN or —$CH_3$;
$R_4$ stands for —H or —$COR_{12}$;
$R_8$ stands for —H or —F;
$R_{17}$ stands for —H or —$COR_{12}$; and
$Y_1$, $Y_1'$, $Y_2$, $Y_2'$, $Y_3$ and $Y_4$, where present, are respectively selected independently of one another from the group comprising —H, —F, —Cl, —Br, —I, —CN, —$C_{1-6}$-aliphatic, —$C_{1-6}$-aliphatic-NH$C_{1-6}$-aliphatic, —$C_{1-6}$-aliphatic-N($C_{1-8}$-aliphatic)$_2$, —$C_{3-8}$-cycloaliphatic, —$C_{1-6}$-aliphatic-$C_{3-8}$-cycloaliphatic, —$C_{1-6}$-aliphatic-aryl, —$C_{1-6}$-aliphatic-heteroaryl, —S—$C_{1-8}$-aliphatic, —S-aryl, -aryl and -heteroaryl; on condition that at least one of the residues $Y_1$, $Y_1'$, $Y_2$, $Y_2'$, $Y_3$ and $Y_4$ differs from —H.

Compounds from the following group are most particularly preferred:
(±)-N,N,2-trimethyl-4-phenyl-4',9'-dihydro-3'H-spiro[cyclohexane-1,1'-pyrano[3,4-b]indole]-4-amine; 2-hydroxypropane-1,2,3-tricarboxylate;

(±)-N,N,2-trimethyl-4-phenyl-4',9'-dihydro-3'H-spiro[cyclohexane-1,1'-pyrano[3,4-b]indole]-4-amine; 2-hydroxypropane-1,2,3-tricarboxylate;

(±)-2-methyl-4-(dimethylamino)1-4-phenyl-spiro[cyclohexane-1,8'-(5,6,8,9-tetra-hydro-pyrano[3,4-b]-7-azaindole)]; 2-hydroxypropane-1,2,3-tricarboxylate;

(±)-2-benzyl-N,N-dimethyl-4-phenyl-4',9'-dihydro-3'H-spiro[cyclohexane-1,1'-pyrano[3,4-b]indole]-4-amine;

(±)-2-benzyl-N,N-dimethyl-4-phenyl-2',3',4',9'-tetrahydrospiro[cyclohexane-1,1'-pyrido[3,4-b]indole]-4-amine; 2-hydroxypropane-1,2,3-tricarboxylate;

(±)-2-(3-fluorobenzyl)-N,N-dimethyl-4-phenyl-4',9'-dihydro-3'H-spiro[cyclohexane-1,1'-pyrano[3,4-b]indole]-4-amine;

N,N,3,5-tetramethyl-4-phenyl-4',9'-dihydro-3'H-spiro[cyclohexane-1,1'-pyrano[3,4-b]indole]-4-amine;

N,N,2,6-tetramethyl-4-phenyl-4',9'-dihydro-3'H-spiro[cyclohexane-1,1'-pyrano[3,4-b]indole]-4-amine;

N,N,2,5-tetramethyl-4-phenyl-4',9'-dihydro-3'H-spiro[cyclohexane-1,1'-pyrano[3,4-b]indole]-4-amine;

2-benzyl-N,N-dimethyl-4-phenyl-4',9'-dihydro-3'H-spiro[cyclohexane-1,1'-pyrano-[3,4-b]indole]-4-amine;

2-(4-fluorobenzyl)-N,N-dimethyl-4-phenyl-4',9'-dihydro-3'H-spiro[cyclohexane-1,1'-pyrano[3,4-b]indole]-4-amine;

N,N,2,3-tetramethyl-4-phenyl-4',9'-dihydro-3'H-spiro[cyclohexane-1,1'-pyrano[3,4-b]indole]-4-amine;

N,N-dimethyl-3,4-diphenyl-4',9'-dihydro-3'H-spiro[cyclohexane-1,1'-pyrano[3,4-b]indole]-4-amine;

2-(4-fluorophenyl)-N,N-dimethyl-4-phenyl-4',9'-dihydro-3'H-spiro[cyclohexane-1,1'-pyrano[3,4-b]indole]-4-amine;

3-((dimethylamino)methyl)-N,N-dimethyl-4-phenyl-4',9'-dihydro-3'H-spiro[cyclohexane-1,1'-pyrano[3,4-b]indole]-4-amine;

N,N,3-trimethyl-4-phenyl-4',9'-dihydro-3'H-spiro[cyclohexane-1,1'-pyrano[3,4-b]indole]-4-amine;

3-fluoro-N,N-dimethyl-4-phenyl-4',9'-dihydro-3'H-spiro[cyclohexane-1,1'-pyrano[3,4-b]indole]-4-amine;

2-fluoro-N,N-dimethyl-4-phenyl-4',9'-dihydro-3'H-spiro[cyclohexane-1,1'-pyrano[3,4-b]indole]-4-amine;

N,N-dimethyl-2-(methylthio)-4-phenyl-4',9'-dihydro-3'H-spiro[cyclohexane-1,1'-pyrano[3,4-b]indole]-4-amine;

N,N-dimethyl-4-phenyl-2-(phenylthio)-4',9'-dihydro-3'H-spiro[cyclohexane-1,1'-pyrano[3,4-b]indole]-4-amine;

3,3-difluoro-N,N-dimethyl-4-phenyl-4',9'-dihydro-3'H-spiro[cyclohexane-1,1'-pyrano-[3,4-b]indole]-4-amine;

2,2-difluoro-N,N-dimethyl-4-phenyl-4',9'-dihydro-3'H-spiro[cyclohexane-1,1'-pyrano-[3,4-b]indole]-4-amine;

2-allyl-N,N-dimethyl-4-phenyl-4',9'-dihydro-3'H-spiro[cyclohexane-1,1'-pyrano[3,4-b]indole]-4-amine;

N,N,3,5-tetramethyl-4-phenyl-2',3',4',9'-tetrahydrospiro[cyclohexane-1,1'-pyrido[3,4-b]indole]-4-amine;

N,N,2,6-tetramethyl-4-phenyl-2',3',4',9'-tetrahydrospiro[cyclohexane-1,1'-pyrido[3,4-b]indole]-4-amine;

N,N,2,5-tetramethyl-4-phenyl-2',3',4',9'-tetrahydrospiro[cyclohexane-1,1'-pyrido[3,4-b]indole]-4-amine;

2-benzyl-N,N-dimethyl-4-phenyl-2',3',4',9'-tetrahydrospiro[cyclohexane-1,1'-pyrido-[3,4-b]indole]-4-amine;

2-(4-fluorobenzyl)-N,N-dimethyl-4-phenyl-2',3',4',9'-tetrahydrospiro-[cyclohexane-1,1'-pyrido[3,4-b]indole]-4-amine;

N,N,2,3-tetramethyl-4-phenyl-2',3',4',9'-tetrahydrospiro[cyclohexane-1,1'-pyrido[3,4-b]indole]-4-amine;

N,N-dimethyl-3,4-diphenyl-2',3',4',9'-tetrahydrospiro[cyclohexane-1,1'-pyrido[3,4-b]indole]-4-amine;

2-(4-fluorophenyl)-N,N-dimethyl-4-phenyl-2', 3',4',9'-tetrahydrospiro-[cyclohexane-1,1'-pyrido[3,4-b]indole]-4-amine;

3-((dimethylamino)methyl)-N,N-dimethyl-4-phenyl-2',3',4',9'-tetrahydrospiro[cyclohexane-1,1'-pyrido[3,4-b]indole]-4-amine;

N,N,3-trimethyl-4-phenyl-2',3',4',9'-tetrahydrospiro[cyclohexane-1,1'-pyrido[3,4-b]indole]-4-amine;

3-fluoro-N,N-dimethyl-4-phenyl-2',3',4',9'-tetrahydrospiro[cyclohexane-1,1'-pyrido-[3,4-b]indole]-4-amine;

2-fluoro-N,N-dimethyl-4-phenyl-2',3',4',9'-tetrahydrospiro[cyclohexane-1,1'-pyrido-[3,4-b]indole]-4-amine;

N,N-dimethyl-2-(methylthio)-4-phenyl-2',3',4',9'-tetrahydrospiro[cyclohexane-1,1'-pyrido[3,4-b]indole]-4-amine;

N,N-dimethyl-4-phenyl-2-(phenylthio)-2',3',4',9'-tetrahydrospiro[cyclohexane-1,1'-pyrido[3,4-b]indole]-4-amine;

3,3-difluoro-N,N-dimethyl-4-phenyl-2',3',4',9'-tetrahydrospiro[cyclohexane-1,1'-pyrido[3,4-b]indole]-4-amine;

2,2-difluoro-N,N-dimethyl-4-phenyl-2',3',4',9'-tetrahydrospiro[cyclohexane-1,1'-pyrido[3,4-b]indole]-4-amine;

2-allyl-N,N-dimethyl-4-phenyl-2',3',4',9'-tetrahydrospiro[cyclohexane-1,1'-pyrido[3,4-b]indole]-4-amine;

2-benzyl-6'-fluoro-N,N-dimethyl-4-phenyl-4',9'-dihydro-3'H-spiro-[cyclohexane-1,1'-pyrano[3,4-b]indole]-4-amine;

6'-fluoro-2-(3-fluorobenzyl)-N,N-dimethyl-4-phenyl-4',9'-dihydro-3'H-spiro[cyclohexane-1,1'-pyrano[3,4-b]indole]-4-amine;

2-(3-fluorobenzyl)-N,N-dimethyl-4-phenyl-2',3',4',9'-tetrahydrospiro-[cyclohexane-1,1'-pyrido[3,4-b]indole]-4-amine;

3,6'-difluoro-N,N-dimethyl-4-phenyl-4',9'-dihydro-3'H-spiro[cyclohexane-1,1'-pyrano[3,4-b]indole]-4-amine;

2,6'-difluoro-N,N-dimethyl-4-phenyl-4',9'-dihydro-3'H-spiro[cyclohexane-1,1'-pyrano[3,4-b]indole]-4-amine;

3,3,6'-trifluoro-N,N-dimethyl-4-phenyl-4',9'-dihydro-3'H-spiro[cyclohexane-1,1'-pyrano[3,4-b]indole]-4-amine;

2,2,6'-trifluoro-N,N-dimethyl-4-phenyl-4',9'-dihydro-3'H-spiro[cyclohexane-1,1'-pyrano[3,4-b]indole]-4-amine;

2,6,6'-trifluoro-N,N-dimethyl-4-phenyl-4',9'-dihydro-3'H-spiro[cyclohexane-1,1'-pyrano[3,4-b]indole]-4-amine;

2,2,6'-trifluoro-N-methyl-4-phenyl-4',9'-dihydro-3'H-spiro[cyclohexane-1,1'-pyrano-[3,4-b]indole]-4-amine;

2,6'-difluoro-N-methyl-4-phenyl-4',9'-dihydro-3'H-spiro[cyclohexane-1,1'-pyrano[3,4-b]indole]-4-amine;

2,6,6'-trifluoro-N-methyl-4-phenyl-4',9'-dihydro-3'H-spiro[cyclohexane-1,1'-pyrano-[3,4-b]indole]-4-amine;

3,3,6'-trifluoro-N,N-dimethyl-4-(thiophen-2-yl)-4',9'-dihydro-3'H-spiro[cyclohexane-1,1'-pyrano[3,4-b]indole]-4-amine;

4-butyl-3,3,6'-trifluoro-N,N-dimethyl-4',9'-dihydro-3'H-spiro[cyclohexane-1,1'-pyrano[3,4-b]indole]-4-amine;

2,2,6'-trifluoro-N,N-dimethyl-4-(thiophen-2-yl)-4',9'-dihydro-3'H-spiro[cyclohexane-1,1'-pyrano[3,4-b]indole]-4-amine;

4-butyl-2,2,6'-trifluoro-N,N-dimethyl-4',9'-dihydro-3'H-spiro[cyclohexane-1,1'-pyrano[3,4-b]indole]-4-amine;
2,6,6'-trifluoro-N,N-dimethyl-4-(thiophen-2-yl)-4',9'-dihydro-3'H-spiro-[cyclohexane-1,1'-pyrano[3,4-b]indole]-4-amine;
4-butyl-2,6,6'-trifluoro-N,N-dimethyl-4',9'-dihydro-3'H-spiro[cyclohexane-1,1'-pyrano[3,4-b]indole]-4-amine;
3,6'-difluoro-N,N-dimethyl-4-(thiophen-2-yl)-4',9'-dihydro-3'H-spiro-[cyclohexane-1,1'-pyrano[3,4-b]indole]-4-amine;
4-butyl-3,6'-difluoro-N,N-dimethyl-4',9'-dihydro-3'H-spiro[cyclohexane-1,1'-pyrano-[3,4-b]indole]-4-amine;
2,6'-difluoro-N,N-dimethyl-4-(thiophen-2-yl)-4',9'-dihydro-3'H-spiro-[cyclohexane-1,1'-pyrano[3,4-b]indole]-4-amine;
4-butyl-2,6'-difluoro-N,N-dimethyl-4',9'-dihydro-3'H-spiro[cyclohexane-1,1'-pyrano-[3,4-b]indole]-4-amine;
3,3,6'-trifluoro-4-(3-fluorophenyl)-N,N-dimethyl-2', 3',4',9'-tetrahydrospiro-[cyclohexane-1,1'-pyrido[3,4-b]indole]-4-amine;
2,2,6'-trifluoro-4-(3-fluorophenyl)-N,N-dimethyl-2',3',4',9'-tetrahydrospiro-[cyclohexane-1,1'-pyrido[3,4-b]indole]-4-amine;
3,6'-difluoro-4-(3-fluorophenyl)-N,N-dimethyl-2',3',4',9'-tetrahydrospiro-[cyclohexane-1,1'-pyrido[3,4-b]indole]-4-amine;
2,6'-difluoro-4-(3-fluorophenyl)-N,N-dimethyl-2',3',4',9'-tetrahydrospiro-[cyclohexane-1,1'-pyrido[3,4-b]indole]-4-amine;
2,6,6'-trifluoro-4-(3-fluorophenyl)-N,N-dimethyl-2', 3',4', 9'-tetrahydrospiro-[cyclohexane-1,1'-pyrido[3,4-b]indole]-4-amine;
3,3-difluoro-N,N-dimethyl-4-phenyl-2',3',4',9'-tetrahydrospiro[cyclohexane-1,1'-pyrido[3,4-b]indole]-4-amine;
2,2-difluoro-4-(3-fluorophenyl)-N,N-dimethyl-2',3',4',9'-tetrahydrospiro-[cyclohexane-1,1'-pyrido[3,4-b]indole]-4-amine;
3-fluoro-4-(3-fluorophenyl)-N,N-dimethyl-2',3',4',9'-tetrahydrospiro-[cyclohexane-1,1'-pyrido[3,4-b]indole]-4-amine;
2-fluoro-4-(3-fluorophenyl)-N,N-dimethyl-2',3',4',9'-tetrahydrospiro-[cyclohexane-1,1'-pyrido[3,4-b]indole]-4-amine;
2,6-difluoro-4-(3-fluorophenyl)-N,N-dimethyl-2',3',4',9'-tetrahydrospiro-[cyclohexane-1,1'-pyrido[3,4-b]indole]-4-amine;
(E)-1-(4-(dimethylamino)-3-fluoro-4-(3-fluorophenyl)-3',4'-dihydrospiro-[cyclohexan-1,1'-pyrido[3,4-b]indole]-2'(9'H)-yl)-3-phenylprop-2-en-1-one;
(E)-1-(4-(dimethylamino)-2-fluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-3,3-difluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-2,2-difluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,6-difluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-3,6-difluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,6'-difluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-3,3,6'-trifluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,2,6'-trifluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,6,6'-trifluoro-4-(3-fluorophenyl)-3',4'-dihydrospiro[cyclohexane-1,1'-pyrido[3,4-b]indole]-2'(9'H)-yl)-3-phenylprop-2-en-1-one;
2-methyl-4-(dimethylamino)1-4-phenyl-spiro[cyclohexane-1,8'-(5,6,7,8,9-penta-hydro-pyrido[3,4-b]-7-aza-indole)];
N,N,2-trimethyl-4-phenyl-2',3',4',9'-tetrahydrospiro[cyclohexane-1,1'-pyrido[3,4-b]indole]-4-amine;
2-benzyl-N,N-dimethyl-4-phenyl-2',3',4',9'-tetrahydrospiro[cyclohexane-1,1'-pyrido-[3,4-b]indole]-4-amine; and
2-benzyl-N,N-dimethyl-4-phenyl-2',3',4',9'-tetrahydrospiro[cyclohexane-1,1'-pyrido-[3,4-b]indole]-4-amine;
6'-fluoro-2-(3-fluorobenzyl)-N,N-dimethyl-4-phenyl-4',9'-dihydrospiro-[cyclohexane-1,1'-pyrano-[3,4-b]indole]-4-amine;
2-(3-fluorobenzyl)-N,N-dimethyl-4-phenyl-2',3',4',9'-tetrahydrospiro-[cyclohexane-1,1'-pyrido[3,4-b]indole]-4-amine;
N,N-dimethyl-4-phenyl-2-(phenylthio)-4',9'-dihydro-3'H-spiro-[cyclohexane-1, pyrano[3,4-b]indole]-4-amine;
N,N-dimethyl-4-phenyl-2-(phenylthio)-2',3',4',9'-tetrahydrospiro[cyclohexane-1,1'-pyrido[3,4-b]indole]-4-amine;
2-(3-fluorobenzyl)-N,N-dimethyl-4-phenyl-2',3',4',9'-tetrahydrospiro-[cyclohexane-1,1'-pyrido-[3,4-b]indole]-4-amine;
2-(4-(dimethylamino)-4-phenyl-4',9'-dihydro-3'H-spiro[cyclohexane-1,1'-pyrano[3,4-b]indole]-2-yl)methyl acetate;
2-allyl-N,N-dimethyl-4-phenyl-4',9'-dihydros-3'H-spiro[cyclohexane-1,1'-pyrano[3,4-b]indole]-4-amine;
2-fluoro-N,N-dimethyl-4-phenyl-4',9'-dihydro-3'H-spiro[cyclohexane-1,1'-pyrano[3,4-b]indole]-4-amine;
2-allyl-N,N-dimethyl-4-phenyl-4',9'-dihydros-3'H-spiro[cyclohexane-1,1'-pyrano[3,4-b]indole]-4-amine;
2,6'-difluoro-N,N-dimethyl-4-phenyl-4',9'-dihydro-3'H-spiro[cyclohexane-1,1'-pyrano[3,4-b]indole]-4-amine;
4-(dimethylamino)-4-phenyl-4',9'-dihydro-3'H-spiro[cyclohexane-1,1'-pyrano[3,4-b]indole]-2-yl)methanol;
2,6'-difluoro-N,N-dimethyl-4-phenyl-4',9'-dihydro-3'H-spiro[cyclohexane-1,1'-pyrano[3,4-b]indole]-4-amine;
2-fluoro-N,N-dimethyl-4-phenyl-2',3',4',9'-tetrahydrospiro[cyclohexane-1,1'-pyrido[3,4-b]indole]-4-amine;
2-fluoro-N,N-dimethyl-4-phenyl-2',3',4',9'-tetrahydrospiro[cyclohexane-1,1'-pyrido[3,4-b]indole]-4-amine;
2-(4-(dimethylamino)-4-phenyl-4',9'-dihydro-3'H-spiro[cyclohexane-1,1'-pyrano[3,4-b]indole]-2-yl)ethanol
2-(4-(dimethylamino)-4-phenyl-4',9'-dihydro-3'H-spiro[cyclohexane-1,1'-pyrano[3,4-b]indole]-2-yl)methyl) isoindoline-1,3-dione;
N-((4-(dimethylamino)-4-(3-fluorophenyl)-4',9'-dihydro-3'H-spiro-[cyclohexane-1,1'-pyrano[3,4-b]indole]-2-yl)methyl)-3-phenylcinnamic acid amide;
tert-butyl 2-(2-(4-(dimethylamino)-4-phenyl-4',9'-dihydro-3'H-spiro[cyclohexane-1,1'-pyrano[3,4-b]indole]-2-yl)ethoxy)acetate;

2-(4-(dimethylamino)-4-phenyl-4',9'-dihydro-3'H-spiro [cyclohexane-1,1'-pyrano[3,4-b]indole]-2-yl)acetonitrile or physiologically compatible salts and/or solvates thereof.

The compounds according to the invention act, for example, on the relevant ORL1-receptor in association with different diseases, and therefore they are suitable as pharmaceutical active substance in a medication.

Therefore, the invention additionally relates to medications, which contain at least one compound according to the invention, as well as possibly suitable additives and/or adjuvants and/or possibly further active substances.

Besides at least one compound according to the invention, the medications according to the invention possibly contain suitable additives and/or adjuvants, hence also support materials, fillers, solvents, dilutants, colouring agents and/or binders, and can be administered as liquid medications in the form of injectable solutions, drops or juices, as semisolid medications in the form of granules, tablets, pellets, patches, capsules, plasters/spray plasters or aerosols. The selection of adjuvants etc. as well as the quantities thereof to be used are dependent on whether the medication is to be applied orally, perorally, parenterally, intravenously, intraperitoneally, intradermally, intramuscularly, intranasally, bucally, rectally or locally, e.g. onto the skin, mucous membranes or into the eyes. Preparations in the form of tablets, coated tablets, capsules, granules, drops, juices and syrups are suitable for oral application, solutions, suspensions, readily reconstituted dry preparations as well as sprays are suitable for parenteral, topical and inhalatory application. Compounds according to the invention in a depot, in dissolved form or in a plaster, possibly with the addition of skin-penetration promoters, are suitable preparations for percutaneous application. Preparation forms that may be applied orally or percutaneously can release the compounds according to the invention in a delayed manner. The compounds according to the invention can also be applied in parenteral long-term depot forms such as e.g. implants or implanted pumps. In principle, other additional active substances known to the skilled person can be added to the medications according to the invention.

The amount of active substance to be administered to the patient varies depending on the weight of the patient, on the type of application, the indication and the degree of severity of the disease. Usually, 0.00005 to 50 mg/kg, preferably 0.001 to 0.5 mg/kg, of at least one compound according to the invention are applied.

For all the above-mentioned forms of the medication according to the invention it is particularly preferred if, besides at least one compound according to the invention, the medication also contains a further active substance, in particular an opioid, preferably a strong opioid, in particular morphine, or an anaesthetic, preferably hexobarbital or halothane.

In a preferred form of the medication, a contained compound according to the invention is present in the form of pure diastereomer and/or enantiomer.

The ORL1-receptor was identified in particular in the pain process. Compounds according to the invention can be used accordingly for the production of a medication for the treatment of pain, in particular of acute, neuropathic or chronic pain.

Therefore, the invention additionally relates to the use of a compound according to the invention for the production of a medication for the treatment of pain, in particular of acute, visceral, neuropathic or chronic pain.

The invention further relates to the use of a compound according to the invention for the treatment of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinnitus, pruritus, migraine, hearing impairment, deficient intestinal motility, eating disorders, anorexia, bulimia, mobility disorders, diarrhea, cachexia, urinary incontinence, or as muscle relaxant, anticonvulsive or anaesthetic, or for coadministration in the treatment with an opioid analgesic or with an anaesthetic, for diuresis or anti-natriuresis, anxiolysis, for modulating movement activity, for modulating neurotransmitter release and for treating neuro-degenerative diseases associated therewith, for treating withdrawal symptoms and/or for reducing the addiction potential of opioids.

In this case, it can be preferred in one of the above uses if a used compound is present as a pure diastereomer and/or enantiomer, as a racemate or as non-equimolar or equimolar mixture of the diastereomers and/or enantiomers.

The invention additionally relates to a method for treating, in particular in one of the aforementioned indications, a non-human mammal or human, which or who requires a treatment for pain, in particular chronic pain, by the administration of a therapeutically effective dose of a compound according to the invention or a medication according to the invention.

The invention further relates to a method for producing the compounds according to the invention as outlined in the following description and examples.

a) Derivatisation in the 2, 3, 5 and/or 6 Position of Cyclohexane Dione Ketone Acetals

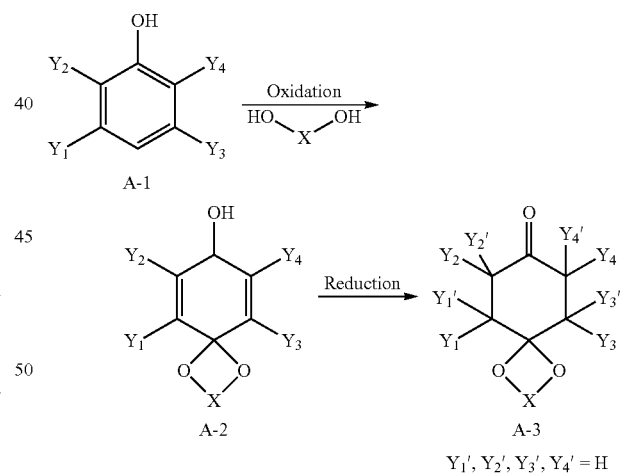

$Y_1', Y_2', Y_3', Y_4' = H$

Substituted cyclohexane dione ketone acetals of the type A-3 can be synthesised from the known A-1 educts using methods known to the person skilled in the art. The oxidation of A-1 phenols by means of hypervalent iodine reagents to form the intermediate A-2 cyclohexadienone ketone acetals is described in the specialist literature (Rose et al., Can. J. Chem., 74, 1996, 1936). Compounds of formula A-3 can then be obtained from the corresponding A-2 ketone acetals using methods known to the skilled person by reduction in a hydrogen atmosphere and in the presence of metal catalysts, e.g. rhodium-based catalysts.

b) Derivatisation in the 2 Position of Cyclohexane Dione Ketone Acetals

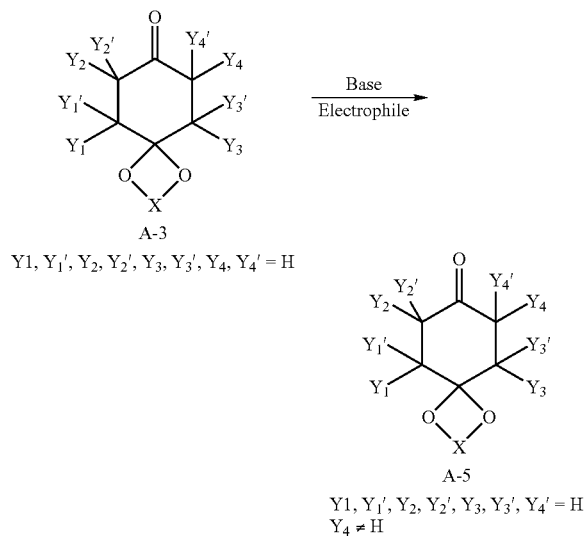

A-3
Y1, Y1', Y2, Y2', Y3, Y3', Y4, Y4' = H

A-5
Y1, Y1', Y2, Y2', Y3, Y3', Y4' = H
Y4 ≠ H

α-substituted cyclohexane dione ketone acetals of the general formula A-5 can be converted by converting the unsubstituted A-3 ketone acetals with a base, e.g. lithium diisopropylamide (LDA), lithium hexamethyl disilazide (LHMDS), potassium hexamethyl disilazide (KHMDS), sodium hydride (NaH), potassium hydride (KH), sodium methanolate (NaOMe), potassium tert-butoxylate (K'OBu), amine bases such as e.g. diethylamine (HNEt$_2$), diisopropylethylamine (Hünig's base), piperidine, pyrrolidine, proline, and with the corresponding electrophiles e.g. of the type Y$_4$—X (with X=e.g. Br, I, OTos, OTf etc. and Y$_4$=e.g. alkyl, benzyl) in organic solvents or solvent mixtures, e.g. dichloromethane (DCM), dichloroethane (DCE), diethyl ether (Et$_2$O), tetrahydrofuran (THF), dimethoxyethane (DME), methanol (MeOH), ethanol (EtOH), dimethylformamide (DMF), dimethylsulphoxide (DMSO) at temperatures between −78° C. and 150° C. Moreover, the generated anion can be converted with corresponding Michael acceptor systems. The introduction of heteroatoms can occur by conversion with disulphur compounds (Y$_4$=S-alkyl or S-aryl), corresponding electrophilic fluorination reagents such as e.g. Selectfluor™ (Y$_4$=F), corresponding electrophilic amination reagents such as e.g. N-alkoxycarbonyl- or N-carboxamido-oxaziridines (Y$_4$=NR$_2$) or corresponding electrophilic hydroxylation reagents such as e.g. oxodiperoxy molybdenum(pyridine)(hexamethyl phosphorus triamide) complex (MoOPH (Y$_4$=OH).

Aldol-type conversions can also occur in acid medium. Moreover, substituents can be introduced by means of a Mannich reaction under acid conditions (camphorsulphonic acid, p-TosOH etc.).

c) Synthesis of Amino Cyclohexanones
(1) Aminonitrile/Triazole Route

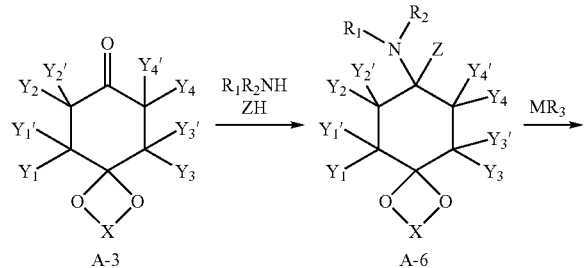

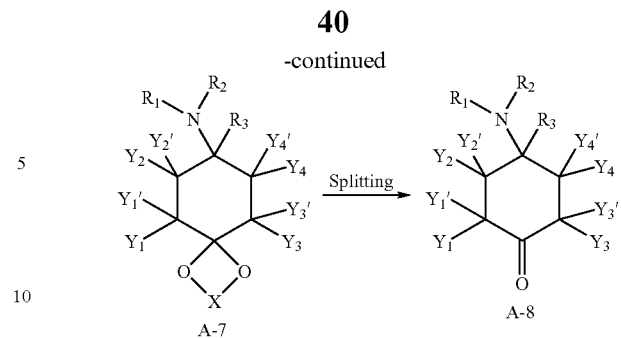

Structures of formula A-6 can be produced by reaction of A-3 ketones with amines and acid Z—H reactants. Suitable Z—H reactants are e.g. hydrogen cyanide, 1,2,3-triazole, benzotriazole or pyrazole.

A particularly preferred route to compounds of A-6 structure is the conversion of ketones with metal cyanides and the corresponding amine in the presence of acid, preferably in an alcohol, at temperatures of −40° to 60° C., preferably at room temperature with alkali metal cyanides in methanol.

A further particularly preferred route to compounds of A-6 structure is the conversion of ketones with 1,2,3-triazole and the corresponding amine in the presence ? under dehydrating conditions, preferably using a water separator at elevated temperature in an inert solvent, or using a molecular sieve or another dehydrating agent. A-6 analogous structures can be introduced in a similar manner with benzotriazole or pyrazole groups instead of triazole groups.

In general, A-7 ketone acetals can also be obtained by substituting suitable Z leaving groups in structures of formula A-6. Suitable leaving groups are preferably cyano groups; 1,2,3-triazol-1-yl groups. Further suitable leaving groups are 1H-benzo[d][1,2,3]triazol-1-yl groups and pyrazol-1-yl groups (Katritzky et al., Synthesis 1989, 66-69).

A particularly preferred route to compounds of A-7 structure is the conversion of A-6 aminonitriles with corresponding organometallic compounds, preferably Grignard compounds, preferably in ethers, preferably at room temperature. The organometallic compounds are either commercially available or can be produced using known methods. A further particularly preferred route to compounds of A-7 structure is the conversion of A-6 aminotriazoles with corresponding organometallic compounds, preferably Grignard compounds, preferably in ethers, preferably at room temperature.

The organometallic compounds are either commercially available or can be produced using methods known from specialist literature.

Compounds of formula A-8 can be released from corresponding A-7 ketone acetals or from their salts by deprotection by means of acids using methods known to the skilled person. In this case, X is selected from the group, alkyl, alkyl/alkylidene/alkylidene substituted with aryl or alkyl (saturated/unsaturated).

(2) Imine Route

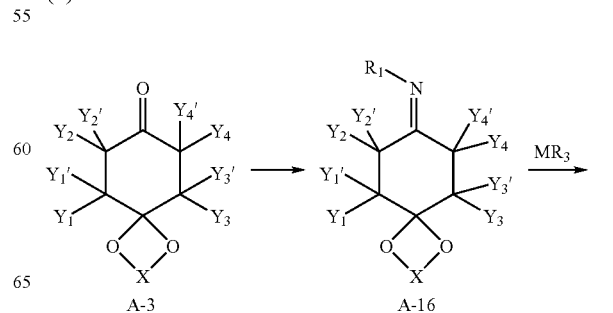

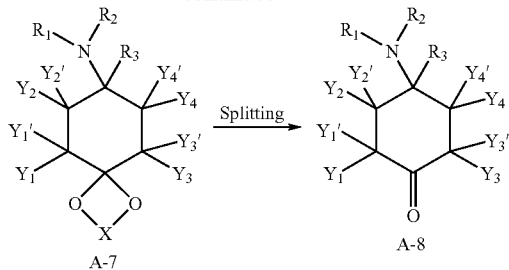

In the imine route, the A-16 imine is synthesised from an A-3 ketone precursor and is converted into the A-7 unit using an MR3 nucleophile and further into A-8. The necessary A-16 imine units can be produced using a method known to the skilled person (Layer, Chem. Rev., 1963, 8, 489-510). Methods known from the specialist literature (e.g. Maddox et al., J. Med. Chem., 1965, 8, 230-235. Kudzma et al., J. Med. Chem., 1989, 32, 2534-2542.) are employed for addition of the MR3 organometallic species to the A-16 imine.

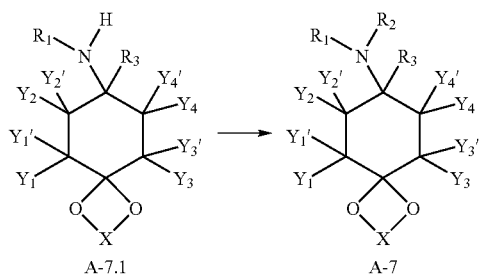

A-7.1 amino acetals with a maximum of one substituent on the nitrogen atom can be converted into corresponding A-7 amino acetals with one or two further substituents (R2≠H) on the nitrogen atom using methods known in principle to the skilled person, e.g. by reductive amination.

d) Derivatisation in the 2 Position of Amino Cyclohexanones

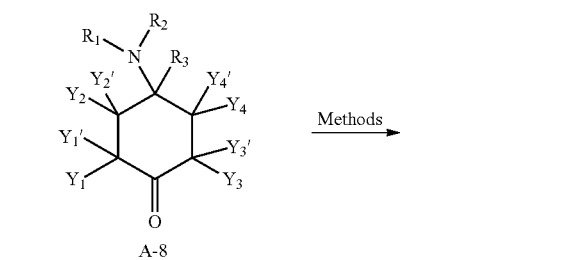

A-8
Y1, Y1', Y2, Y2', Y3, Y3', Y4, Y4' = H

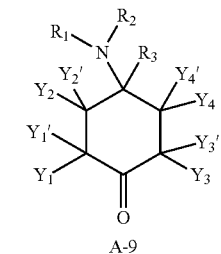

A-9
Y1', Y2, Y2', Y3, Y3', Y4, Y4' = H
Y1 ≠ H

Substituted amino cyclohexanones of type A-9 can be synthesised from the known A-8 educts using methods known to the person skilled in the art.

Method 1:

The α-arylation of A-8 ketones with the corresponding aryl halides, e.g. of type Y$_1$—X (with Y$_1$=aryl/hetaryl and X=Br, I) by palladium catalysis in the presence of suitable phosphine ligands such as e.g. xantphos, is described in the specialist literature (Elliott et al. Bioorg. Med. Chem. Lett.; EN; 16; 11; 2006; 2929; Dirat et al. Tetrahedron Lett.; EN; 47; 8; 2006; 1295.)

Method 2:

α-substituted amino cyclohexanones of type A-9 can be converted by converting unsubstituted A-8 ketone acetals with a base, e.g. lithium diisopropylamide (LDA), lithium hexamethyl disilazide (LHMDS), potassium hexamethyl disilazide (KHMDS), sodium hydride (NaH), potassium hydride (KH), sodium methanolate (NaOMe), potassium tert-butoxylate (K'OBu), amine bases such as e.g. diethylamine (HNEt$_2$), diisopropylethylamine (Hünig's base), piperidine, pyrrolidine, proline, and with the corresponding electrophiles e.g. of the type Y$_4$—X (with X=e.g. Br, I, OTos, OTf etc.) in organic solvents or solvent mixtures, e.g. dichloromethane (DCM), dichloroethane (DCE), diethyl ether (Et$_2$O), tetrahydrofuran (THF), dimethoxyethane (DME), methanol (MeOH), ethanol (EtOH), dimethylformamide (DMF), dimethylsulphoxide (DMSO) at temperatures between −78° C. and 150° C. Moreover, the generated anion can be converted with corresponding Michael acceptor systems. The introduction of heteroatoms can occur by conversion with disulphur compounds (Y$_4$=S-alkyl or S-aryl), corresponding electrophilic fluorination reagents such as e.g. Selectfluor™ (Y$_4$=F), corresponding electrophilic amination reagents such as e.g. N-alkoxycarbonyl- or N-carboxamido-oxaziridines (Y$_4$=NR$_2$) or corresponding electrophilic hydroxylation reagents such as e.g. oxodiperoxy molybdenum(pyridine)(hexamethyl phosphorus triamide) complex (MoOPH (Y$_4$=OH). Aldol-type conversions can also occur in acid medium. Moreover, substituents can be introduced by means of a Mannich reaction under acid conditions (camphorsulphonic acid, p-TosOH etc.).

e) Synthesis of Spirocyclic Compounds of Type A-11 and A-13

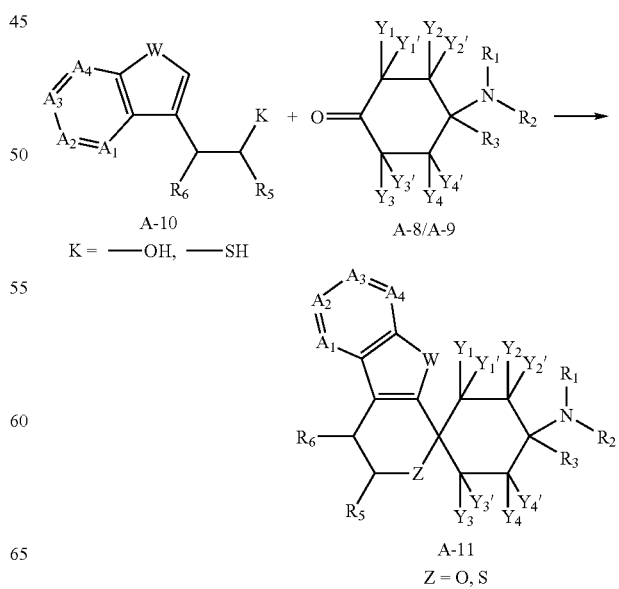

A-10
K = —OH, —SH

A-8/A-9

A-11
Z = O, S

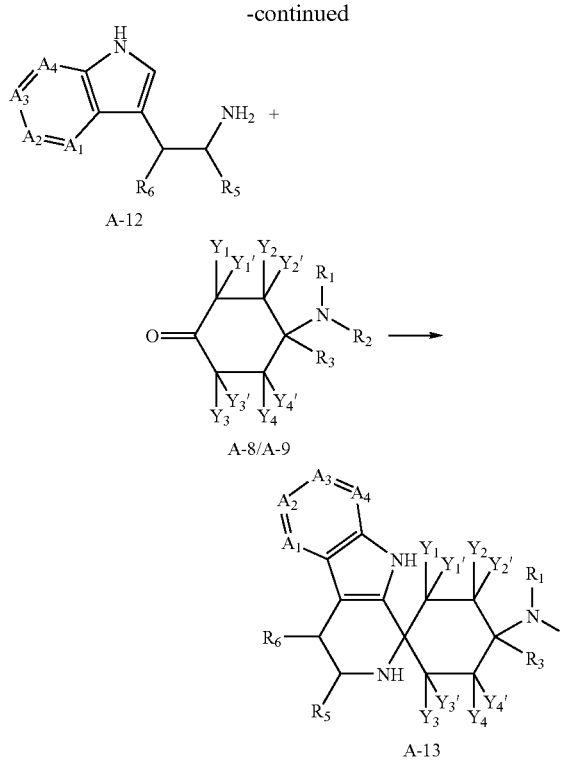

Tryptophols or other heterocycles of type A-10 (K=O) can be caused to react in Oxa-Pictet-Spengler type reactions, and tryptamines or other heterocycles of type A-12 can be caused to react in Pictet-Spengler type reactions, with ketones of type A-8/A-9 with the addition of at least one suitable reagent from the group acids, acid anhydrides, esters or weakly acid-reacting salts or Lewis acids to form products of formula A-11/A-13. The reaction proceeds in a similar manner for X=SH. In this case, at least one reagent is preferably used from the group carboxylic acids, phosphoric acids or sulphonic acids or their respective anhydrides, carboxylic acid trialkylsilyl esters, acid reacting salts, mineral salts or Lewis acids selected from the group comprising boron trifluoride, indium (III) chloride, titanium tetrachloride, aluminium(III) chloride, or with addition of at least one transition metal salt, preferably with addition of at least one transition metal triflate (transition metal trifluoromethane sulphonate), particularly preferred with addition of a transition metal trifluoromethane sulphonate selected from the group comprising scandium(III) trifluoromethane sulphonate, ytterbium(III) trifluoromethane sulphonate and indium(III) trifluoromethane sulphonate, possibly with addition of celite, with solid phase-bonded reactants or reagents, at elevated or reduced temperature, with or without microwave incident radiation, possibly in a suitable solvent or solvent mixture such as e.g. chlorinated or unchlorinated, preferably aromatic, hydrocarbons, acetonitrile; in ether solvents, preferably in diethyl ether or THF; or in nitromethane, in suitable cases also in alcohols or water.

It is particularly preferred in this case if the following are used: pyridinium-para-toluol sulphonate, phosphorus pentoxide in the presence of celite, boron trifluoride etherate, trifluoroacetic acid, orthotitanic acid tetraisopropylester together with trifluoroacetic acid, trifluoromethane sulphonic acid trimethylsilyl ester, trifluoromethane sulphonic acid, methanesulphonic acid, trifluoroacetic acid, acetic acid, phosphoric acid, polyphosphoric acid, polyphosphate ester, p-toluol sulphonic acid, hydrochloric acid HCl gas, sulphuric acid together with acetate buffer, tin tetrachloride.

f) Synthesis of Spirocyclic Compounds of Type A-14
Unit Syntheses-alkines

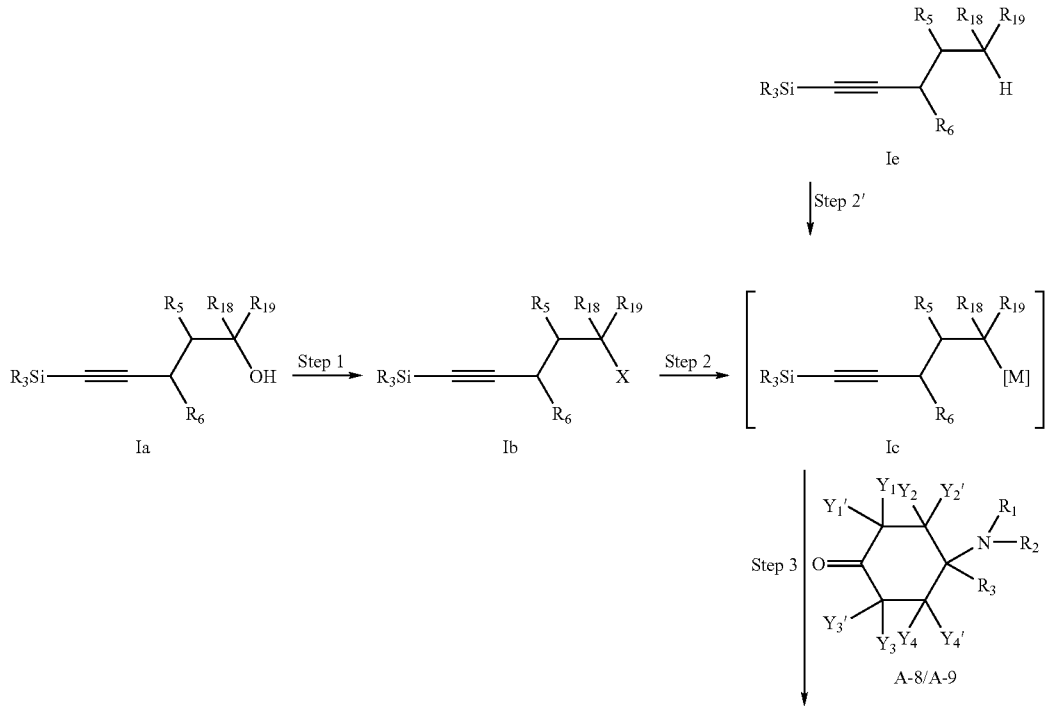

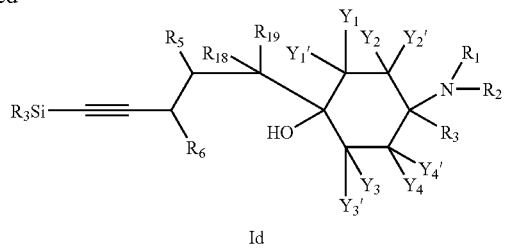

Id

In step 1 alcohols of the general formula Ia are converted either after conversion into a leaving group (e.g. —OSO$_2$-Me-OSO$_2$-p-toluol, —OTf) or directly (in the sense of a Mukaiyama redox condensation) into halides of the general formula Ib (X=Cl, Br, I). These are converted by halogen metal exchange either to the corresponding lithium organyls ([M]=Li) or Grignard reagents ([M]=MgX) of type Ic (step 2).

Alternatively, in step 2' lithium organyls of type Ic are produced working from alkines of the general formula Ie (with R$_{18}$ or R$_{19}$=e.g. SO$_2$Ph, SOPh, —CN, —C(=O)N(CH$_3$)OCH$_3$) by deprotonation with lithium amides (e.g. LDA).

In step 3 the metallised organyls of the general formula Ic are converted to the corresponding alkine units of type Id in the sense of a 1,2-addition to the carbonyl group of cyclohexanones of the general formula A-8/A-9.

Larock Reaction and Spirocyclisation

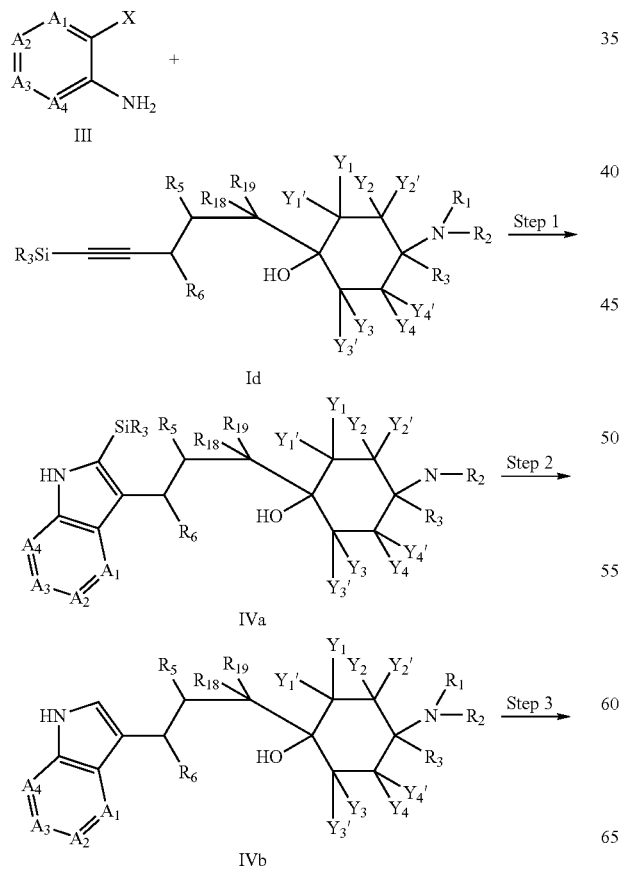

-continued

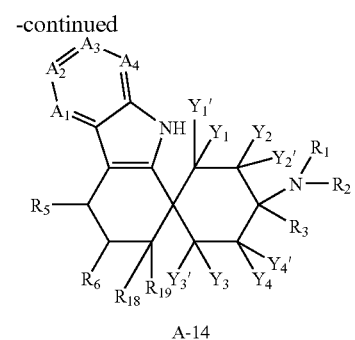

A-14

In step 1 compounds of the general formula III, in which X stands for a halogen residue or a sulphonic acid ester, are converted with alkines of the general formula Id to indoles of the general formula IVa in the sense of an indole synthesis according to Larock with the addition of a palladium catalyst. Compounds of the general formula III are commercially available (exemplary syntheses, see also WO2008009416). In step 2 compounds of the general formula IVa are desilylated in the presence of fluoride or in the presence of an organic or inorganic acid and converted to compounds of the general formula IVb. For the production of spirocyclic compounds of the general formula A-14, the alcohols of the general formula IVb are converted with the addition of an organic acid or trimethylsilyl ester thereof or an inorganic acid or with the addition of a transition metal salt.

g) Derivatisation of Spirocyclic Compounds (Secondary Amines)

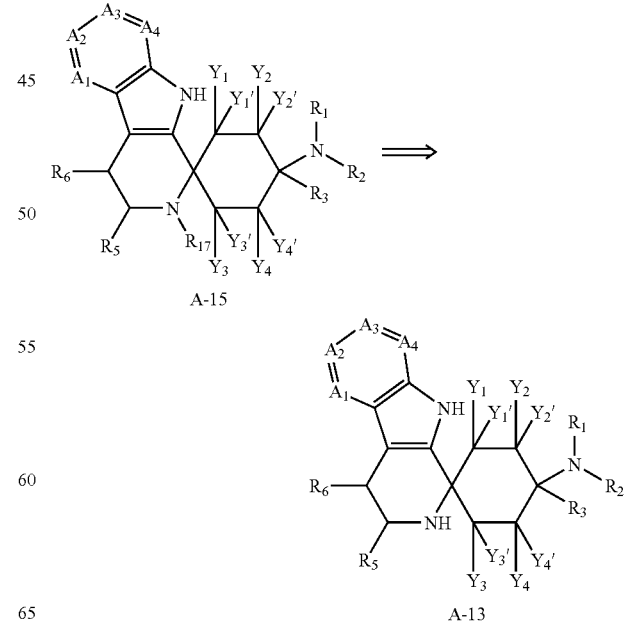

A-15

A-13

Secondary amines of type A-13 can be acylated, sulphonylated or carbamoylated to compounds of type A-15 by methods known to the skilled person. These reactions are preferably conducted at elevated temperature, particularly preferred with microwave incident radiation.

Such a method known to the skilled person can be the conversion with an anhydride or an acid chloride with the addition of a base, e.g. triethylamine.

Compounds of the general formula A-13 can be converted with isocyanates into the corresponding urea derivatives of type A-15.

In addition, compounds of the general formula A-13 can be converted to compounds of type A-15 with aldehydes with the addition of at least one reducing agent in the sense of a reductive amination.

h) Preliminary Steps

Compounds of the general formulae A-1, A-3, A-10 and A-12 are either commercially available or their production is known from the prior art or can be derived from the prior art in an obvious manner for the skilled person. Particularly relevant in this case are the following citations: Jirkovsky et al., J. Heterocycl. Chem., 12, 1975, 937-940; Beck et al., J. Chem. Soc. Perkin 1, 1992, 813-822; Shinada et al., Tetrahedron Lett., 39, 1996, 7099-7102; Garden et al., Tetrahedron, 58, 2002, 8399-8412; Lednicer et al., J. Med. Chem., 23, 1980, 424-430; Bandini et al. J. Org. Chem. 67, 15; 2002, 5386-5389; Davis et al., J. Med. Chem. 35, 1, 1992, 177-184; Yamagishi et al., J. Med. Chem. 35, 11, 1992, 2085-2094; Gleave et al.; Bioorg. Med. Chem. Lett. 8, 10, 1998, 1231-1236; Sandmeyer, Helv. Chim. Acta; 2; 1919; 239; Katz et al.; J. Med. Chem. 31, 6, 1988; 1244-1250; Bac et al. *Tetrahedron Lett.* 1988, 29, 2819; Ma et al. J. Org. Chem. 2001, 66, 4525; Kato et al. J. Fluorine Chem. 99, 1, 1999, 5-8.

With respect to further details on the synthesis of the compounds according to the invention, in particular with respect to the synthesis of suitable educt units, reference is additionally made to the following in their full scope: WO2004/043967, WO2005/063769, WO2005/066183, WO2006/018184, WO2006/108565, WO2007/124903 and WO2008/009416. A skilled person is aware that suitable educt units for the synthesis of the compounds according to the invention can be produced in a similar manner to the synthesis diagrams and exemplary embodiments disclosed in these publications.

EXAMPLES

The following examples serve to explain the invention in more detail, while not restricting it.

The yields of the compounds produced are not optimised. All temperatures are uncorrected. The term "ether" means diethyl ether, "EE" ethyl acetate and "DCM" dichloromethane. The term "equivalents" means substance amount equivalents, "mp" melting point or melting range, "decomp." decomposition, "RT" room temperature, "abs." absolute (free from water), "rac." racemic, "conc." concentrated, "min" minutes, "h" hours, "d" days, "% vol." percent by volume, "% m" percent by mass and "M" is a concentration detail in mol/l.

Silica gel 60 (0.040-0.063 mm) from E. Merck, Darmstadt was used as the stationary phase for the column chromatography. The thin-film chromatography tests were conducted with silica gel 60 F 254 HPTLC chromatoplates from E. Merck, Darmstadt. The mixture ratios of mobile solvents for chromatography tests are always given in volume/volume.

1. Unit Synthesis:
Ketone Units (±)-4-Dimethylamino-2-methyl-4-phenylcyclohexanone Diisopropylamine (2.1 ml, 15 mmol) was provided in dry THF in argon and mixed with n-butyl lithium in hexane (2.5M, 6 ml, 15 mmol) at 30° C. The reaction mixture was cooled to −78° C. 4-(dimethylamino)-4-phenylcyclohexanone (2.17 g, 10 mmol), dissolved in 10 ml of dry THF, was added in drops to this solution within 10 min. The batch was stirred for 30 min at −78° C. and then mixed with methyl iodide (1.86 ml, 30 mmol). It was heated to RT and stirred for a further 18 h. The solvent was removed at the rotary evaporator and the residue taken up in DCM. Extraction was conducted with 1N HCl (3×30 ml). The aqueous phase was basified with 5N NaOH (20 ml) and extracted with DCM (3×30 ml). The combined organic phases were washed with $H_2O$ (2×10 ml) and dried over $Na_2SO_4$. The semisolid residue (1.2 g) obtained after removal of the solvent was recrystallised from ethyl acetate (1 ml).

Yield: 549 mg (23%)

Melting point: 50° C.

(±)-2-Benzyl-4-dimethylamino-4-phenylcyclohexanone

Diisopropylamine (2.1 ml, 15 mmol) was provided in dry THF (30 ml) in argon and mixed with a solution of butyl lithium in hexane (2.5M, 6 ml, 15 mmol) at −30° C. (bath temperature. The reaction mixture was cooled to −78° C. After this temperature was reached, 4-(dimethylamino)-4-phenylcyclohexanone (2.17 g, 10 mmol), dissolved in dry THF (10 ml), was added in drops within 15 min. The batch was left for 30 min at −78° C. Benzyl bromide (3.6 ml, 30 mmol), dissolved in dry THF (20 ml), was then added within 10 min. The reaction mixture was stirred for a further 15 min at 78° C. (?), then the cooling removed. After room temperature was reached, the batch was stirred for a further 18 h. For work up the batch was carefully mixed with water (1 ml), then saturated $NH_4Cl$ solution (40 ml) was added. The organic phase was separated and the aqueous solution extracted with ethyl acetate (3×20 ml). The combined organic phases were washed with saturated $NH_4Cl$ solution (2×40 ml). The organic phases were then mixed with 1N HCl (50 ml) and thoroughly shaken out. The acid aqueous phase was separated, the organic phase washed with water (2×20 ml). The combined aqueous phases were washed with ethyl acetate (1×30 ml). The aqueous solution was then placed on 70 ml of 2N NaOH. An oil separated out of the alkaline solution. The formed mixture was extracted with ethyl acetate (3×30 ml). The combined organic phases were dried over $MgSO_4$ and then concentrated to low volume. One of the possible diastereoisomers was isolated from the residue (2.27 g) by chromatographic purification [silica gel 60 (50 g); ethyl acetate (1000 ml)].

Yield: 1.2 g (40%).

$^{13}C$ NMR (101 MHz, $CDCl_3$) δ ppm: 32.8, 33.2, 34.9, 37.3, 38.1, 38.3, 38.7, 47.6, 61.5, 126.1, 127.0, 127.6, 128.2, 128.3, 129.0, 135.4, 139.8, 211.4.

(±)-2-(3-Fluorobenzyl)-4-dimethylamino-4-phenylcyclohexanone

Diisopropylamine (2.1 ml, 15 mmol) was provided in dry THF (30 ml) in argon and mixed with a solution of butyl lithium in hexane (2.5M, 6 ml, 15 mmol) at −30° C. (bath temperature). The reaction mixture was cooled to −78° C. After this temperature was reached, 4-(dimethyl-amino)-4-phenylcyclohexanone (2.17 g, 10 mmol), dissolved in dry THF (20 ml), was added in drops within 15 min. The batch was left for 30 min at −78° C. 1-(bromomethyl)-3-fluorobenzoyl (3.7 ml, 30 mmol) dissolved in dry THF (10 ml) was then added within 1 min. The reaction mixture was stirred a further 10 min at −78° C., then the cooling was removed. After room temperature was reached, the batch was stirred for a further 18 h. For work up the batch was carefully mixed with water (1 ml), then saturated $NH_4Cl$ solution (40 ml) was added. The organic phase was separated and the aqueous solution extracted with ethyl acetate (3×20 ml). The combined organic phases were washed with saturated $NH_4Cl$ solution (2×40 ml). The organic phases were then mixed with 1N HCl (30 ml) and thoroughly shaken out. The acid aqueous phase was separated, the organic phase washed with water (2×20 ml). The combined aqueous phases were washed with ethyl acetate (1×30 ml). The aqueous solution was then placed on 70 ml of 2N NaOH. An oil separated out of the alkaline solution. The formed mixture was extracted with ethyl acetate (3×30 ml). The combined organic phases were dried over $MgSO_4$ and then concentrated to low volume. One of the possible diastereoisomers was isolated from the residue (2.1 g) by chromatographic purification [silica gel 60 (70 g); ethyl acetate (700 ml)].

Yield: 1.11 g (approx. 34%), purity approx. 90%.

$^{13}C$ NMR (101 MHz, $CDCl_3$) δ ppm: 33.0, 34.7, 38.1, 38.3, 38.7, 38.8, 47.3, 61.5, 113.0, 113.1, 115.7, 115.9, 124.7, 127.0, 127.1, 127.3, 127.5, 127.9, 128.3, 129.7, 129.8, 135.4, 142.4, 142.5, 161.7, 164.1, 211.0.

(±)-4-Dimethylamino-4-phenyl-2-thiophenylcyclohexanone (More Non-polar Diastereoisomer and More Polar Diastereoisomer)

Diisopropylamine (1.65 ml, 11.4 mmol) was provided in dry THF (20 ml) in argon and mixed with a solution of butyl lithium in hexane (2.5M, 5 ml, 12.5 mmol) at −30° C. (bath temperature). The reaction mixture was cooled to −78° C. After this temperature was reached, 4-(dimethylamino)-4-phenylcyclohexanone (2.17 g, 10 mmol), dissolved in dry THF (10 ml), was added in drops within 1-2 min. The batch was left for 30 min at −78° C. Diphenyl disulphide (2.18 g, 10 mmol), dissolved in dry THF (10 ml), was then added within 10 min.

The reaction mixture was stirred for a further 60 min at −78° C., then the cooling was removed. After room temperature was reached, the batch was stirred for a further 18 h. For work up the batch was carefully mixed with water (1 ml), then saturated $NH_4Cl$ solution (40 ml) was added. After intensive mixing of the phases, the organic solvent was separated and the aqueous phase extracted with ethyl acetate (3×20 ml). The combined organic phases were washed with saturated $NH_4Cl$ solution (2×40 ml). The organic phases were then mixed with 1N HCl (50 ml) and thoroughly shaken out. The acid aqueous phase was separated and the organic phase washed with water (2×20 ml). The combined aqueous phases were washed with ethyl acetate (1×30 ml). The aqueous solution was then placed on 2N NaOH (70 ml). An oil separated out of the alkaline solution. The formed mixture was extracted with ethyl acetate (3×30 ml). The combined organic phases were dried over $MgSO_4$ and then concentrated to low volume. The more non-polar diastereoisomer of the ketone with a yield of 540 g (16%) and the more polar diastereoisomer of the ketone with a yield of 730 mg (22%) were isolated as white solid substances from the residue (2.48 g) by chromatographic purification [silica gel 60 (50 g); cyclohexane (500 ml), cyclohexane/ethyl acetate 1:1 (500 ml), ethyl acetate (500 ml)]. The two diastereoisomers contained the respective other isomer in a quantity of approximately 10%*, so that it was not possible to determine the melting points of the pure substances.

On standing for a longer period in chloroform solution an isomerisation of the diastereoisomers was observed (the isomeric ratio changed after 14 days from non-polar/polar from approx. 1:9 to approx. 1:1.7), and therefore it was probably not possible to isolate the isomers in a respectively pure form.

More non-polar diastereoisomer: $^{13}C$ NMR (101 MHz, $CDCl_3$) δ ppm: 33.8, 36.5, 38.0, 41.4, 53.5, 60.0, 126.6, 127.1, 127.5, 127.7, 128.9, 132.9, 133.9, 137.2, 206.4 (after subtraction of the signals of the other isomer)

More polar diastereoisomer: $^{13}C$ NMR (101 MHz, $CDCl_3$) δ ppm: 32.4, 37.2, 38.7, 40.7, 54.4, 61.6, 127.3, 127.4, 127.6, 128.4, 128.9, 132.9, 133.8, 135.9, 206.0 (after subtraction of the signals of the other isomer)

(±)-(5-Dimethylamino-2-oxo-5-phenylcyclohexyl) methyl acrylate (More Non-polar Diastereoisomer and More Polar Diastereoisomer)

Diisopropylamine (2.1 ml, 15 mmol) was provided in dry THF (30 ml) in argon and mixed with a solution of butyl lithium in hexane (2.5M, 5 ml, 12.5 mmol) at −30° C. (bath temperature). The reaction mixture was cooled to −78° C. After this temperature was reached, 4-(dimethylamino)-4-phenylcyclohexanone (2.17 g, 10 mmol), dissolved in dry THF (10 ml), was added in drops within 1 min. The batch was left for 30 min at −78° C. Then, methyl bromoacetate (1 ml, 10.6 mmol), dissolved in dry THF (5 ml), was added in drops within 1 min. The reaction mixture was stirred for 1 h at −78° C. After room temperature was reached, the batch was stirred for a further 4 h. After approx. 2 h the batch became cloudy and a precipitate began to separate out. For work up the batch was carefully mixed with water (1 ml), then a mixture of saturated NaCl solution (30 ml) and 2 N HCl (20 ml) was added. The mixture was stirred for 10 min, the organic phase separated and extracted with saturated NaCl solution (2×10 ml). The combined aqueous phases were washed with ethyl acetate (3×20 ml) and then added to a saturated $NaHCO_3$ solution (approx. 30 ml) for neutralisation. The emulsion formed was strongly basified with 2N NaOH and extracted with ethyl acetate (3×30 ml). The combined organic phases were dried over $MgSO_4$ and then concentrated to low volume. The two possible diastereoisomers of the ketone were isolated from the residue (2.53 g) with yields of 710 g (more non-polar diastereoisomer, 24%) and 260 mg (more polar diastereoisomer with an impurity of approx. 10% of a diester, approx. 8%) by means of chromatographic purification [silica gel 60 G (10 g); cyclohexane/ethyl acetate 2:1 (70 ml), cyclohexane/ethyl acetate 1:1 (70 ml), ethyl acetate (70 ml)]. Since according to all observations made hitherto the di-substituted ketones do not react with tryptophol, a further purification of the more polar compound could be omitted.

(±)-2-Allyl-4-dimethylamino-4-phenylcyclohexanone (More Non-polar Diastereoisomer and More Polar Diastereoisomer)

Diisopropylamine (2.1 ml, 15 mmol) was provided in dry THF (30 ml) in argon and mixed with a solution of butyl lithium in hexane (2.5M, 6 ml, 15 mmol) at −30° C. (bath temperature). The reaction mixture was cooled to −78° C. After this temperature was reached, 4-(dimethyl-amino)-4-phenylcyclohexanone (2.17 g, 10 mmol), dissolved in dry THF (20 ml), was added in drops within 15 min. The batch was left for 30 min at −78° C. Then, allyl bromide (2.6 ml, 30 mmol), dissolved in dry THF (20 ml), was added in drops within 1 min. The reaction mixture was stirred for 10 min at −78° C., then the cooling was removed. After room temperature was reached, the batch was stirred for a further 18 h. For work up the batch was carefully mixed with water (1 ml), then saturated $NH_4Cl$ solution (40 ml) was added. The organic phase was separated and the aqueous phase was extracted with ethyl acetate (3×20 ml). The combined organic phases were washed with saturated $NH_4Cl$ solution (2×40 ml). The organic phases were then mixed with 1N HCl (30 ml) and thoroughly shaken out. The acid aqueous phase was separated and the organic phase was washed with water (2×20 ml). The combined aqueous phases were washed with ethyl acetate (1×30 ml). The aqueous solution was then placed on 2 N NaOH (70 ml). An oil separated out of the alkaline solution. The formed mixture was extracted with ethyl acetate (3×30 ml). The combined organic phases were dried over $Na_2SO_4$ and then concentrated to low volume. The more non-polar diastereoisomer of the ketone was isolated from the residue (2 g) with a yield of 540 g (22%) by means of chromatographic purification [silica gel 60 (50 g); cyclohexane/ethyl acetate 1:10 (700 ml)]. The more polar diastereoisomer was obtained with a yield of 470 mg (19%).

(±)-4-Dimethylamino-2-fluoro-4-phenylcyclohexanone

Lithium diisopropylamide (16.6 ml, 29.91 mmol, 1.8M in tetrahydrofuran, heptane, ethyl benzol) was added in drops to a solution of 4-(dimethylamino)-4-phenylcyclohexane (5.00 mg, 23.01 mmol) in absolute tetrahydrofuran (70 ml) in an argon atmosphere at −78° C. The mixture was stirred at −78° C. for 10 min and then heated to room temperature. The reaction mixture was then cooled to −78° C. again and N-fluoro-bis(phenylsulphonyl)amine (NFSI, 9.43 g, 29.91 mmol) in absolute tetrahydrofuran (100 ml) was added in drops. The reaction mixture was slowly heated to room temperature and stirred for 4 h. The volatile constituents were then completely removed in a vacuum. The residue was then mixed with ethyl acetate (100 ml) and water (80 ml). The phases were separated. The aqueous phase was extracted with ethyl acetate (3×40 ml). The combined organic phases were dried over sodium sulphate, filtered and the volatile constituents removed in vacuum. The remaining light yellow resin was applied to coarse silica gel with ethyl acetate (50 ml) and separated by chromatography [silica gel (150 g), cyclohexane/ethyl acetate 3:1 (500 ml), 2:1 (500 ml), 1:1 (500 ml), 1:2 (1000 ml)]. 663 mg (2.82 mmol, 12%) of the non-polar ketone and 1488 mg (6.32 mmol, 27%) of the polar ketone were isolated as a colourless microcrystalline powder.

$^{13}C\ \{^1H\}$-NMR (101 MHz, DMSO-$D_6$) δ ppm (more non-polar diastereoisomers): 32.9 (1 C), 35.2 (1 C), 37.9 (2 C), 39.3 (1 C, d, J=18 Hz, with DMSO-$D_5$), 61.2 (1 C, d, J=11 Hz), 90.0 (1 C, d, J=185 Hz), 126.7 (2 C), 126.9 (1 C), 127.5 (2 C), 136.3 (1 C), 205.0 (1 C, d; J=13 Hz)

$^{13}C\ \{^1H\}$—NMR (101 MHz, DMSO-$D_6$) δ ppm (more polar diastereoisomer): 32.0 (1 C), 34.8 (1 C), 38.3 (2 C), 39.4 (1 C, d, J=18 Hz, with DMSO-$D_5$), 61.4 (1 C, d, J=11 Hz), 89.4 (1 C, d, J=187 Hz), 127.1 (1 C), 127.3 (2 C), 128.0 (2 C), 135.4 (1 C), 204.3 (1 C, d, J=14 Hz)

2-(5-Dimethylamino-2-oxo-5-phenylcyclohexylmethyl)isoindoline-1,3-dione (One of Two Possible Diastereoisomers)

Lithium diisopropylamide solution (1.8M in hexane, 6 ml, 10 mmol) was provided in absolute tetrahydrofuran (10 ml). The solution was cooled to −78° C. After this temperature was reached, 4-(dimethylamino)-4-phenylcyclohexanone (1.1 g, 5 mmol), dissolved in dry THF (5 ml), was added in drops within 1 min. The batch was left for 30 min at −78° C. Then, N-(bromomethyl)phthalimide (3.6 ml, 15 mmol), dissolved in dry THF (20 ml), was added in drops within 1 min. The reaction mixture was stirred for 1 h at −78° C., then the cooling was removed. After room temperature was reached, the batch was stirred for a further 18 h. For work up the batch was carefully mixed with water (1 ml), then saturated $NH_4Cl$ solution (40 ml) was added. The organic phase was separated and the aqueous phase was extracted with ethyl acetate (3×30 ml). The combined organic phases were washed with saturated $NH_4Cl$ solution (1×40 ml). The organic phases were then mixed with 1N HCl (50 ml) and thoroughly shaken out. The acid aqueous phase was separated and the organic phase was washed with water (2×20 ml). The combined aqueous phases were washed with ethyl acetate (1×30 ml). The aqueous solution was then placed on 2N NaOH (70 ml). An oil separated out of the alkaline solution. The formed mixture was extracted with ethyl acetate (3×30 ml). The combined organic phases were dried over $Na_2SO_4$ and then concentrated to low volume. One of the two possible diastereoisomers of the ketone was isolated from the obtained residue (2 g) with a yield of 223 mg (12%) by means of chromatographic purification [silica gel 60 G (50 g); cyclohexane/ethyl acetate 1:10 (700 ml)].

(±)-3-(5-Dimethylamino-2-oxo-5-phenylcyclohexyl)propionitrile (One of Two Possible Diastereoisomers)

4-(dimethylamino)-4-phenylcyclohexanone (2.17 g, 10 mmol) was added to a solution of cyclohexylamine (109 mg, 1 mmol), glacial acetic acid (26 mg, 0.43 mmol) and 4-methoxyphenol (26 mg, 0.21 mmol) in 10 ml of toluol. The mixture was heated to 90° C. (bath temperature) and mixed with acrylonitrile (4 ml, 60.8 mmol) within 2 h. The batch was then heated to 120° C. After 3 h the heating was removed and the batch mixed with 1N NaOH (20 ml) after RT was reached. The mixture obtained was extracted with ethyl acetate (3×20 ml). The combined organic phases were washed with water and then dried over $MgSO_4$. The residue (2.2 g) obtained after removal of the solvent solidified upon standing and was mainly composed of the initial ketone and a more non-polar product compared to this. One of the two possible diastereoisomers of the ketone was obtained with a yield of 400 mg (14%) in the form of an oil by means of chromatographic purification [silica gel 60 G (10 g); cyclohexane/ethyl acetate 1:10 (120 ml)].

Example No. 1 and Example No. 2

Step 1:

N,N,2-trimethyl-4-phenyl-4',9'-dihydro-3'H-spiro [cyclohexane-1,1'-pyrano[3,4-b]indole]-4-amine (non-polar diastereomer and polar diastereomer mixture)

(±)-4-dimethylamino-2-methyl-4-phenylcyclohexanone (461 mg, 2 mmol) together with tryptophol (322 mg, 2 mmol)

was dissolved in DCM (100 ml) and mixed with trifluoromethane sulphonic acid (0.19 ml, 2.14 mmol). The mixture was stirred at RT for 20 h. The reaction mixture was mixed with 2N NaOH (2 ml) and H₂O (2 ml) and stirred for 20 min. The organic residue was firstly washed with 2N NaOH (5 ml), then with H₂O (5 ml) and dried over Na₂SO₄. The solvent was then removed in vacuum. The semisolid residue obtained was taken up in 10 ml of ethanol and cooled to 5° C. for 2 h. The solid precipitated out during this was discarded. The residue remaining in the mother liquor was purified by column chromatography on silica gel (50 g, EE/ethanol=4:1).

Yield (non-polar diastereomer): 375 mg (50%), white solid
Melting point: 190-210° C.
Yield (more polar diastereomer mixture): 83 mg (11%), with up to 20% impurity from a further diastereoisomer.

Step 2:

N,N,2-trimethyl-4-phenyl-4',9'-dihydro-3'H-spiro [cyclohexane-1,1'-pyrano[3,4-b]indole]-4-amine; 2-hydroxypropane-1,2,3-tricarboxylate (1:1) (Example No. 1, Non-polar Diastereomer)

(±)-N,N,2-trimethyl-4-phenyl-4',9'-dihydro-3'H-spiro[cyclohexane-1,1'-pyrano[3,4-b]indole]-4-amine (240 mg, 0.64 mmol) was dissolved in boiling ethanol (100 ml). Citric acid (124 mg, 0.65 mmol) dissolved in ethanol (10 ml) was then added and the reaction mixture cooled to approx. 5° C. After 60 h at this temperature the precipitated solid was separated.

Yield: 135 mg (37%), light yellow crystalline solid
Melting point: 221-223° C.
HPLC/MS analysis: Rt=2.87 min; m/z=374.9

N,N,2-trimethyl-4-phenyl-4',9'-dihydro-3'H-spiro [cyclohexane-1,1'-pyrano[3,4-b]indole]-4-amine; 2-hydroxypropane-1,2,3-tricarboxylate (1:1) (Example No. 2, Polar Diastereomer Mixture)

The more polar spiro ether mixture (83 mg, 0.22 mmol) was dissolved in boiling ethanol (20 ml). Citric acid (43 mg, 0.22 mmol) dissolved in ethanol (10 ml) was then added and the reaction mixture was stirred at RT for 1 h. Citrate in the form of a vitreous solid was obtained after removal of the solvent.

Yield: 124 mg (100%)
Melting point: 64-83° C.
HPLC/MS analysis: Rt=2.63 min; m/z=375.0 (80%) and Rt=2.76 min; m/z=374.9 (20%)

Example No. 3

Step 1:

2-Methyl-4-(dimethylamino)1-4-phenyl-spiro[cyclohexane-1,8'-(5,6,8,9-tetrahydro-pyrano[3,4-b]-7-azaindole)]

4-dimethylamino-2-methyl-4-phenylcyclohexanone (0.42 g, 1.85 mmol) was provided together with 2-(1H-pyrrolo[2,3-b]pyridin-3-yl)ethanol (0.30 g, 1.85 mmol) in ultradry state with nitrogen in dichloromethane (5 ml). Trimethylsilyl trifluoromethane sulphonate (1.43 ml, 7.4 mmol) was then quickly added. The mixture was stirred at room temperature for 7 days. After adding dichloromethane the mixture was basified with 1M of Na₂CO₃ solution and stirred for 20 min. The organic phase was separated and the aqueous phase extracted with dichloromethane (3×). The combined organic extracts were washed with saturated NaCl solution and dried over MgSO₄. After filtration of the drying agent the solvent was removed on the rotary evaporator. The solid obtained was mixed with methanol (5 ml) and the mixture stirred at room temperature for 2 h. The solid was aspirated and washed with a little methanol and dried via oil pump vacuum at 50° C.

Yield: 0.2 g (28%)

Step 2:

2-Methyl-4-(dimethylamino)1-4-phenyl-spiro[cyclohexane-1,8'-(5,6,8,9-tetrahydro-pyrano[3,4-b]-7-azaindole)]; 2-hydroxypropane-1,2,3-tricarboxylate (1:1) (Example No. 3, a Diastereomer)

(±)-2-methyl-4-(dimethylamino)1-4-phenyl-spiro[cyclohexane-1,8'-(5,6,8,9-tetrahydro-pyrano[3,4-b]-7-azaindole)] (0.194 g, 0.52 mmol) was suspended in hot ethanol (6 ml) and mixed with a likewise hot solution of citric acid (0.099 g) in ethanol (3 ml). The solution was stirred at room temperature for 3 h. The precipitate was then aspirated, washed in portions in ether and dried via high vacuum at 60° C.

Yield: 0.215 g (73%)
HPLC/MS analysis: Rt=2.0 min; m/z=376.0

Example No. 4

2-Benzyl-N,N-dimethyl-4-phenyl-4',9'-dihydro-3'H-spiro[cyclohexane-1,1'-pyrano[3,4-b]indole]-4-amine (Example No. 4, a Diastereomer)

(±)-2-benzyl-4-dimethylamino-4-phenylcyclohexanone (349 mg, 1.14 mmol) together with tryptophol (184 mg, 1.14 mmol) was dissolved in dichloromethane (30 ml) and mixed with trifluoromethane sulphonic acid trimethylsilyl ester (0.24 ml, 1.24 mmol). The batch was stirred at RT for 3 h. A precipitate began to separate out after some time (approx. 1 h). For work up the reaction mixture was mixed with 2N NaOH (20 ml) and stirred for 20 min. During this the precipitate went into solution. The organic phase was separated and the aqueous phase extracted with dichloromethane (4×20 ml). The combined organic phases were dried with MgSO₄. The solvent was then concentrated to low volume in a vacuum. One of the possible diastereoisomeric spiro ethers was isolated from the residue obtained (535 mg) by means of chromatographic purification [silica gel 60 G (10 g); ethyl acetate 300 ml].

Yield: 392 mg (76%)
Melting point: 122-125° C. (from toluol)
$^{13}$C NMR (101 MHz, CDCl₃) δ ppm: 22.5, 27.8, 31.7, 31.9, 36.3, 38.2, 44.9, 60.0, 61.7, 74.7, 109.5, 110.8, 118.0, 119.4, 121.6, 125.7, 126.6, 127.0, 127.6, 127.8, 128.0, 129.0, 135.8, 136.3, 137.0, 141.2.

Example No. 5

Step 1:

2-Benzyl-N,N-dimethyl-4-phenyl-2',3',4',9'-tetrahydrospiro[cyclohexane-1,1'-pyrido[3,4-b]indole]-4-amine (±)-2-benzyl-4-dimethylamino-4-phenylcyclohexanone (307 mg, 1 mmol) together with tryptamine (160 mg, 1 mmol) was dissolved in methanol and stirred at RT for 24 h. The solvent was then removed in a vacuum and the residue dissolved in 1,2-dichloroethane (20 ml). The mixture was mixed with trifluoroacetic acid (1.7 ml, 22.8 mmol) and stirred for 24 h at RT. For work up the reaction mixture was mixed with 2N NaOH (20 ml) and stirred for 20 min. The organic phase was separated and the aqueous phase extracted with dichloromethane (4×20 ml). The combined organic phases were dried with MgSO$_4$. The solvent was then concentrated by evaporation in a vacuum. One of the possible diastereoisomers was isolated from the residue obtained (260 mg) by means of chromatographic purification [silica gel 60 G (10 g); ethyl acetate/ethanol 1:1 (80 ml), methanol (60 ml)].

Yield: 80 mg (17%), vitreous solid (purity approx. 95%)

$^{13}$C NMR (101 MHz, CDCl$_3$-D6) δ ppm: 23.1, 28.4, 32.0, 33.2, 36.7, 38.1, 39.7, 45.1, 55.6, 61.9, 110.7, 110.9, 117.9, 119.2, 121.4, 125.9, 126.6, 127.5, 127.8, 127.9, 128.1, 129.1, 135.5, 135.6, 138.3, 141.0

Step 2:

2-Benzyl-N,N-dimethyl-4-phenyl-2',3',4',9'-tetrahydrospiro[cyclohexane-1,1'-pyrido[3,4-b]indole]-4-amine 2-hydroxypropane-1,2,3-tricarboxylate (1:1) (Example No. 5, a Diastereomer)

2-benzyl-N,N-dimethyl-4-phenyl-2',3',4',9'-tetrahydrospiro[cyclohexane-1,1'-pyrido[3,4-b]indole]-4-amine (one of 4 possible racemic diastereoisomer pairs, 62 mg, 0.14 mmol) was dissolved in 2-propanol (3 ml) in the boiling heat and mixed with a hot solution of citric acid [40 mg, 0.2 mmol, in hot isopropanol (1 ml)]. A precipitate separated out immediately. The batch was left 2 h at 5° C. to complete the precipitation, then the solid was separated by means of a fritted glass filter and dried.

Yield: 48 mg (53%), purity approx. 90%

Melting point: from 148° C.

$^{13}$C NMR (101 MHz, DMSO-D6) δ ppm: 21.8, 23.1, 26.0, 29.8, 32.5, 35.6, 37.3, 43.1, 43.9, 56.0, 61.9, 71.4, 108.6, 111.1, 117.4, 118.2, 120.6, 126.0, 126.6, 128.0, 128.2, 128.4, 128.6, 129.0, 131.7, 136.0, 137.0, 139.9, 171.2, 176.4

Example No. 6

2-(3-Fluorobenzyl)-N,N-dimethyl-4-phenyl-4',9'-dihydro-3'H-spiro[cyclohexane-1,1'-pyrano[3,4-b]indole]-4-amine (Example No. 6, a Diastereomer)

(±)-2-(3-fluorobenzyl)-4-dimethylamino-4-phenylcyclohexanone (325 mg, 1 mmol) together with tryptophol (161 mg, 1 mmol) was dissolved in dichloromethane (30 ml) and mixed with trifluoromethane sulphonic acid trimethylsilyl ester (0.22 ml, 1.14 mmol). The batch was stirred at RT for 2.5 h. A precipitate began to separate out after some time (approx. 1 h). For work up the reaction mixture was mixed with 2N NaOH (20 ml) and stirred for 20 min. During this the precipitate went into solution. The organic phase was separated and the aqueous phase extracted with dichloromethane (4×20 ml). The combined organic phases were dried with MgSO$_4$. The solvent was then concentrated by evaporation in a vacuum. One of the possible diastereoisomers was isolated from the residue obtained (352 mg) by means of chromatographic purification [silica gel 60 G (10 g); ethyl acetate 150 ml].

Yield: 240 mg (51%)

Melting point: from 108° C.

$^{13}$C NMR (101 MHz, CDCl$_3$) δ ppm: 22.5, 27.6, 31.6, 32.1, 36.1, 38.2, 44.7, 60.0, 61.7, 74.6, 109.6, 110.9, 112.5, 112.7, 115.5, 115.7, 118.0, 119.5, 121.7, 124.8, 126.7, 127.0, 127.9, 128.0, 129.3, 129.4, 135.7, 136.3, 136.7, 143.8, 143.9, 161.5, 164.0

Example No. 7

Step 1:

6'-Fluoro-2-(3-fluorobenzyl)-N,N-dimethyl-4-phenyl-4',9'-dihydrospiro[cyclohexane-1,1'-pyrano-[3,4-b]indole]-4-amine (Example No. 7, One of 4 Possible Racemic Diastereoisomer Pairs)

(±)-2-(3-fluorobenzyl)-4-dimethylamino-4-phenylcyclohexanone (325 mg, 1 mmol, one of two possible racemic diastereoisomers) together with 5-fluorotryptophol (179 mg, 1 mmol) was dissolved in dichloromethane (30 ml) and mixed with trifluoromethane sulphonic acid trimethylsilyl ester (0.22 ml, 1.14 mmol). The clear light yellow solution changed to brown. The batch was stirred at RT for 2 h. For work up the reaction mixture was mixed with 1N NaOH (30 ml) and stirred for 15 min. The organic phase was separated and the aqueous phase extracted with dichloromethane (2×20 ml). The combined organic phases were dried with Na$_2$SO$_4$. The solvent was then concentrated by evaporation in a vacuum. The residue obtained (477 mg) should be dissolved in ethyl acetate for the chromatography. During this, a white solid (86 mg) separated out that was identified as one of the 4 possible diastereoisomers by means of NMR and LC/MS. The filtrate was concentrated to low volume and purified by chromatography [silica gel 60 (20 g); ethyl acetate (600 ml)]. The product (242 mg) obtained was combined with the solid. One of the 4 possible diastereoisomers was thus obtained with a total yield of 328 mg (67%) with a melting point of 133-135° C.

Example No. 7: $^{13}$C-NMR (101 MHz, CDCl$_3$) δ ppm: 22.4, 27.5, 31.6, 32.2, 36.1, 38.2, 44.6, 59.9, 61.6, 74.5, 103.0, 103.3, 109.6, 109.9, 111.3, 111.4, 112.5, 112.7, 115.5, 115.7, 124.7, 126.7, 127.3, 127.4, 127.9, 128.0, 129.4, 132.2, 136.4, 138.8, 143.8, 156.7, 159.0, 161.5, 164.0

Example No. 8 and Example No. 9 and Example No. 10

Step 1:

2-(3-Fluorobenzyl)-N,N-dimethyl-4-phenyl-2',3',4',9'-tetrahydrospiro[cyclohexane-1,1'-pyrido[3,4-b]indole]-4-amine (Example No. 8, More Polar Isomer, Example No. 9, More Non-polar Isomer, Example No. 10, Second More Polar Isomer, 3 of 4 Racemic Diastereoisomer Pairs)

(±)-2-(3-fluorobenzyl)-4-dimethylamino-4-phenylcyclohexanone (478 mg, 1.47 mmol, one of two possible diastereoisomers) together with tryptamine (235 mg, 1.47 mmol) was dissolved in methanol (20 ml) and stirred at RT for 24 h. The solvent was then removed in vacuum and the residue dissolved in 1,2-dichloroethane (20 ml). The mixture was mixed with trifluoroacetic acid (1.5 ml, 20.3 mmol) and stirred for 24 h at RT. For work up the reaction mixture was mixed with 2N NaOH (24 ml) and stirred for 20 min. The organic phase was separated and the aqueous phase extracted with dichloromethane (4×20 ml). The combined organic phases were dried with MgSO$_4$. The solvent was then removed in a vacuum. A relatively polar racemic diastereoisomer pair (one of four possible isomers) was isolated from the residue obtained (510 mg) as vitreous solid with a yield of 130 mg (18% oil, which solidified upon standing) and with over 95% purity (more polar isomer). By means of a second chromatographic separation of the non-polar fractions [silica gel 60 G (10 g); ethyl acetate (140 ml), ethyl acetate/ethanol 1:1 (30 ml)] two more of the four possible racemic diastereoisomer pairs could be isolated. Unconverted ketone was separated from the fractions, which contained the more non-polar isomer, by washing out with methanol (1 ml). The racemic diastereoisomer pair was thus obtained with a yield of 29 mg (4% yield, more non-polar isomer) with a melting point from 258° C. A second more polar racemic diastereoisomer pair was likewise obtained by rubbing the corresponding fraction residues with methanol (approx. 1 ml) in crystalline form (melting point from 138° C. upon crystal-transformation) with a yield of 8 mg (1.7%, second more polar isomer).

Example No. 8: $^{13}$C-NMR (101 MHz, CDCl$_3$) δ ppm: 23.0, 28.2, 32.2, 33.0, 36.5, 38.1, 39.7, 44.7, 50.5, 61.7, 110.7, 112.6, 112.8, 115.6, 115.8, 117.9, 119.1, 121.3, 124.9, 126.6, 127.3, 127.8, 128.0, 129.4, 129.5, 135.6, 135.7, 138.1, 143.8, 143.9, 161.5, 163.9

Example No. 9: $^{13}$C-NMR (101 MHz, CDCl$_3$ δ ppm: 23.2, 28.5, 31.6, 32.3, 36.6, 37.8, 39.8, 42.8, 55.6, 59.3, 110.6, 110.9, 112.6, 112.8, 115.7, 115.9, 118.0, 119.2, 121.4, 124.8, 126.6, 126.7, 127.3, 127.6, 129.5, 129.6, 135.8, 139.0, 139.1, 144.3, 144.4, 161.5, 164.0

Example No. 10: $^{13}$C-NMR (101 MHz, CDCl$_3$) δ ppm: 23.1, 31.2*, 36.4, 36.9, 38.1, 39.7, 45.4, 56.1, 61.5*, 111.2, 112.8, 113.0, 115.7, 115.8, 118.0, 119.2, 121.6, 124.78, 124.81, 126.6, 127.2, 127.9, 128.1, 129.6, 129.7, 135.9, 143.7, 161.7, 164.1 widely spread signals

Example No. 11

Step 1:

N,N-dimethyl-4-phenyl-2-(phenylthio)-4',9'-dihydro-3'H-spiro[cyclohexan-1,1'-pyrano[3,4-b]indole]-4-amine (Example No. 11, one of 4 Possible Racemic Diastereoisomer Pairs)

A mixture of (±)-4-dimethylamino-4-phenyl-2-thiophenylcyclohexanone (300 mg, 0.92 mmol) together with tryptophol (148 mg, 0.92 mmol) was dissolved in dichloromethane (50 ml) and mixed with trifluoromethane sulphonic acid trimethylsilyl ester (0.2 ml, 1.1 mmol). The batch was stirred for 20 h at RT. For work up the reaction mixture was mixed with 2N NaOH (10 ml) and stirred for 2 h. The organic phase was separated and the aqueous phase extracted with dichloromethane (4×20 ml). The combined organic phases were dried with MgSO$_4$. The solvent was then removed in a vacuum. One of the four possible diastereoisomers was isolated from the residue obtained (420 mg) as vitreous solid, which solidified after rubbing with ethanol (2 ml), by means of chromatographic purification [silica gel 60 G (10 g); cyclohexane/ethyl acetate 4:1 (150 ml)]. The product could thus be obtained with a yield of 79 mg (18%) with a melting point of 228-233° C. (from 120° C. upon crystal transformation).

Example No. 11: $^{13}$C-NMR (101 MHz, CDCl$_3$) δ ppm: 22.4, 26.9, 28.0, 30.4, 36.5, 38.0, 54.4, 60.48, 60.52, 75.0, 109.5, 111.0, 118.2, 119.4, 121.6, 126.7, 126.9, 127.0, 127.4, 128.6, 133.0, 135.8, 136.1, 136.9, 138.6

Example No. 12 and Example No. 13

Step 1:

N,N-dimethyl-4-phenyl-2-(phenylthio)-2',3',4',9'-tetrahydrospiro[cyclohexane-1,1'-pyrido[3,4-b]indole]-4-amine (Example No. 12, More Non-polar Isomer and Example No. 13, More Polar Isomer, Two of 4 Possible Racemic Diastereoisomer Pairs)

The more polar 4-dimethylamino-4-phenyl-2-thiophenylcyclohexanone (277 mg, 0.85 mmol) together with tryptamine (136 mg, 0.85 mmol) was dissolved in methanol (20 ml) and stirred for 24 h at RT. The solvent was then removed in vacuum and the residue dissolved in 1,2-dichloroethane (20 ml). The mixture was mixed with trifluoroacetic acid (1.5 ml, 20.3 mmol) and stirred for 24 h at RT. For work up the reaction mixture was mixed with 2N NaOH (20 ml) and stirred for 30 min. The organic phase was separated and the aqueous phase extracted with dichloromethane (3×20 ml). The combined organic phases were dried with MgSO$_4$. The solvent was then concentrated by evaporation in vacuum. Two of the possible diastereoisomers were obtained from the residue obtained (410 mg) by means of chromatographic purification [silica gel 60 G (10 g); ethyl acetate/ethanol 3:1 (150 ml), methanol (60 ml)]. A more non-polar isomer pair was formed as a solid with a yield of 72 mg (17%) with a melting point of 190-192° C. (after rubbing with MeOH). A more polar isomer pair was obtained by rubbing the corresponding fraction residues with methanol (1 ml) with a yield of 129 mg (32%) and a melting point of 171-173° C.

Example No. 12: $^{13}$C-NMR (101 MHz, CDCl$_3$) δ ppm: 23.3, 29.9, 35.6, 38.1, 38.9, 39.6, 55.4, 56.2, 62.1, 111.0, 111.3, 118.1, 119.1, 121.8, 126.4, 127.2, 127.4, 127.8, 128.2, 128.8, 132.2, 132.6, 134.4, 136.0

Example No. 13: $^{13}$C-NMR (101 MHz, CDCl$_3$) δ ppm: 23.0, 27.0, 33.2, 35.2, 38.3, 39.6, 55.7, 55.8, 62.8, 110.7, 110.9, 118.0, 119.0, 121.3, 126.9, 127.2, 127.4, 127.9, 128.1, 128.4, 133.7, 134.2, 135.5, 136.3, 137.5

Example No. 14

Step 1:

2-(4-(Dimethylamino)-4-phenyl-4',9'-dihydro-3'H-spiro[cyclohexane-1,1'-pyrano[3,4-b]indole]-2-yl) methyl acetate (Example No. 14, More Non-polar Diastereoisomer from More Non-polar Ketone, One of 4 Possible Racemic Diastereoisomer Pairs)

The more non-polar (5-dimethylamino-2-oxo-5-phenylcyclohexyl)methyl acetate (310 mg, 1.07 mmol) together with tryptophol (172 mg, 1.07 mmol) was dissolved in dichloromethane (30 ml) and mixed with trifluoromethane sulphonic acid trimethylsilyl ester (0.2 ml, 1.1 mmol). After 3 h a DC sample was taken that indicated a substantial conversion. The batch was stirred for 20 h at RT. For work up the reaction mixture was mixed with 2N NaOH (10 ml) and stirred for 20 min. The organic phase was separated and the aqueous phase extracted with dichloromethane (3×20 ml). The combined organic phases were dried with MgSO$_4$. The solvent was then removed in a vacuum. The solid obtained was mixed with methanol (3 ml). The mixture was heated until boiling, wherein the solid went only partially into solution. The mixture was left for 2 h at 5° C. to complete the precipitation. The solid was then separated by means of a fritted glass filter and dried in a vacuum. One of the four possible racemic diastereoisomer pairs could thus be isolated with a yield of 317 mg (68%) with a melting point of 262-268° C.

Example No. 14: $^{13}$C-NMR (101 MHz, CDCl$_3$) δ ppm: 22.4, 28.2, 29.5, 34.1, 34.8, 37.0, 38.1, 51.3, 59.4, 59.8, 74.4, 109.2, 111.1, 118.0, 119.3, 121.6, 126.6, 126.8, 127.3, 135.9, 137.1, 139.2, 174.3

Example No. 15

Step 1:

2-(4-(Dimethylamino)-4-phenyl-4',9'-dihydro-3'H-spiro[cyclohexane-1,1'-pyrano[3,4-b]indole]-2-yl) methyl acetate (Example No. 15, More Polar Diastereoisomer from More Polar Ketone, One of 4 Possible Racemic Diastereoisomer Pairs)

The more polar (5-dimethylamino-2-oxo-5-phenylcyclohexyl)methyl acetate (350 mg, with impurity of approx. 10% of a diester, calculated on the basis of pure monoester, 1.2 mmol) together with tryptophol (194 mg, 1.2 mmol) was dissolved in dichloromethane (20 ml) and mixed with trifluoromethane sulphonic acid trimethylsilyl ester (0.24 ml, 1.33 mmol). The batch was stirred for 20 h at RT. The precipitate precipitated from the solution was separated by means of a fritted glass filter and—since it was the trifluoromethane sulphonic acid salt of the spiro ether—was stirred in a mixture of dichloromethane (10 ml) and 2N NaOH (5 ml) for 2 h at RT. The organic phase was separated and the aqueous phase extracted with dichloromethane (3×10 ml). The combined organic phases were dried with MgSO$_4$. The solvent was then removed in a vacuum. A first batch of an isomer of the spiro ether was thus obtained with a yield of 67 mg and with a melting point of 253-269° C. To complete the work up the reaction solution obtained as mother liquor was mixed with 2N NaOH (10 ml) and stirred for 20 min. The organic phase was separated and the aqueous phase extracted with dichloromethane (3×20 ml). The combined organic phases were dried with MgSO$_4$. The solvent was then removed in a vacuum. The solid obtained was mixed with methanol (2 ml) and heated until boiling. After RT was reached the mixture was left for 17 h at 5° C. to complete the precipitation. The solid was then separated by means of a fritted glass filter and dried in a vacuum. A further batch of the racemic diastereoisomer pair could thus be isolated with a yield of 198 mg [total yield: 265 mg, 51%) (calculated on the basis of 100% monoester ketone)] with a melting point of 256-263° C.

Example No. 15: $^{13}$C-NMR (101 MHz, CDCl$_3$) δ ppm: 22.3, 28.1, 31.3, 33.0, 35.1, 38.3, 39.0, 51.3, 59.7, 61.9, 74.1, 109.5, 111.0, 118.0, 119.5, 121.7, 126.9, 128.0, 128.2, 135.7, 136.2, 136.4, 174.1

Example No. 16

Step 1:

2-(4-(Dimethylamino)-4-phenyl-4',9'-dihydro-3'H-spiro[cyclohexane-1,1'-pyrano[3,4-b]indole]-2-yl) methyl acetate (Example No. 16, One of 4 Possible Racemic Diastereoisomer Pairs)

(5-dimethylamino-2-oxo-5-phenylcyclohexyl)methyl acetate (310 mg, 1.07 mmol) together with tryptophol (172 mg, 1.2 mmol) was dissolved in dichloromethane (20 ml) and mixed with trifluoromethane sulphonic acid trimethylsilyl ester (0.2 ml, 1.1 mmol). The batch was stirred for 20 h at RT. For work up the reaction solution was mixed with 2N NaOH (5 ml) and stirred for 20 min. The organic phase was separated and the aqueous phase extracted with dichloromethane (3×20 ml). The combined organic phases were dried with MgSO$_4$. The solvent was then removed in a vacuum. The solid residue was mixed with methanol (3 ml) and left for 2 h at 5° C. The solid was then separated by means of a fritted glass filter and dried in a vacuum. A first batch of the desired product could thus be isolated with a yield of 47 mg. The methanol mother liquor was concentrated to low volume and the residue obtained (385 mg) purified by chromatography [silica gel 60 G (10 g); ethyl acetate/ethanol 2:1 (120 ml)]. Besides little already hydrolysed product (free alcohol), fractions could be obtained that contained a racemic diastereoisomer pair that turned out to be identical to the first batch. To remove the impurities present, the fractions were jointly concentrated to low volume, rubbed with methanol (1 ml) and left to stand for 48 h at 5° C. The racemic diastereoisomer pair could thus be isolated with a total yield of 98 mg (21%) with a melting point of 233-237° C.

Example No. 16: $^{13}$C-NMR (101 MHz, CDCl$_3$) δ ppm: 20.6, 22.2, 27.6, 30.9, 31.7, 38.3, 41.5, 59.8, 61.5, 65.7, 73.0, 108.7, 110.8, 118.0, 119.5, 121.7, 126.9, 127.0, 127.8, 128.2, 135.9, 136.3, 136.5, 170.9

Example No. 17

Step 1:

2-Allyl-N,N-dimethyl-4-phenyl-4',9'-dihydros-3'H-spiro[cyclohexane-1,1'-pyrano[3,4-b]indole]-4-amine (Example No. 17, from the More Polar Ketone, One of 4 Possible Racemic Diastereoisomer Pairs)

The more polar 2-allyl-4-dimethylamino-4-phenylcyclohexanone (230 mg, 0.89 mmol) together with tryptophol (143 mg, 0.89 mmol) was dissolved in dichloromethane (20 ml) and mixed with trifluoromethane sulphonic acid trimethylsilyl ester (0.21 ml, 1.2 mmol). The batch was stirred for 24 h at RT. For work up the reaction mixture was mixed with 2N NaOH (20 ml) and stirred for 20 min. The organic phase was separated and the aqueous phase extracted with dichloromethane (4×20 ml). The combined organic phases were dried with Na$_2$SO$_4$. The solvent was then removed in a vacuum. One of the possible diastereoisomers was isolated with a total yield of 130 mg (37%) with a melting point of 69-71° C. from the residue obtained (390 mg) by means of chromatographic purification [silica gel 60 (50 g); ethyl acetate (500 ml)].

Example No. 17: $^{13}$C-NMR (101 MHz, CDCl$_3$) δ ppm: 22.4, 27.5, 31.7, 32.1, 34.5, 38.2, 42.2, 59.8, 62.1, 74.5, 109.3, 110.8, 116.2, 117.9, 119.4, 121.5, 126.8, 126.9, 128.0, 128.1, 135.6, 136.7, 136.9, 137.3

Example No. 18

Step 1:

2-Allyl-N,N-dimethyl-4-phenyl-4',9'-dihydros-3'H-spiro[cyclohexane-1,1'-pyrano[3,4-b]indole]-4-amine (from the More Non-polar Ketone, One of 4 Possible Racemic Diastereoisomer Pairs)

The more non-polar 2-allyl-4-dimethylamino-4-phenylcyclohexanone (250 mg, 0.97 mmol) together with tryptophol (156 mg, 0.97 mmol) was dissolved in dichloromethane (25 ml) and mixed with trifluoromethane sulphonic acid trimethylsilyl ester (0.245 ml, 1.35 mmol). The batch was stirred for 24 h at RT. For work up the reaction mixture was mixed with 2N NaOH (20 ml) and stirred for 20 min. The organic phase was separated and the aqueous phase extracted with dichloromethane (4×20 ml). The combined organic phases were dried with Na$_2$SO$_4$. The solvent was then concentrated by evaporation in a vacuum. One of the possible diastereoisomers was isolated with a yield of 290 mg (74%) from the residue obtained (400 mg) by means of chromatographic purification [silica gel 60 (50 g); ethyl acetate (500 ml)].

Step 2:

2-Allyl-N,N-dimethyl-4-phenyl-4',9'-dihydros-3'H-spiro[cyclohexane-1,1'-pyrano[3,4-b]indole]-4-amine hydroxypropane-1,2,3-tricarboxylic acid (Example No. 18, from the More Non-polar Ketone, One of 4 Possible Racemic Diastereoisomer Pairs)

To produce the citrate, the 2-allyl-N,N-dimethyl-4-phenyl-4',9'-dihydros-3'H-spiro[cyclohexane-1,1'-pyrano[3,4-b]indole]-4-amine from step 1 (290 mg, 0.72 mmol) was dissolved in hot isopropanol (80 ml) and mixed with a likewise hot isopropanol citric acid solution (140 mg, 0.72 mmol in 3 ml). The reaction mixture was then placed in the refrigerator. The solid obtained was aspirated. The citrate was thus obtained as a white solid (melting point: 233-236° C.) with a yield of 157 mg (37%).

Example No. 18: $^{13}$C-NMR (101 MHz, DMSO-d$_6$) δ ppm: 22.1, 27.9, 29.4, 32.5, 34.2, 37.9, 38.9, 42.9, 59.1, 59.4, 72.2, 74.5, 106, 111.3, 115.9, 117.4, 118.3, 120.4, 126.4, 126.5, 127.4, 136.0, 137.7, 137.8, 139.2, 171.3, 175.0

Example No. 19 and Example No. 20 and Example No. 21

Step 1:

2-Fluoro-N,N-dimethyl-4-phenyl-4',9'-dihydro-3'H-spiro[cyclohexane-1,1'-pyrano[3,4-b]indole]-4-amine (Example No. 19, Mon-polar Diastereomer and Example No. 20, Average Diastereomer and Example No. 21, Polar Diastereomer)

(±)-4-dimethylamino-2-fluoro-4-phenylcyclohexanone (1.61 g, 6.83 mmol, mixture of both diastereoisomers, mainly polar diastereoisomer) together with tryptophol (1.10 g, 6.83 mmol) was dissolved in absolute dichloromethane (75 ml) at 0° C. (inside temperature). Trimethylsilyl triflate (1.67 g, 7.51 mmol, 1.36 ml, 1.225 g/ml) was then added quickly in drops to absolute dichloromethane (10 ml). The reaction mixture immediately changed colour from yellow to red-brown. The reaction mixture was stirred for 5 h at room temperature and became cloudy during this. 5N sodium hydroxide solution (100 ml) was added to the reaction mixture and stirred for 10 min. After phase separation the aqueous phase was extracted with dichloromethane (4×50 ml). The combined organic phases were dried over sodium sulphate, filtered and then completely freed of volatile constituents in a vacuum. An attempt was made to separate the residue by chromatography [silica gel (150 g), chloroform/ethanol 50:1 (500 ml), 19:1 (500 ml), 9:1 (1000 ml), 1:1 (500 ml), methanol (1000 ml)]. 467 mg (1.23 mmol, 18%, mp 259-263° C.) of a more non-polar diastereomer, 506 mg (1.34 mmol, 20%, mp 217-222° C.) of a diastereomer of average polarity and 168 mg (0.44 mmol, 6%, mp 245-247° C.) of a more polar diastereoisomer were isolated. The individual fractions were recrystallised from methanol.

Example No. 19: $^{13}$C {$^1$H}-NMR (101 MHz, DMSO-D$_6$) δ ppm (more non-polar diastereoisomer): 21.9 (1 C), 27.2 (1 C), 28.2 (1 C), 33.3 (1 C, d, J=18 Hz), 38.4 (2 C), 58.5 (1 C), 60.0 (1 C), 72.6 (1 C, J=22 Hz), 92.1 (1 C, d, J=181 Hz), 106.5 (1 C), 111.7 (1 C), 117.6 (1 C), 118.3 (1 C), 120.7 (1 C), 125.8 (1 C), 126.5 (2 C), 127.4 (2 C), 128.2 (1 C, d, J=26 Hz), 135.0 (1 C), 136.2 (1 C), 137.7 (1 C)

Example No. 20: $^{13}$C {$^1$H}-NMR (101 MHz, DMSO-D$_6$) δ ppm (diastereoisomer of average polarity): 21.8 (1 C), 26.6 (1 C), 30.6 (1 C, d, J=5 Hz), 33.3 (1 C, d, J=19 Hz), 38.0 (2 C), 60.7 (1 C), 62.4 (1 C, d, J=13 Hz), 73.6 (1 C, J=16 Hz), 92.5 (1 C, d, J=182 Hz), 107.7 (1 C), 111.0 (1 C), 117.6 (1 C), 118.3 (1 C), 120.8 (1 C), 126.4 (1 C, d, J=8 Hz), 126.8 (1 C), 127.3 (2 C), 127.9 (2 C), 134.4 (1 C), 135.9 (1 C), 136.2 (1 C)

Example No. 21: $^{13}$C {$^1$H}-NMR (101 MHz, DMSO-D$_6$) δ ppm (more polar diastereoisomer): 21.4 (1 C), 27.3 (1 C), 31.3 (1 C, d, J=5 Hz), 33.9 (1 C, d, J=20 Hz), 38.7 (2 C), 61.4 (1 C), 63.2 (1 C, br, d, J=15 Hz), 74.3 (1 C, J=16 Hz), 93.2 (1 C, d, J=182 Hz), 108.4 (1 C), 111.7 (1 C), 118.2 (1 C), 119.1 (1 C), 121.5 (1 C), 127.5 (1 C), 127.0 (1 C), 128.1 (2 C), 128.6 (2 C), 135.1 (1 C), 136.4 (1 C, br), 136.6 (1 C)

Example No. 22 and Example No. 23

Step 1:

2,6'-Difluoro-N,N-dimethyl-4-phenyl-4',9'-dihydro-3'H-spiro[cyclohexane-1,1'-pyrano[3,4-b]indole]-4-amine (Example No. 22, More Non-polar Diastereomer and Example No. 23, More Polar Diastereomer)

The more polar 4-dimethylamino-2-fluoro-4-phenylcyclohexanone (950 mg, 4.04 mmol) together with tryptophol (723 mg, 4.04 mmol) was dissolved in absolute dichloromethane (45 ml) at 0° C. (inside temperature). Trimethylsilyl triflate (987 mg, 4.44 mmol, 0.81 ml, 1.225 g/ml) was then added quickly in drops to absolute dichloromethane (10 ml). The reaction mixture immediately changed colour from yellow to red-brown. The reaction mixture was stirred for 5 h at room temperature and became cloudy during this. 5N sodium hydroxide solution (60 ml) was added to the reaction mixture and stirred for 10 min. A colourless solid separated out of the two-phase mixture. This was filtered off by means of a fritted glass filter and then washed with methanol (50 ml). The solid was the more polar diastereoisomer (241 mg). The more polar diastereoisomer was separated from the filtrate again and filtered off once again. After phase separation the aqueous phase was extracted with dichloromethane (4×40 ml). The combined organic phases were dried over sodium sulphate, filtered and then completely freed of volatile constituents in a vacuum. An attempt was made to separate the residue by chromatography [silica gel (150 g), chloroform/ethanol 19:1 (1000 ml), methanol (500 ml)]. 676 mg (1.70 mmol, 42%, mp 260-265° C.) of a more non-polar diastereomer and a total of 572 mg (1.44 mmol, 36%, mp 237-242° C.) of the more polar diastereoisomer were isolated.

Example No. 22: $^{13}$C {$^1$H}-NMR (101 MHz, DMSO-D$_6$) δ ppm (more non-polar diastereoisomer): 21.8 (1 C), 27.2 (1 C), 28.1 (1 C), 33.2 (1 C, d, J=18 Hz), 38.3 (2 C), 58.5 (1 C), 60.0 (1 C), 72.5 (1 C, J=22 Hz), 92.0 (1 C, d, J=179 Hz), 102.3 (1 C, d, J=23 Hz), 106.9 (1 C, d, J=5 Hz), 108.7 (1 C, d, J=26 Hz), 112.5 (1 C, d, J=10 Hz), 125.9 (1 C, d, J=10 Hz), 126.4

(1 C), 126.5 (2 C), 127.3 (2 C), 132.8 (1 C), 137.0 (1 C), 137.6 (1 C), 156.7 (1 C, d, J=231 Hz)

Example No. 23: $^{13}C\{^1H\}$-NMR (101 MHz, DMSO-$D_6$) δ ppm (more polar diastereoisomer): 21.7 (1 C), 26.6 (1 C), 30.5 (1 C, d, J=Hz), 33.3 (1 C, d, J=19 Hz), 38.0 (2 C), 60.6 (1 C), 62.4 (1 C, d, J=13 Hz), 73.6 (1 C, J=16 Hz), 92.5 (1 C, d, J=182 Hz), 102.4 (1 C, d, J=23 Hz), 108.1 (1 C, d, J=5 Hz), 108.6 (1 C, d, J=0.26 Hz), 111.8 (1 C, d, J=10 Hz), 126.5 (1 C, d, J=10 Hz), 126.8 (1 C), 127.3 (2 C), 127.9 (2 C), 132.5 (1 C), 135.7 (1 C), 136.6 (1 C), 156.7 (1 C, d, J=231 Hz)

Example No. 24

Step 1:

2,6'-Difluoro-N,N-dimethyl-4-phenyl-4',9'-dihydro-3'H-spiro[cyclohexane-1,1'-pyrano[3,4-b]indole]-4-amine (Example No. 24, a Diastereomer)

The more non-polar 4-dimethylamino-2-fluoro-4-phenyl-cyclohexanone (400 mg, 1.70 mmol) together with 5-fluorotryptophol (305 mg, 1.70 mmol) was dissolved in absolute dichloromethane (20 ml) at 0° C. (inside temperature). Trimethylsilyl triflate (416 mg, 1.87 mmol, 0.34 ml, 1.225 g/ml) was then added quickly in drops to absolute dichloromethane (10 ml). The reaction mixture immediately changed colour from yellow to red-brown. The reaction mixture was stirred for 48 h at room temperature and became cloudy during this. 5N sodium hydroxide solution (60 ml) was then added and the mixture was stirred for 10 min. After phase separation the aqueous phase was extracted with dichloromethane (4×40 ml). The combined organic phases were dried over sodium sulphate, filtered and then completely freed of volatile constituents in a vacuum. The residue was separated chromatographically [silica gel 60 (80 g), trichloromethane/ethanol 19:1 (500 ml); trichloromethane/ethanol 9:1 (1000 ml), trichloromethane/ethanol 9:1+1% aqueous ammonia solution (1000 ml), methanol+1% aqueous ammonia solution (500 ml)]. One of the two possible diastereoisomers (50 mg, 0.13 mmol, 7%) could be isolated as colourless solid (mp 258-264° C.).

Example No. 24: $^{13}C\{^1H\}$-NMR (101 MHz, DMSO-$D_6$, δ ppm, AS 03391): 21.7 (1 C), 27.2 (1 C), 29.9 (1 C, d, J=4 Hz), 33.2 (1 C, d, J=20 Hz), 37.9 (2 C), 60.6 (1 C), 61.4 (1 C, d, J=12), 73.6 (1 C, J=16 Hz), 92.4 (1 C, d, J=180 Hz), 102.5 (1 C, d, J=23 Hz), 108.0 (1 C, d, J=5 Hz), 108.6 (1 C, d, J=26 Hz), 112.0 (1 C, d, J=10 Hz), 126.4 (2 C), 126.7 (1 C), 126.8 (1 C), 127.4 (2 C), 132.7 (1 C), 137.2 (1 C), 138.2 (1 C), 156.7 (1 C, d, J=231 Hz)

Example No. 25 and Example No. 26 and Example No. 27 and Example No. 28

Step 1:

2-Fluoro-N,N-dimethyl-4-phenyl-2',3',4',9'-tetrahydrospiro[cyclohexane-1,1'-pyrido[3,4-b]indole]-4-amine (Example No. 25, Example No. 26, Example No. 27, Example No. 28, 4 Racemic Diastereoisomer Pairs)

Conversion of the More Non-polar 4-Dimethylamino-2-fluoro-4-phenylcyclohexanone

The more non-polar 4-dimethylamino-2-fluoro-4-phenyl-cyclohexanone (481 mg, 2.04 mmol) and tryptamine (327 mg, 2.04 mmol) were dissolved in dry methanol (25 ml) in an argon atmosphere and the reaction mixture formed stirred for 12 h. The methanol was then completely removed in a vacuum and the residue suspended in 1,2-dichloroethane (25 ml). The reaction mixture was mixed with trifluoroacetic acid (2.5 ml) and stirred for 2 h at room temperature. The reaction mixture was diluted with water (50 ml) and 1,2-dichloroethane (25 ml). Under ice cooling the pH value of the reaction mixture was adjusted to pH 11 with 1N sodium hydroxide solution and stirred for 1 h. Scarcely any precipitate was formed. No residue was left behind during separation by means of a fritted glass filter. The phases were separated. The organic phase was dried with sodium sulphate and then completely freed of volatile constituents in a vacuum. The residue was separated chromatographically [silica gel 60 (80 g), ethyl acetate/methanol 2:1 (1000 ml); methanol (500 ml), tetrahydrofuran (500 ml)]. The ketone isomerised during the reaction and therefore more than two diastereoisomers of the target compound could be isolated. A mixture of two diastereoisomers (9%, 71 mg, 0.189 mmol, mp 206-236° C.) was isolated, on the one hand (Example No. 28). A more non-polar diastereoisomer (81 mg, 0.21 mmol, 10%, mp 197-237° C.) could be additionally isolated (Example No. 25). In addition, a more polar diastereoisomer (73 mg, 0.19 mmol, 9%, mp 180-182° C.) was isolated (Example No. 26).

Conversion of the More Polar 4-Dimethylamino-2-fluoro-4-phenylcyclohexanone

The more polar 4-dimethylamino-2-fluoro-4-phenylcyclohexanone (1.47 g, 6.27 mmol) and tryptamine (1.00 g, 6.27 mmol) were dissolved in dry methanol (63 ml) in an argon atmosphere and the reaction mixture formed stirred for 10 h. The methanol was then completely removed in a vacuum and the residue suspended in dry 1,2-dichloroethane (63 ml). The reaction mixture was mixed with trifluoroacetic acid (6.3 ml) and stirred for 2 h at room temperature. The reaction mixture was diluted with water (50 ml) and 1,2-dichloroethane (25 ml). The pH value of the reaction mixture was adjusted to pH 11 with 1N sodium hydroxide solution under ice cooling. A precipitate was formed. The mixture was stirred for 1 h. The precipitate was separated by means of a fritted glass filter. Since the precipitate was not uniform according to NMR, it was separated by means of a flash chromatography [silica gel 60 (80 g); ethyl acetate/methanol 2:1 (1000 ml), methanol (500 ml), tetrahydrofuran (500 ml)]. The ketone isomerised during the reaction. Therefore more than two possible diastereoisomers could be isolated. A mixture of two diastereoisomers was thus isolated with a yield of 1% (20 mg, 0.05 mmol) (Example No. 28). A further more non-polar diastereoisomer (122 mg, 0.32 mmol, 5%, Example No. 25) was isolated. In addition, a mixture of two diastereoisomers could also be isolated (6%, 145 mg, 0.38 mmol). The phases of the filtrate were separated. The organic phase was dried with sodium sulphate, filtered and freed of volatile constituents in a vacuum. The residue was separated chromatographically [silica gel 60 (80 g), ethyl acetate/methanol 2:1 (1000 ml); methanol (500 ml), tetrahydrofuran (500 ml)]. The more polar of the two diastereoisomers was isolated from the mixture (Example No. 28) (84 mg, 0.22 mmol, 4%, mp 239-247° C., Example No. 27). A more non-polar diastereoisomer (241 mg, 0.64 mmol, 10%) could also be isolated (Example No. 25). In addition, a more polar diastereoisomer (163 mg, 0.43 mmol, 7%) was isolated (Example No. 26).

Example No. 25: $^{13}$C-NMR (101 MHz, DMSO-$D_6$, δ ppm, a diastereoisomer): 22.5 (1 C), 26.4 (1 C), 31.4 (1 C, d, J=6 Hz), 32.8 (1 C, d, J=19 Hz), 38.0 (2 C), 55.1 (1 C, d, J=16 Hz), 62.7 (1 C, d, 13 Hz), 93.9 (1 C, J=178 Hz), 109.2 (1 C), 110.9 (1 C), 117.3 (1 C), 118.0 (1 C), 120.5 (1 C), 126.7 (1 C), 127.0 (1 C), 127.4 (2 C), 127.9 (2 C), 135.7 (1 C), 136.3 (1 C), 136.9 (1 C), n.b. (1 C)

Example No. 26: $^{13}$C-NMR (101 MHz, DMSO-D$_6$, δ ppm, a diastereoisomer): 22.6 (1 C), 26.5 (1 C), 29.9 (1 C), 33.7 (1 C, d, J=19 Hz), 37.6 (2 C), 53.7 (1 C, d, J=20 Hz), 59.5 (1 C, d, 2 Hz), 94.2 (1 C, J=174 Hz), 108.2 (1 C), 111.3 (1 C), 117.3 (1 C), 117.9 (1 C), 120.3 (1 C), 126.1 (1 C), 126.3 (1 C), 127.0 (2 C), 127.3 (2 C), 135.7 (1 C), 136.7 (1 C), 137.0 (1 C), n.b. (1 C)

Example No. 27: $^{13}$C-NMR (101 MHz, DMSO-D$_6$, δ ppm, identical to the more polar diastereoisomer from Example No. 28): 22.6 (1 C), 27.1 (1 C), 30.4 (1 C), 30.7 (1 C, d, J=5 Hz), 32.9 (1 C, d, J=19 Hz), 38.0 (2 C), 55.1 (1 C, d, J=16 Hz), 61.6 (1 C, d, 12 Hz), 93.7 (1 C, J=176 Hz), 109.0 (1 C), 111.1 (1 C), 117.4 (1 C), 118.1 (1 C), 120.5 (1 C), 126.4 (2 C), 126.5 (1 C), 127.0 (1 C), 127.3 (2 C), 135.8 (1 C), 137.5 (1 C), 138.6 (1 C)

Example No. 29

Step 1:

4-(Dimethylamino)-4-phenyl-4',9'-dihydro-3'H-spiro [cyclohexane-1,1'-pyrano[3,4-b]indole]-2-yl)methanol (Example No. 29, One of 4 Possible Racemic Diastereoisomer Pairs)

2-(4-(dimethylamino)-4-phenyl-4',9'-dihydro-3'H-spiro [cyclohexane-1,1'-pyrano[3,4-b]indole]-2-yl)methyl acetate (Example No. 16, one of 4 possible racemic diastereoisomer pairs) (190 mg, 0.44 mmol) was dissolved in a mixture of 2N HCl (20 ml) and ethanol (20 ml) and stirred for 18 h at RT. For work up the ethanol was extracted in a vacuum, the aqueous residue neutralised with NaHCO$_3$ and strongly basified with 2N NaOH. The aqueous solution was extracted with ethyl acetate (3×10 ml). The combined organic phases were dried over MgSO$_4$ and then concentrated to low volume. The solid residue obtained proved to be one of the four possible diastereoisomers of the desired alcohol in pure form. The product was thus obtained with a yield of 153 mg (89%) with a melting point of 219-233° C. (from propan-2-ol).

Example No. 29: $^{13}$C-NMR (101 MHz, DMSO-d$_6$, δ ppm): 22.1, 27.9, 30.5, 31.0, 37.9, 43.9, 59.1, 60.8, 61.6, 73.8, 106.5, 111.0, 117.3, 118.2, 120.4, 126.2, 126.3, 127.59, 127.63, 135.9, 136.6, 137.4

Example No. 30

Step 1:

2-(4-(Dimethylamino)-4-phenyl-4',9'-dihydro-3'H-spiro[cyclohexane-1,1'-pyrano[3,4-b]indole]-2-yl) ethanol (Example No. 30, One of 4 Possible Racemic Diastereoisomer Pairs)

The more polar 2-(4-(dimethylamino)-4-phenyl-4',9'-dihydro-3'H-spiro[cyclohexane-1,1'-pyrano[3,4-b]indole]-2-yl)methyl acetate (254 mg, 0.58 mmol) was dissolved in dry THF (20 ml) and mixed in portions with LiAlH$_4$ (50 mg, 1.16 mmol) within 10 min at RT. After the addition had finished, the batch was stirred for 90 min at RT. For work up excess LiAlH$_4$ was broken down by adding moist THF (2 ml of a mixture of water (approx. 0.3 ml) and THF (2 ml)). The mixture obtained was passed onto a fritted glass filter with silica gel (layer height approx. 2 cm) and the filter cake was washed with ethyl acetate (3×30 ml) and tetrahydrofuran (3×30 ml). The filtrate was concentrated until dry. The solid (230 mg) obtained in this way was the desired racemic diastereoisomer pair. The desired alcohol could thus be isolated with a yield of 230 mg (98%, decomposition from 215° C.).

Example No. 30: $^{13}$C-NMR (101 MHz, DMSO-d$_6$) δ ppm: 22.1, 27.5, 30.4, 31.0, 33.0, 33.4, 34.3, 37.9, 38.3, 59.0, 59.5, 61.0, 74.8, 106.8, 111.1, 117.3, 118.1, 120.3, 124.8, 126.2, 126.4, 127.5, 127.6, 135.8, 136.7, 137.8, 139.1

Example No. 31

Step 1:

2-(4-(Dimethylamino)-4-phenyl-4',9'-dihydro-3'H-spiro[cyclohexane-1,1'-pyrano[3,4-b]indole]-2-yl) ethanol (Example No. 31, One of 4 Possible Racemic Diastereoisomer Pairs)

2-(4-(dimethylamino)-4-phenyl-4',9'-dihydro-3'H-spiro [cyclohexane-1,1'-pyrano[3,4-b]indole]-2-yl)methyl acetate (279 mg, 0.65 mmol) was dissolved in dry THF (20 ml) and mixed in portions with LiAlH$_4$ (50 mg, 1.32 mmol) within 10 min at RT. After the addition had finished, the batch was stirred for 90 min at RT. For work up excess LiAlH$_4$ was broken down by adding moist THF (2 ml of a mixture of water (approx. 0.3 ml) and THF (2 ml)). The mixture obtained was passed to a fritted glass filter with silica gel (layer height approx. 2 cm) and the filter cake was washed with ethyl acetate (3×30 ml). A solid was separated from the filtrate, and also remained in the organic phase during shaking out with 2N NaOH. The solid was separated from the solvent mixture by filtration. A first batch of the desired racemic diastereoisomer pair could thus be obtained with a yield of 77 mg and with a melting point of 311-314° C. (crystal transformation from 280° C.). The organic phase of the mother liquor was separated from the solvent mixture and concentrated to low volume. The residue formed was rubbed with chloroform (1 ml) and the crystals formed were isolated by means of a fritted glass filter. The solid obtained in this way was likewise the desired alcohol that could thus be isolated with a total yield of 130 mg (49%).

Example No. 31: $^{13}$C-NMR (101 MHz, DMSO-d$_6$) δ ppm: 22.2, 27.9, 29.5, 33.1, 33.9, 36.5, 38.0, 58.6, 59.0, 59.7, 74.9, 106.7, 111.1, 117.3, 118.1, 120.3, 126.2, 126.4, 127.2, 136.0, 138.4, 139.8

Example No. 32

Step 1:

2-(4-(Dimethylamino)-4-phenyl-4',9'-dihydro-3'H-spiro[cyclohexane-1,1'-pyrano[3,4-b]indole]-2-yl) methyl)isoindoline-1,3-dione (Example No. 32, One of Four Possible Diastereoisomers)

Trypthophol (97 mg, 0.6 mmol) together with the 2-(5-dimethylamino-2-oxo-5-phenylcyclohexylmethyl)isoindoline-1,3-dione (220 mg, 0.6 mmol) was provided in dichloromethane (20 ml) with the exclusion of moisture and quickly mixed with trifluoromethane sulphonic acid trimethylsilyl ester (0.26 ml, 1.44 mmol). The batch was stirred for 24 h at RT. For work up of the batch the mixture was mixed with 2N sodium hydroxide solution (10 ml) and stirred for 15 min. The aqueous phase was extracted with dichloromethane (2×30 ml). The combined organic phases were concentrated to low volume after drying (Na$_2$SO$_4$), wherein a brown oil (300 mg) was obtained. After adding methanol (3 ml) a white sold was precipitated, which was aspirated and then dried. One of the four possible diastereoisomers could thus be obtained with a yield of 100 mg (32%) and a with melting point of 148-166° C.

Example No. 32: $^{13}$C NMR (101 MHz, CDCl$_3$, δ ppm, AS 05791): 22.0, 27.8, 29.2, 32.0, 37.7, 37.9, 38.4, 58.5, 59.4, 73.2, 106.9, 111.1, 117.1, 117.9, 120.3, 122.3, 126.1, 126.3, 127.3, 131.1, 133.7, 136.1, 136.8, 139.4, 167.6

Example No. 33

Step 1:

2-(Aminomethyl)-4-(3-fluorophenyl)-N,N-dimethyl-4',9'-dihydro-3'H-spiro[cyclohexane-1,1'-pyrano[3,4-b]indole]-4-amine (One of Four Possible Diastereoisomers)

Hydrazine hydrate (97 μl, 1.99 mmol) was added under agitation to a solution of 2-(4-(dimethylamino)-4-phenyl-4',9'-dihydro-3'H-spiro[cyclohexane-1,1'-pyrano[3,4-b]indole]-2-yl)methyl)isoindoline-1,3-dione (190 mg, 0.35 mmol, Example No. 31) in methanol (50 ml) at room temperature. The batch was stirred for 2 d at 150° C. in a Teflon vessel and then mixed with H$_2$O (50 ml). The methanol contained in the solvent mixture was distilled off on a rotary evaporator. The aqueous residue was extracted with ethyl acetate (3×20 ml). The combined organic phases were dried over Na$_2$SO$_4$ and then concentrated to low volume. The oily residue (130 mg, 90% yield) proved to be a substantially uniform product in NMR.

Step 2:

N-((4-(dimethylamino)-4-(3-fluorophenyl)-4',9'-dihydro-3'H-spiro[cyclohexane-1,1'-pyrano[3,4-b]indole]-2-yl)methyl)-3-phenylcinnamic acid amide (Example No. 33, One of Four Possible Diastereoisomers)

2-(aminomethyl)-4-(3-fluorophenyl)-N,N-dimethyl-4',9'-dihydro-3'H-spiro[cyclohexane-1,1'-pyrano[3,4-b]indole]-4-amine (130 mg, 0.31 mmol) was dissolved in absolute tetrahydrofuran (20 ml) with argon. Hünig's base (0.1 ml, 0.63 mmol) and cinnamic acid chloride (105 mg, 0.63 mmol) dissolved in absolute tetrahydrofuran (8 ml) were added one after the other to the clear solution at room temperature. After a reaction time of 45 min, the batch was mixed with water (10 ml) and 2 N sodium hydroxide solution (10 ml) and stirred for 1 h. For work up tetrahydrofuran was distilled off completely. The aqueous mixture was extracted with dichloromethane (3×20 ml). The combined organic extracts were washed once again with water (20 ml), dried over Na$_2$SO$_4$ and concentrated to low volume. The raw product (247 mg) was separated by chromatography [silica gel 60 (30 g); ethyl acetate/cyclohexane 5:1 (600 ml)]. One of four possible diastereoisomers was obtained as white solid with a yield of 108 mg (65%) and with a melting point of 134-140° C.

Example No. 33: $^{13}$C NMR (101 MHz, DMSO-d$_6$, δ ppm): 22.2, 28.0, 29.3, 30.4, 31.7, 37.9, 58.6, 59.3, 74.0, 106.7, 111.4, 112.9, 113.1, 113.4, 117.4, 118.2, 120.4, 122.3, 122.5, 126.3, 127.4, 128.8, 129.0, 129.2, 134.9, 136.2, 137.4, 138.2, 142.9, 142.9, 160.7, 163.1, Example No. 34

Step 1:

Tert-butyl 2-(2-(4-(dimethylamino)-4-phenyl-4',9'-dihydro-3'H-spiro[cyclohexane-1,1'-pyrano[3,4-b]indole]-2-yl)ethoxy)acetate (Example No. 34, one of 4 Possible Diastereoisomers, From More Non-polar Ketone)

50% aqueous sodium hydroxide solution (15 ml) was added to a solution of 2-(4-(dimethylamino)-4-phenyl-4',9'-dihydro-3'H-spiro[cyclohexane-1,1'-pyrano[3,4-b]indole]-2-yl)ethanol (285 mg, 0.7 mmol) and tetra-n-butyl ammonium bromide (10 mg, 0.03 mmol) in tetrahydrofuran (20 ml) at 0° C. A solution of bromoacetic acid tert-butyl ester (275 mg, 208 μl, 1.4 mmol) in tetrahydrofuran (2 ml) was then added in drops also at 0° C. The heterogeneous mixture was stirred for 24 h at room temperature. A solution of bromoacetic acid tert-butyl ester (550 mg, 416 μl, 2.8 mmol) in tetrahydrofuran (2 ml) was then once again added in drops and stirred for 24 h at room temperature. For work up the aqueous phase was separated and the organic phase washed neutrally with water (4×30 ml). The organic phase was dried with sodium sulphate and concentrated to low volume in a vacuum. One of the four possible diastereoisomers was isolated from the residue obtained (410 mg) as an oil with a yield of 30 mg (8%) by means of chromatographic purification [silica gel 60 (30 g); ethyl acetate (500 ml)].

Example No. 34: $^{13}$C-NMR (101 MHz, CDCl$_3$, δ ppm): 22.4, 28.1, 28.2, 29.9, 34.1, 36.1, 38.1, 59.6, 59.7, 68.5, 69.9, 75.0, 81.5, 108.2, 111.2, 117.8, 119.0, 121.5, 126.5, 126.9, 127.3, 136.0, 138.3, 139.6, 169.9

Example No. 35 and Example No. 36

Step 1:

2-(4-(Dimethylamino)-4-phenyl-4',9'-dihydro-3'H-spiro[cyclohexane-1,1'-pyrano[3,4-b]indole]-2-yl)acetonitrile (Example No. 35, Non-polar Diastereomer and Example No. 36, Polar Diastereomer)

(±)-3-(5-dimethylamino-2-oxo-5-phenylcyclohexyl)propionitrile (400 mg, 1.48 mmol) together with tryptophol (238 mg, 1.48 mmol) was dissolved in dichloromethane (20 ml) and mixed with trifluoromethane sulphonic acid trimethylsilyl ester (0.3 ml, 1.66 mmol). The batch was stirred for 18 h at RT. For work up the reaction solution was mixed with 2N NaOH (10 ml) and stirred for 20 min. The organic phase was separated and the aqueous phase extracted with dichloromethane (3×20 ml). The combined organic phases were dried with MgSO$_4$. The solvent was then removed in a vacuum. The residue (601 mg) was mixed with methanol (20 ml), wherein a clear solution was formed. The solution was concentrated to about half its volume and left for 2 h at 5° C. The precipitate obtained was separated by means of a fritted glass filter and dried in a vacuum. A more non-polar diastereoisomer could thus be isolated in a first batch (254 mg, 41%) as beige solid with a melting point of 208-213° C. The crystals contained about 1 equivalent of methanol. A more polar diastereoisomer was also present in the evaporated down residue of the mother liquor (390 mg) besides further more non-polar product. Further more non-polar racemic diastereoisomer [61 mg (after recrystallisation from methanol), [total yield 51%] as well as the polar racemic diastereoisomer (29 mg, 4%, melting point 260-267° C.) could be isolated by means of column chromatography [silica gel 60 G (10 g); cyclohexane/ethyl acetate 1:1 (120 ml), ethyl acetate (100 ml), ethyl acetate/ethanol 1:1 (100 ml)].

Example No. 35: $^{13}$C-NMR (101 MHz, CDCl$_3$, δ ppm): 15.4, 22.5, 25.9, 28.1, 29.6, 33.4, 38.2, 38.8, 59.4, 59.8, 74.5, 108.8, 111.3, 118.0, 119.5, 120.2, 121.8, 126.77, 126.79, 127.5, 135.8, 137.1, 138.9

Example No. 36: $^{13}$C-NMR (101 MHz, CDCl$_3$, δ ppm): 15.1, 22.3, 26.1, 27.4, 31.5, 32.7, 38.3, 40.9, 59.8, 61.7, 74.3, 109.2, 111.1, 118.0, 119.6, 120.0, 121.9, 126.7, 127.1, 127.9, 128.3, 135.7, 136.2

Studies on the Efficacy of the Compounds According to the Invention

Measurement of the ORL 1-Bond

The compounds were examined with membranes of recombinant CHO-ORL 1 cells in a receptor binding assay with $^3$H-nociceptine/orphanin FQ. This test system was conducted in accordance with the method outlined by Ardati et al. (Mol. Pharmacol., 51, 1997, pp. 816-824). The concentration of $^3$H-nociceptine/orphanin FQ amounted to 0.5 nM in these tests. The binding assays were conducted in each case on 20 μg of membrane protein per 200 μl of preparation in 50 mM of HEPES, pH 7.4, 10 nM of MgCl$_2$ and 1 mM of EDTA. The binding to the ORL 1-receptor was determined using 1 mg of WGA-SPA beads (Amersham-Pharmacia, Freiburg) in each case by incubating the preparation for one hour at RT and then conducting measurements in the Trilux scintillation counter (Wallac, Finland). The affinity is indicated as nanomolar K$_i$ value or in % inhibition at c=1 μM in Table 1.

Measurement of the μ-Bond

The affinity to the human μ-opiate receptor was determined in a homogeneous preparation in microtiter plates. For this, dilution series of the respective compound to be tested were incubated for 90 minutes at room temperature with a receptor membrane preparation (15-40 μg of protein per 250 μl of incubation batch) of CHO-K1 cells, which express the human μ-opiate receptor (RB-HOM receptor membrane preparation of NEN, Zaventem, Belgium), in the presence of 1 nmol/l of the radioactive ligand [$^3$H']-naloxone (NET719, NEN, Zaventem, Belgium) and of 1 mg WGA-SPA beads (wheat germ agglutinin SPA beads from Amersham/Pharmacia, Freiburg, Germany) in a total volume of 250 μl. 50 mmol/l of tris-HCl supplemented by 0.05% by wt. of sodium azide and 0.06% by wt. of bovine serum albumin was used as incubation buffer. 25 μmol/l of naloxone were additionally added to determine the non-specific bond. After the ninety-minute incubation time had ended, the microtiter plates were centrifuged for 20 minutes at 1000 g and the radioactivity measured in a β-counter (Microbeta-Trilux, PerkinElmer Wallac, Freiburg, Germany). The percentage displacement of the radioactive ligand from its binding to the human μ-opiate receptor was determined with a concentration of the test substances of 1 μmol/l and was specified as percentage inhibition (% inhibition) of the specific bond. In some instances, working from the percentage displacement by different concentrations of the compounds of the general formula I according to the invention, IC$_{50}$ inhibition concentrations were calculated that effect a 50 percent displacement of the radioactive ligand. Ki values for the test substances were obtained by conversion using the Cheng-Prusoff equation. In some cases, the determination of the Ki value was omitted and only the inhibition with a test concentration of 1 μM was determined.

Nephelometric Solubility Study (Phosphate Buffer pH 7.4):

This method examines the solubility of a substance with fixed concentrations (1 μM, 3 μM, 10 μM, 30 μM and 100 μM) in 10 mM of phosphate buffer solution with pH 7.4. A 10 mM solution of the substances in DMSO will be initially required, from which 100-fold stock solutions of the above-mentioned concentration level again in DMSO are produced, the final DMSO concentration in the test batch amounting to 1% (v/v). The experiment is conducted multiple times for determination. After the DMSO stock solutions have been added to the buffer, the batch is incubated for 2 h at 37° C. before an absorption determination at 620 nm occurs. If the absorption of the samples increases above that of the pure buffer/DMSO solution, then this applies as indicator for a precipitate formation. The lower solubility limit ("lower boundary") is the concentration preceding that with the first precipitate formation (e.g. 3 μM if precipitation formation was detected at 10 μM).

| No. | % Inhibition (ORL1) [1 μM] | Ki (ORL1) Mean [μM] | % Inhibition (μ) [1 μM] | Ki (μ) Mean [μM] |
|---|---|---|---|---|
| Ex. 1 | 99 | 0.001 | 77 | 0.001 |
| Ex. 2 | 97 | 0.006 | 106 | 0.02 |
| Ex. 3 | 50 | 0.23 | 84 | 0.086 |
| Ex. 5 | 93 | n.d. | 96 | n.d. |
| Ex. 8 | 92 | 0.053 | 100 | 0.22 |
| Ex. 9 | 97 | 0.107 | 103 | 0.098 |
| Ex. 10 | nd | 0.016 | nd | 0.021 |
| Ex. 11 | 53 | nd | 90 | nd |
| Ex. 12 | 73 | 2.05 | 88 | 0.11 |
| Ex. 14 | 94 | 0.006 | 101 | 0.003 |
| Ex. 15 | 33 | 0.335 | 68 | 0.165 |
| Ex. 16 | 50 | 0.34 | 75 | 0.215 |
| Ex. 17 | 54 | 0.62 | 93 | 0.45 |
| Ex. 18 | 89 | 0.026 | 97 | 0.003 |
| Ex. 20 | 96 | nd | 96 | nd |
| Ex. 21 | 76 | nd | 99 | nd |
| Ex. 22 | 90 | nd | nd | nd |
| Ex. 23 | 29 | 2.815 | nd | 0.12 |
| Ex. 24 | 68 | nd | 99 | nd |
| Ex. 25 | 87 | 0.027 | 100 | 0.017 |
| Ex. 26 | 58 | nd | 87 | nd |
| Ex. 27 | 95 | nd | 102 | nd |
| Ex. 28 | 98 | nd | 99 | nd |
| Ex. 29 | 80 | 0.063 | 99 | 0.067 |
| Ex. 30 | 96 | 0.007 | 100 | 0.021 |
| Ex. 31 | 94 | 0.014 | 99 | 0.002 |
| Ex. 32 | 83 | nd | 101 | nd |
| Ex. 33 | 83 | 0.07 | 97 | 0.013 |

The compounds according to the invention of type I with X=O or —NH, R$_6$=H and Y$_3$≠H (Ex. 29, 30 and 25) were compared with corresponding compounds of type I with X=O or —NH, R$_6$=H and Me and Y$_3$=H(C-1 and C-2):

| Ex. | X | Y$_3$ | R$_3$ | R$_6$ | Nephelometry (lower boundary) μM |
|---|---|---|---|---|---|
| 30 | O | CH$_2$CH$_2$OH | phenyl | H | 30 |
| 29 | O | CH$_2$OH | phenyl | H | 10 |
| C-1: | O | H | 3-hydroxyphenyl | H | 1 |
| 25 | NH | F | phenyl | H | 100 |
| C-2: | NH | H | phenyl | Me | 10 |

As the above comparison shows, the compounds according to the invention exhibit a better solubility in aqueous media than structurally similar spiro compounds (Y$_3$=H), and this should be associated in particular with advantages with respect to the resorption properties and/or bioavailability.

The invention claimed is:

1. A compound of the formula (1):

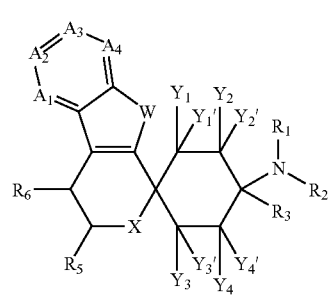

(1)

wherein
$A_1$ stands for —N= or —CR$_7$=,
$A_2$ stands for —N= or —CR$_8$=,
$A_3$ stands for —N= or —CR$_9$=,
$A_4$ stands for —N= or —CR$_{10}$=;
on condition that at most two of the residues $A_1$, $A_2$, $A_3$ and $A_4$ stand for —N=;
W stands for —NR$_4$—, —O— or —S—;
X stands for —NR$_{17}$—, —O—, —S(=O)$_{0-2}$— or —CR$_{18}$R$_{19}$—;
$Y_1$, $Y_1'$, $Y_2$, $Y_2'$, $Y_3$, $Y_3'$, $Y_4$ and $Y_4'$ are respectively selected independently of one another from the group consisting of —H, —F, —Cl, —Br, —I, —CN, —NO$_2$, —CHO, —R$_0$, —C(=O)R$_0$, —C(=O)—H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)—R$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)—N(R$_0$)$_2$; or $Y_1$ and $Y_1'$, or $Y_2$ and $Y_2'$, or $Y_3$ and $Y_3'$, or $Y_4$ and $Y_4'$ jointly stand for =O;
on condition that at least one of the residues $Y_1$, $Y_1'$, $Y_2$, $Y_2'$, $Y_3$, $Y_3'$, $Y_4$ and $Y_4'$ does not stand for —H;
$R_0$ respectively independently stands for —C$_{1-8}$-aliphatic, —C$_{3-12}$-cycloaliphatic, -aryl, heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;
$R_1$ and $R_2$, independently of one another, stand for —H or —R$_0$; or $R_1$ and $R_2$ together stand for —CH$_2$CH$_2$OCH$_2$CH$_2$—, —CH$_2$CH$_2$NR$_{11}$CH$_2$CH$_2$— or —(CH$_2$)$_{3-6}$—;
$R_3$ stands for —R$_0$;
$R_4$ stands for —H, —R$_0$, —COR$_{12}$ or —S(=O)$_2$R$_{12}$;
$R_5$, $R_6$, $R_7$, $R_8$, $R_9$, $R_{10}$, $R_{18}$ and $R_{19}$, respectively independently of one another, stand for —H, —F, —Cl, —Br, —I, —NO$_2$, —CF$_3$, —OR$_{13}$, —SR$_{13}$, —SO$_2$R$_{13}$, —S(=O)$_2$OR$_{13}$, —CN, —COOR$_{13}$, —CONR$_{13}$, —NR$_{14}$R$_{15}$, =O or —R$_0$; or $R_5$ and $R_6$ jointly stand for —(CH$_2$)$_{2-6}$—, wherein individual hydrogen atoms can also be replaced by —F, —Cl, —Br, —I, —NO$_2$, —CF$_3$, —OR$_{13}$, —CN or —C$_{1-6}$-aliphatic;
$R_{11}$ respectively independently stands for —H, —R$_0$ or —C(=O)R$_0$;
$R_{12}$ respectively independently stands for —H, —R$_0$, —OR$_{13}$, or —NR$_{14}$R$_{15}$;
$R_{13}$ respectively independently stands for —H or R$_0$;

$R_{14}$ and $R_{15}$ respectively independently of one another stand for —H or $R_0$; or $R_{14}$ and $R_{15}$ together stand for —CH$_2$CH$_2$OCH$_2$CH$_2$—, —CH$_2$CH$_2$NR$_{16}$CH$_2$CH$_2$— or —(CH$_2$)$_{3-6}$—;

$R_{16}$ stands for —H or —C$_{1-6}$-aliphatic;

$R_{17}$ stands for —H, —R$_0$, —COR$_{12}$ or —S(=O)$_2$R$_{12}$;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue;

wherein with respect to "aliphatic" and "cycloaliphatic", "mono- or polysubstituted" means the mono- or polysubstitution of one or more hydrogen atoms by —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)—OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)—N(R$_0$)$_2$, —Si(R$_0$)$_3$ or —PO(OR$_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" means the mono- or polysubstitution of one or more hydrogen atoms of the ring system by substituents selected from the group comprising —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)—N(R$_0$)$_2$, —Si(R$_0$)$_3$ and —PO(OR$_0$)$_2$; wherein if necessary N-ring atoms present can be respectively oxidised;

said compound being in the form of a single stereoisomer or mixture thereof, the free compound and/or a physiologically compatible salt thereof.

2. Compound according to claim 1, which has the formula (1.1), (1.2), (1.3), (1.4), (1.5), (1.6) or (1.7):

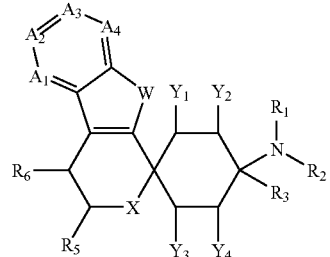
(1.1)

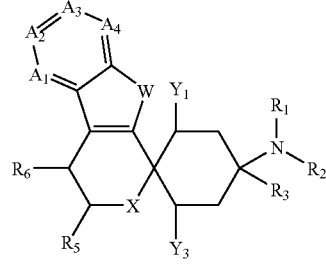
(1.2)

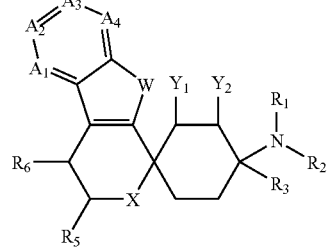
(1.3)

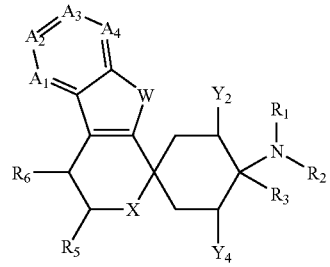
(1.4)

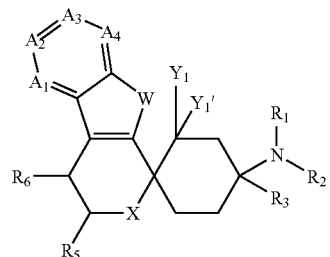
(1.5)

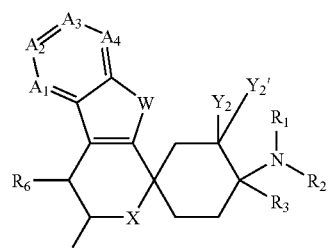
(1.6)

(1.7)

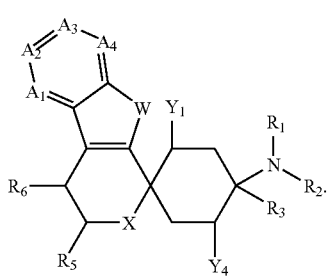

3. Compound according to claim 1, which has the formula (2):

(2)

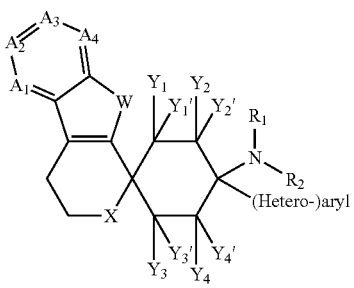

wherein (hetero)aryl stands for -aryl or -heteroaryl.

4. Compound according to claim 3, which has the formula (2.1), (2.2), (2.3) or (2.4):

(2.1)

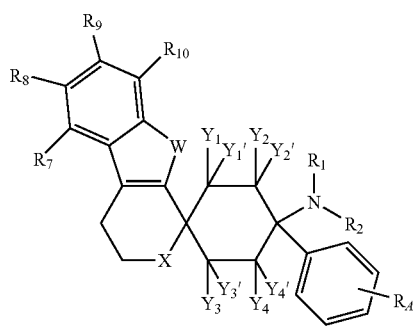

(2.2)

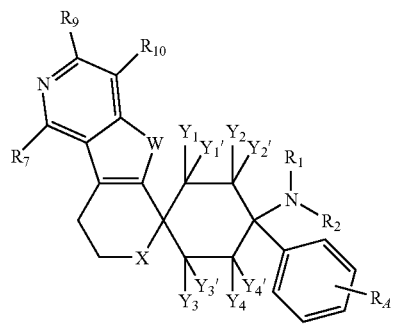

(2.3)

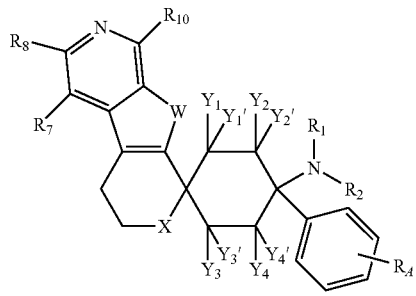

(2.4)

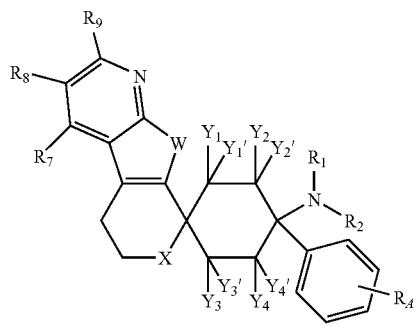

wherein $R_A$ stands for —H, —F, —Cl, —CN or —CH$_3$.

5. Compound according to claim 4, which has the formula (2.1.1) or (2.4.1):

(2.1.1)

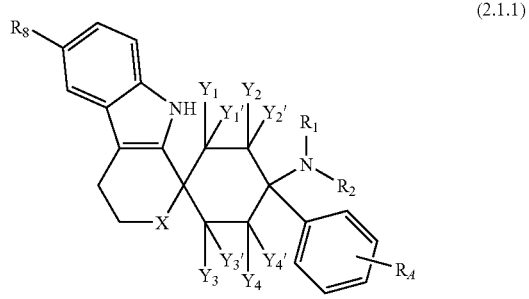

(2.4.1)

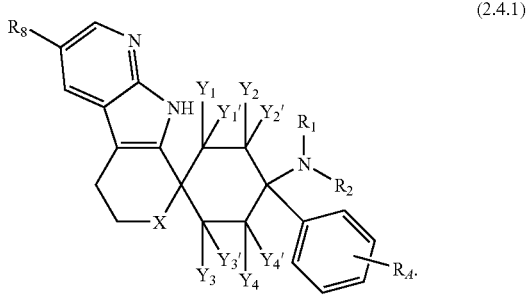

6. Compound according to claim 5, wherein

X stands for —O— or —NR$_{17}$—;

R$_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

R$_1$ stands for —CH$_3$;

R$_2$ stands for —H or —CH$_3$;

R$_8$ stands for —H or —F;

R$_{12}$ respectively independently stands for —H, —R$_0$, —OR$_{13}$, or —NR$_{14}$R$_{15}$;

R$_{13}$ respectively independently stands for —H or R$_0$;

R$_{14}$ and R$_{15}$ respectively independently of one another stand for —H or R$_0$; or R$_{14}$ and R$_{15}$ together stand for —CH$_2$CH$_2$OCH$_2$CH$_2$—, —CH$_2$CH$_2$NR$_{16}$CH$_2$CH$_2$— or —(CH$_2$)$_{3-6}$—;

R$_{16}$ stands for —H or —C$_{1-6}$-aliphatic;

R$_{17}$ stands for —H, —R$_0$, —COR$_{12}$ or —S(=O)$_2$R$_{12}$; and

Y$_1$, Y$_1$', Y$_2$, Y$_2$', Y$_3$, Y$_3$', Y$_4$ and Y$_4$' are respectively selected independently of one another from the group consisting of —H, —F, —Cl, —CN, —C$_{1-8}$-aliphatic, —C$_{1-8}$-aliphatic-NHC$_{1-8}$-aliphatic, —C$_{1-8}$-aliphatic-N(C$_{1-8}$-aliphatic)$_2$, —S—C$_{1-8}$-aliphatic, —S-aryl, -aryl and —C$_{1-8}$-aliphatic-aryl; on condition that at least one of the residues Y$_1$, Y$_1$', Y$_2$, Y$_2$', Y$_3$, Y$_3$', Y$_4$ and Y$_4$' differs from —H; and R$_4$ stands for —H, —F, —Cl, —CN or —CH$_3$.

7. Compound according to claim 1, which is selected from the group consisting of:

(±)-N,N,2-trimethyl-4-phenyl-4',9'-dihydro-3'H-spiro[cyclohexane-1,1'-pyrano[3,4-b]indole]-4-amine; 2-hydroxypropane-1,2,3-tricarboxylate;

(±)-N,N,2-trimethyl-4-phenyl-4',9'-dihydro-3'H-spiro[cyclohexane-1,1'-pyrano[3,4-b]indole]-4-amine; 2-hydroxypropane-1,2,3-tricarboxylate;

(±)-2-methyl-4-(dimethylamino)1-4-phenyl-spiro[cyclohexane-1,8'-(5,6,8,9-tetrahydro-pyrano[3,4-b]-7-azaindole)]; 2-hydroxypropane-1,2,3-tricarboxylate;

(±)-2-benzyl-N,N-dimethyl-4-phenyl-4',9'-dihydro-3'H-spiro[cyclohexane-1,1'-pyrano[3,4-b]indole]-4-amine;

(±)-2-benzyl-N,N-dimethyl-4-phenyl-2',3',4',9'-tetrahydrospiro[cyclohexane-1,1'-pyrido[3,4-b]indole]-4-amine; 2-hydroxypropane-1,2,3-tricarboxylate;

(±)-2-(3-fluorobenzyl)-N,N-dimethyl-4-phenyl-4',9'-dihydro-3'H-spiro[cyclohexane-1,1'-pyrano[3,4-b]indole]-4-amine;

N,N,3,5-tetramethyl-4-phenyl-4',9'-dihydro-3'H-spiro[cyclohexane-1,1'-pyrano[3,4-b]indole]-4-amine;

N,N,2,6-tetramethyl-4-phenyl-4',9'-dihydro-3'H-spiro[cyclohexane-1,1'-pyrano[3,4-b]indole]-4-amine;

N,N,2,5-tetramethyl-4-phenyl-4',9'-dihydro-3'H-spiro[cyclohexane-1,1'-pyrano[3,4-b]indole]-4-amine;

2-benzyl-N,N-dimethyl-4-phenyl-4',9'-dihydro-3'H-spiro[cyclohexane-1,1'-pyrano[3,4-b]indole]-4-amine;

2-(4-fluorobenzyl)-N,N-dimethyl-4-phenyl-4',9'-dihydro-3'H-spiro[cyclohexane-1,1'-pyrano[3,4-b]indole]-4-amine;

N,N,2,3-tetramethyl-4-phenyl-4',9'-dihydro-3'H-spiro[cyclohexane-1,1'-pyrano[3,4-b]indole]-4-amine;

N,N-dimethyl-3,4-diphenyl-4',9'-dihydro-3'H-spiro[cyclohexane-1,1'-pyrano[3,4-b]indole]-4-amine;

2-(4-fluorophenyl)-N,N-dimethyl-4-phenyl-4',9'-dihydro-3'H-spiro[cyclohexane-1,1'-pyrano[3,4-b]indole]-4-amine;

3-((dimethylamino)methyl)-N,N-dimethyl-4-phenyl-4',9'-dihydro-3'H-spiro[cyclohexane-1,1'-pyrano[3,4-b]indole]-4-amine;

N,N,3-trimethyl-4-phenyl-4',9'-dihydro-3'H-spiro[cyclohexane-1,1'-pyrano[3,4-b]indole]-4-amine;

3-fluoro-N,N-dimethyl-4-phenyl-4',9'-dihydro-3'H-spiro[cyclohexane-1,1'-pyrano[3,4-b]indole]-4-amine;

2-fluoro-N,N-dimethyl-4-phenyl-4',9'-dihydro-3'H-spiro[cyclohexane-1,1'-pyrano[3,4-b]indole]-4-amine;

N,N-dimethyl-2-(methylthio)-4-phenyl-4',9'-dihydro-3'H-spiro[cyclohexane-1,1'-pyrano[3,4-b]indole]-4-amine;

N,N-dimethyl-4-phenyl-2-(phenylthio)-4',9'-dihydro-3'H-spiro[cyclohexane-1,1'-pyrano[3,4-b]indole]-4-amine;

3,3-difluoro-N,N-dimethyl-4-phenyl-4',9'-dihydro-3'H-spiro[cyclohexane-1,1'-pyrano[3,4-b]indole]-4-amine;

2,2-difluoro-N,N-dimethyl-4-phenyl-4',9'-dihydro-3'H-spiro[cyclohexane-1,1'-pyrano[3,4-b]indole]-4-amine;

2-allyl-N,N-dimethyl-4-phenyl-4',9'-dihydro-3'H-spiro[cyclohexane-1,1'-pyrano[3,4-b]indole]-4-amine;

N,N,3,5-tetramethyl-4-phenyl-2',3',4',9'-tetrahydrospiro[cyclohexane-1,1'-pyrido[3,4-b]indole]-4-amine;

N,N,2,6-tetramethyl-4-phenyl-2',3',4',9'-tetrahydrospiro[cyclohexane-1,1'-pyrido[3,4-b]indole]-4-amine;

N,N,2,5-tetramethyl-4-phenyl-2',3',4',9'-tetrahydrospiro[cyclohexane-1,1'-pyrido[3,4-b]indole]-4-amine;

2-benzyl-N,N-dimethyl-4-phenyl-2',3',4',9'-tetrahydrospiro[cyclohexane-1,1'-pyrido[3,4-b]indole]-4-amine;

2-(4-fluorobenzyl)-N,N-dimethyl-4-phenyl-2',3',4',9'-tetrahydrospiro-[cyclohexane-1,1'-pyrido[3,4-b]indole]-4-amine;

N,N,2,3-tetramethyl-4-phenyl-2',3',4',9'-tetrahydrospiro[cyclohexane-1,1'-pyrido[3,4-b]indole]-4-amine;

N,N-dimethyl-3,4-diphenyl-2',3',4',9'-tetrahydrospiro[cyclohexane-1,1'-pyrido[3,4-b]indole]-4-amine;

2-(4-fluorophenyl)-N,N-dimethyl-4-phenyl-2',3',4',9'-tetrahydrospiro-[cyclohexane-1,1'-pyrido[3,4-b]indole]-4-amine;

3-((dimethylamino)methyl)-N,N-dimethyl-4-phenyl-2',3',4',9'-tetrahydrospiro-[cyclohexane-1,1'-pyrido[3,4-b]indole]-4-amine;

N,N,3-trimethyl-4-phenyl-2',3',4',9'-tetrahydrospiro[cyclohexane-1,1'-pyrido[3,4-b]indole]-4-amine;

3-fluoro-N,N-dimethyl-4-phenyl-2',3',4',9'-tetrahydrospiro[cyclohexane-1,1'-pyrido[3,4-b]indole]-4-amine;

2-fluoro-N,N-dimethyl-4-phenyl-2',3',4',9'-tetrahydrospiro[cyclohexane-1,1'-pyrido[3,4-b]indole]-4-amine;

N,N-dimethyl-2-(methylthio)-4-phenyl-2',3',4',9'-tetrahydrospiro[cyclohexane-1,1'-pyrido[3,4-b]indole]-4-amine;

N,N-dimethyl-4-phenyl-2-(phenylthio)-2',3',4',9'-tetrahydrospiro[cyclohexane-1,1'-pyrido[3,4-b]indole]-4-amine;

3,3-difluoro-N,N-dimethyl-4-phenyl-2',3',4',9'-tetrahydrospiro[cyclohexane-1,1'-pyrido[3,4-b]indole]-4-amine;

2,2-difluoro-N,N-dimethyl-4-phenyl-2',3',4',9'-tetrahydrospiro[cyclohexane-1,1'-pyrido[3,4-b]indole]-4-amine;

2-allyl-N,N-dimethyl-4-phenyl-2',3',4',9'-tetrahydrospiro[cyclohexane-1,1'-pyrido[3,4-b]indole]-4-amine;

2-benzyl-6'-fluoro-N,N-dimethyl-4-phenyl-4',9'-dihydro-3'H-spiro-[cyclohexane-1,1'-pyrano[3,4-b]indole]-4-amine;

6'-fluoro-2-(3-fluorobenzyl)-N,N-dimethyl-4-phenyl-4',9'-dihydro-3'H-spiro[cyclohexane-1,1'-pyrano[3,4-b]indole]-4-amine;

2-(3-fluorobenzyl)-N,N-dimethyl-4-phenyl-2',3',4',9'-tetrahydrospiro-[cyclohexane-1,1'-pyrido[3,4-b]indole]-4-amine;

3,6'-difluoro-N,N-dimethyl-4-phenyl-4',9'-dihydro-3'H-spiro[cyclohexane-1,1'-pyrano[3,4-b]indole]-4-amine;

2,6'-difluoro-N,N-dimethyl-4-phenyl-4',9'-dihydro-3'H-spiro[cyclohexane-1,1'-pyrano[3,4-b]indole]-4-amine;

3,3,6'-trifluoro-N,N-dimethyl-4-phenyl-4',9'-dihydro-3'H-spiro[cyclohexane-1,1'-pyrano[3,4-b]indole]-4-amine;

2,2,6'-trifluoro-N,N-dimethyl-4-phenyl-4',9'-dihydro-3'H-spiro[cyclohexane-1,1'-pyrano[3,4-b]indole]-4-amine;

2,6,6'-trifluoro-N,N-dimethyl-4-phenyl-4',9'-dihydro-3'H-spiro[cyclohexane-1,1'-pyrano[3,4-b]indole]-4-amine;

2,2,6'-trifluoro-N-methyl-4-phenyl-4',9'-dihydro-3'H-spiro[cyclohexane-1,1'-pyrano[3,4-b]indole]-4-amine;

2,6'-difluoro-N-methyl-4-phenyl-4',9'-dihydro-3'H-spiro[cyclohexane-1,1'-pyrano[3,4-b]indole]-4-amine;
2,6,6'-trifluoro-N-methyl-4-phenyl-4',9'-dihydro-3'H-spiro[cyclohexane-1,1'-pyrano[3,4-b]indole]-4-amine;
3,3,6'-trifluoro-N,N-dimethyl-4-(thiophen-2-yl)-4',9'-dihydro-3'H-spiro[cyclohexane-1,1'-pyrano[3,4-b]indole]-4-amine;
4-butyl-3,3,6'-trifluoro-N,N-dimethyl-4',9'-dihydro-3'H-spiro[cyclohexane-1,1'-pyrano[3,4-b]indole]-4-amine;
2,2,6'-trifluoro-N,N-dimethyl-4-(thiophen-2-yl)-4',9'-dihydro-3'H-spiro[cyclohexane-1,1'-pyrano[3,4-b]indole]-4-amine;
4-butyl-2,2,6'-trifluoro-N,N-dimethyl-4',9'-dihydro-3'H-spiro[cyclohexane-1,1'-pyrano[3,4-b]indole]-4-amine;
2,6,6'-trifluoro-N,N-dimethyl-4-(thiophen-2-yl)-4',9'-dihydro-3'H-spiro-[cyclohexane-1,1'-pyrano[3,4-b]indole]-4-amine;
4-butyl-2,6,6'-trifluoro-N,N-dimethyl-4',9'-dihydro-3'H-spiro[cyclohexane-1,1'-pyrano[3,4-b]indole]-4-amine;
3,6'-difluoro-N,N-dimethyl-4-(thiophen-2-yl)-4',9'-dihydro-3'H-spiro-[cyclohexane-1,1'-pyrano[3,4-b]indole]-4-amine;
4-butyl-3,6'-difluoro-N,N-dimethyl-4',9'-dihydro-3'H-spiro[cyclohexane-1,1'-pyrano[3,4-b]indole]-4-amine;
2,6'-difluoro-N,N-dimethyl-4-(thiophen-2-yl)-4',9'-dihydro-3'H-spiro-[cyclohexane-1,1'-pyrano[3,4-b]indole]-4-amine;
4-butyl-2,6'-difluoro-N,N-dimethyl-4',9'-dihydro-3'H-spiro[cyclohexane-1,1'-pyrano[3,4-b]indole]-4-amine;
3,3,6'-trifluoro-4-(3-fluorophenyl)-N,N-dimethyl-2',3',4',9'-tetrahydrospiro-[cyclohexane-1,1'-pyrido[3,4-b]indole]-4-amine;
2,2,6'-trifluoro-4-(3-fluorophenyl)-N,N-dimethyl-2',3',4',9'-tetrahydrospiro-[cyclohexane-1,1'-pyrido[3,4-b]indole]-4-amine;
3,6'-difluoro-4-(3-fluorophenyl)-N,N-dimethyl-2',3',4',9'-tetrahydrospiro-[cyclohexane-1,1'-pyrido[3,4-b]indole]-4-amine;
2,6'-difluoro-4-(3-fluorophenyl)-N,N-dimethyl-2',3',4',9'-tetrahydrospiro-[cyclohexane-1,1'-pyrido[3,4-b]indole]-4-amine;
2,6,6'-trifluoro-4-(3-fluorophenyl)-N,N-dimethyl-2',3',4',9'-tetrahydrospiro-[cyclohexane-1,1'-pyrido[3,4-b]indole]-4-amine;
3,3-difluoro-N,N-dimethyl-4-phenyl-2',3',4',9'-tetrahydrospiro[cyclohexane-1,1'-pyrido[3,4-b]indole]-4-amine;
2,2-difluoro-4-(3-fluorophenyl)-N,N-dimethyl-2',3',4',9'-tetrahydrospiro-[cyclohexane-1,1'-pyrido[3,4-b]indole]-4-amine;
3-fluoro-4-(3-fluorophenyl)-N,N-dimethyl-2',3',4',9'-tetrahydrospiro-[cyclohexane-1,1'-pyrido[3,4-b]indole]-4-amine;
2-fluoro-4-(3-fluorophenyl)-N,N-dimethyl-2',3',4',9'-tetrahydrospiro-[cyclohexane-1,1'-pyrido[3,4-b]indole]-4-amine;
2,6-difluoro-4-(3-fluorophenyl)-N,N-dimethyl-2',3',4',9'-tetrahydrospiro-[cyclohexane-1,1'-pyrido[3,4-b]indole]-4-amine;
(E)-1-(4-(dimethylamino)-3-fluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-2-fluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-3,3-difluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-2,2-difluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,6-difluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-3,6'-difluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,6'-difluoro-4-(3-fluorophenyl)-3',4'-dihydrospiro-[cyclohexane-1,1'-pyrido[3,4-b]indole]-2'(9'H)-yl)-3-phenylprop-2-en-1-one;
(E)-1-(4-(dimethylamino)-3,3,6'-trifluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,2,6'-trifluoro-4-(3-fluorophenyl)-3',4'-dihydrospiro[cyclohexane-1,1'-pyrido[3,4-b]indole]-2'(9'H)-yl)-3-phenylprop-2-en-1-one;
(E)-1-(4-(dimethylamino)-2,6,6'-trifluoro-4-(3-fluorophenyl)-3',4'-dihydrospiro[cyclohexane-1,1'-pyrido[3,4-b]indole]-2'(9'H)-yl)-3-phenylprop-2-en-1-one;
2-methyl-4-(dimethylamino)1-4-phenyl-spiro[cyclohexane-1,8'-(5,6,7,8,9-pentahydro-pyrido[3,4-b]-7-aza-indole)];
N,N,2-trimethyl-4-phenyl-2',3',4',9'-tetrahydrospiro[cyclohexane-1,1'-pyrido[3,4-b]indole]-4-amine;
2-benzyl-N,N-dimethyl-4-phenyl-2', 3',4',9'-tetrahydrospiro[cyclohexane-1,1'-pyrido[3,4-b]indole]-4-amine; and
2-benzyl-N,N-dimethyl-4-phenyl-2', 3',4',9'-tetrahydrospiro[cyclohexane-1,1'-pyrido[3,4-b]indole]-4-amine;
6'-fluoro-2-(3-fluorobenzyl)-N,N-dimethyl-4-phenyl-4',9'-dihydrospiro-[cyclohexane-1,1'-pyrano-[3,4-b]indole]-4-amine;
2-(3-fluorobenzyl)-N,N-dimethyl-4-phenyl-2',3',4',9'-tetrahydrospiro-[cyclohexane-1,1'-pyrido[3,4-b]indole]-4-amine;
N,N-dimethyl-4-phenyl-2-(phenylthio)-4',9'-dihydro-3'H-spiro-[cyclohexane-1,1'-pyrano[3,4-b]indole]-4-amine;
N,N-dimethyl-4-phenyl-2-(phenylthio)-2',3',4',9'-tetrahydrospiro[cyclohexane-1,1'-pyrido[3,4-b]indole]-4-amine;
2-(3-fluorobenzyl)-N,N-dimethyl-4-phenyl-2',3',4',9'-tetrahydrospiro-[cyclohexane-1,1'-pyrido[3,4-b]indole]-4-amine;
2-(4-(dimethylamino)-4-phenyl-4',9'-dihydro-3'H-spiro[cyclohexane-1,1'-pyrano[3,4-b]indole]-2-yl)methyl acetate;
2-allyl-N,N-dimethyl-4-phenyl-4',9'-dihydros-3'H-spiro[cyclohexane-1,1'-pyrano[3,4-b]indole]-4-amine;
2-fluoro-N,N-dimethyl-4-phenyl-4',9'-dihydro-3'H-spiro[cyclohexane-1,1'-pyrano[3,4-b]indole]-4-amine;
2-allyl-N,N-dimethyl-4-phenyl-4',9'-dihydros-3'H-spiro[cyclohexane-1,1'-pyrano[3,4-b]indole]-4-amine;
2,6'-difluoro-N,N-dimethyl-4-phenyl-4',9'-dihydro-3'H-spiro[cyclohexane-1,1'-pyrano[3,4-b]indole]-4-amine;
4-(dimethylamino)-4-phenyl-4',9'-dihydro-3'H-spiro[cyclohexane-1,1'-pyrano[3,4-b]indole]-2-yl)methanol;
2,6'-difluoro-N,N-dimethyl-4-phenyl-4',9'-dihydro-3'H-spiro[cyclohexane-1,1'-pyrano[3,4-b]indole]-4-amine;
2-fluoro-N,N-dimethyl-4-phenyl-2',3',4',9'-tetrahydrospiro[cyclohexane-1,1'-pyrido[3,4-b]indole]-4-amine;
2-fluoro-N,N-dimethyl-4-phenyl-2',3',4',9'-tetrahydrospiro[cyclohexane-1,1'-pyrido[3,4-b]indole]-4-amine;

2-(4-(dimethylamino)-4-phenyl-4',9'-dihydro-3'H-spiro[cyclohexane-1,1'-pyrano[3,4-b]indole]-2-yl)ethanol;

2-(4-(dimethylamino)-4-phenyl-4',9'-dihydro-3'H-spiro[cyclohexane-1,1'-pyrano[3,4-b]indole]-2-yl)methyl)isoindoline-1,3-dione;

N-((4-(dimethylamino)-4-(3-fluorophenyl)-4',9'-dihydro-3'H-spiro-[cyclohexane-1,1'-pyrano[3,4-b]indole]-2-yl)methyl)-3-phenylcinnamic acid amide;

tert-butyl 2-(2-(4-(dimethylamino)-4-phenyl-4',9'-dihydro-3'H-spiro[cyclohexane-1,1'-pyrano[3,4-b]indole]-2-yl)ethoxy)acetate;

2-(4-(dimethylamino)-4-phenyl-4',9'-dihydro-3'H-spiro[cyclohexane-1,1'-pyrano[3,4-b]indole]-2-yl)acetonitrile and the physiologically compatible salts thereof.

8. A pharmaceutical composition comprising at least one compound according to claim 1, said compound being in the form of a single stereoisomer or mixture thereof, the free compound and/or a physiologically compatible salt thereof, and optionally one or more suitable additives and/or adjuvants and/or further active substances.

9. A method of treating pain in a patient in need of such treatment, said method comprising administering to said patient an effective amount therefor of a compound according to claim 1, said compound being in the form of a single stereoisomer or mixture thereof, the free compound and/or a physiologically compatible salt thereof.

* * * * *

UNITED STATES PATENT AND TRADEMARK OFFICE
CERTIFICATE OF CORRECTION

PATENT NO. : 8,293,758 B2
APPLICATION NO. : 12/410544
DATED : October 23, 2012
INVENTOR(S) : Zemolka et al.

It is certified that error appears in the above-identified patent and that said Letters Patent is hereby corrected as shown below:

In the specification,

Column 15, line 32, "-$C_{2-4}$-alkenyl" -- should read -- -$C_{2-6}$-alkenyl --.

Column 23, line 9, "-alkynylene" -- should read -- alkinylene --.

Column 25, line 10, "benzoxadiazolyl" -- should read -- benzooxadiazolyl --.

Column 36, line 29, "cyclohexane 1, pyrano" -- should read -- cyclohexane 1, 1'-pyrano --.

Column 36, line 58, "ethanol" -- should read -- ethanol; --.

Column 49, lines 6, 7, "-3-fluorobenzoyl" -- should read -- -3-fluorobenzol --.

Column 50, line 8, "On" -- should read -- *On --.

Column 57, line 33, "widely" -- should read -- *widely --.

Column 61, line 42, "Mon-polar" -- should read -- Non-polar --.

Column 63, line 5, "J=Hz" -- should read -- J=5Hz --.

Column 66, lines 60, 61, "isoindoline" -- should read -- isoindolin --.

Column 67, line 26, "isoindoline" -- should read -- isoindolin --.

Column 67, line 67, "163.1" -- should read -- 163.1, 164.8 --.

Column 69, line 19, "nociceptine" -- should read -- nociceptin --.

Signed and Sealed this
First Day of December, 2015

Michelle K. Lee
*Director of the United States Patent and Trademark Office*

CERTIFICATE OF CORRECTION (continued)
U.S. Pat. No. 8,293,758 B2

Column 69, line 22, "nociceptine" -- should read -- nociceptin --.

In the claims,

Column 81, line 5, "isoindoline" -- should read -- isoindolin --.